US006197504B1

(12) United States Patent
Chow

(10) Patent No.: US 6,197,504 B1
(45) Date of Patent: Mar. 6, 2001

(54) METHOD OF DETECTING EXPRESSION OF MAB-21

(76) Inventor: King Lau Chow, 23A Block 20, Laguna City, Lam Tin (HK)

(*) Notice: Subject to any disclaimer, the term of this patent is extended or adjusted under 35 U.S.C. 154(b) by 0 days.

(21) Appl. No.: 09/008,697

(22) Filed: Jan. 19, 1998

Related U.S. Application Data

(63) Continuation-in-part of application No. 08/835,604, filed on Apr. 9, 1997.
(60) Provisional application No. 60/011,607, filed on Apr. 10, 1996.

(51) Int. Cl.[7] .................................................. C12Q 1/68
(52) U.S. Cl. ................................................................ 435/6
(58) Field of Search .................................................. 435/6

(56) References Cited

PUBLICATIONS

Chow, King L. and Emmons, Scott W., (1994) "HOM–C/Hox genes and four interacting loci determine the morphogenetic properties of single cells in the nematode male tail" *Developement* 120: 2579–2593 (Exhibit 1);.

Chow, King L., et al., (1995) "The mab–21 gene of Caenorhabditis elegans encodes a novel protein required for choice of alternate Cell fates" *Development* 121:3615–3626 (Exhibit 2);.

Dreyfus, David H. and Emmons, Scott W., (1991) "A transposon–related palindromic repetitive sequence from C.elegans" *Nucleic Acids Research* 19(8):1871–1877 (Exhibit 3).

Parker, Thomas G., et al., (Feb. 1991) "Modulation of the Cardiac Phenotype by Transforming and Fibroblast Growth Factors Resembles the Induction of Fetal Cardiac Genes During Pressure–Overload Hypertrophy" *Journal of Vascular Medicine an Biology* 3(1):38–43 (Exhibit 4).

Wong, Rebecca Lee Yean, Chan, Kenith Ka Lung, and Chow, King Lau (in press) "Developement expression of Mab2112 during mouse embryogenesis".

Hong Kong University of Science and Technology pp. 1–12 (Exhibit 5); and Wong, R.L.Y., Wong, H.T., and Chow, K.L. (In press) "Genomic cloning and chromosomal localization of the mouse Mab2112 locus" *Cytogenet Cell Genet* pp. 1–11 (Exhibit 6).

*Primary Examiner*—Terry McKelvey
(74) *Attorney, Agent, or Firm*—Cooper & Dunham LLP

(57) ABSTRACT

This invention provides vectors comprising isolated polynucleotides comprising a member selected from the group consisting of: (a) a polynucleotide encoding MAB-21 protein; (b) a polynucleotide capable of hybridizing to and which is at least 60% identical to the polynucleotide of (a); and (c) a polynucleotide fragment of the polynucleotide of (a) or (b). This invention further provides host-vectors system for the expression of MAB-21 protein and protein products of mab-21 homologs. This invention further provides MAB-21 protein and protein products of mab-21 homologs. This invention also provides antibodies capable of specifically binding to the MAB-21 protein or protein products of mab-21 homologs. Finally, this invention also provides methods for identifying various suppressor, enhancer and modifier genes of the mab-21 and its homologs.

2 Claims, 46 Drawing Sheets

FIGURE 2C
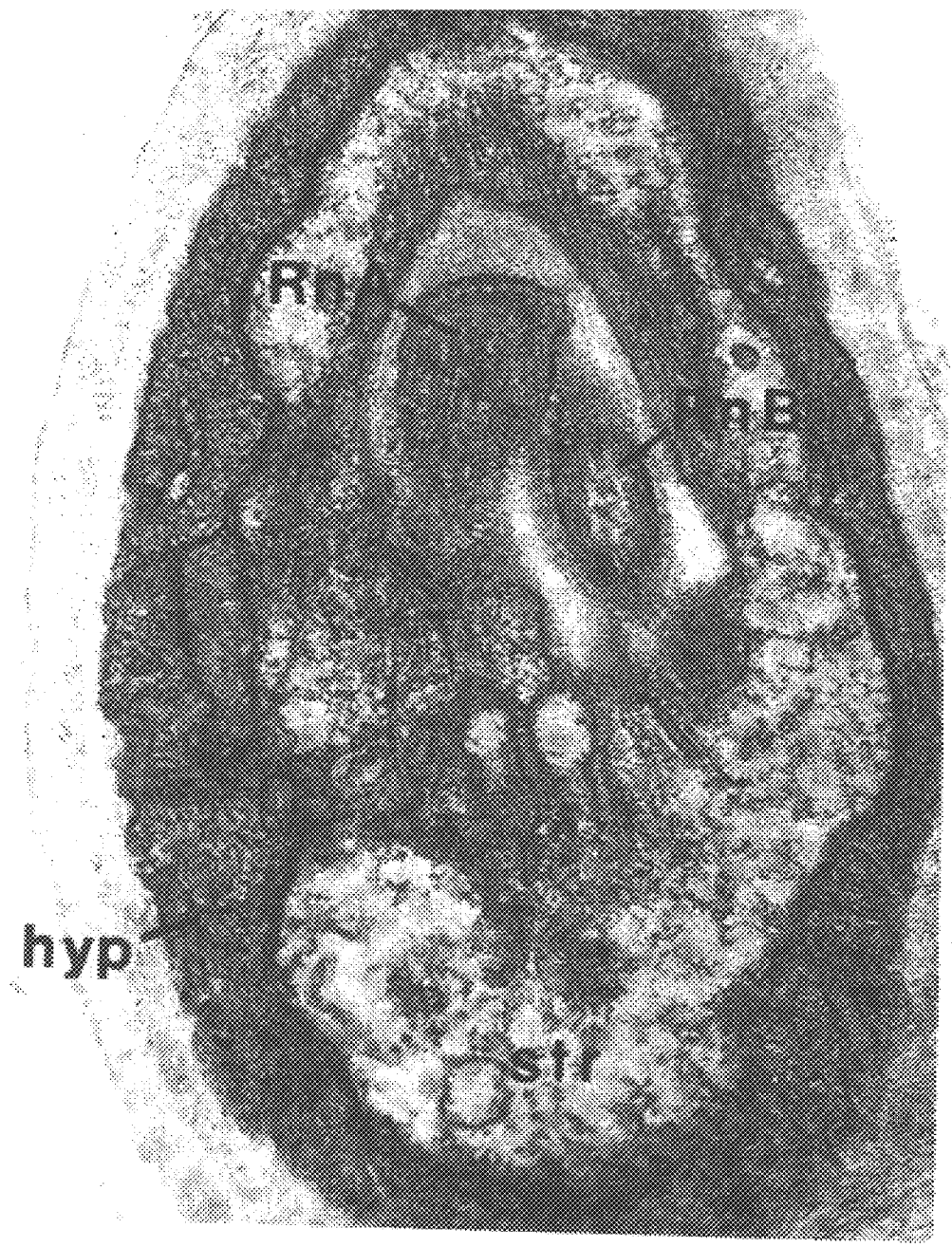
1.0 micron

FIGURE 8A

```
B. malayi     1                                              M S G Q N A A V T S Y Q V S H Y F N E R V A T R K S H V H K A I Y  33
C. briggsae   1                                                                                                                  0
C. elegans    1                              M L G H N Q N V - V Y Q V N N Y F N E K V Q H R K V R V T K T V Q  32
H. sapiens    1                              M I A A - Q A K L V Y H L N K Y Y N E K C Q A R K A A I A K T I R  32
M. musculus   1                                                                                                                  0
F35G12.6      1                              M L G H N Q N V - V Y Q V N N Y F N E K V Q H R K V R V T K T V Q  32

B. malayi    34  M I A K I V Q E I L K E V E A Q E P R F I S T L I E N - N G R Y E  65
C. briggsae   1                                                                                                                  0
C. elegans   33  R I A K V V Q E I L K E V E A Q E P R F I N T L S E T T G R F D  65
H. sapiens   33  E V C K V V S D V L K E V E V Q E P R F I S S L N E M D - N R Y E  64
M. musculus   1                              Q E P R F I S S L N E M D - N R Y E  17
F35G12.6     33  R I A K V V Q E I L K E V E A Q E P R F I N T L S E T T G R F D  65

B. malayi    66  G I I V H S P C E Y E V I L Y L N Q M G V F N F V D D G S I Q G C  98
C. briggsae   1                                                                                                                  0
C. elegans   66  G I V V H S P S E Y E A V L Y L N Q M G V F N F V D D G T I Q G C  98
H. sapiens   65  G L E V I S P T E F E V V L Y L N Q M G V F N F V D D G S L P G C  97
M. musculus  18  G L E V I S P T E F E V V - Y L N Q M G V F N F V D D G S L P G C  49
F35G12.6     66  G I V V H S P S E Y E A V L Y L N Q M G V F N F V D D G T I Q G C  98

B. malayi    99  A V L K L S D G R K R S M S L W V E F I T A S G Y L S                      125
C. briggsae   1                                              E F I T A S G Y L S A R K I R H  16
C. elegans   99  A V L K L S D G R K R S M S L W V E F I T A S G Y L S A R K I R H  131
H. sapiens   98  A V L K L S D G R K R S M S L W V E F I T A S G Y L S A R K I R S  130
M. musculus  50  A V L K L S D G R K R T M S L W V E F I T A S G Y L S A R K I R S  82
F35G12.6     99  A V L K L S D G R K R S M S F G S S S L L L D I Y Q L A R F A T  131
```

FIGURE 8B

```
C. briggsae   17   RFQNIVAQ VLQTPQFSEYCKLLQDNTDVRVRVD   49
C. elegans   132   RFQNIVAQ VLQTPQFSDYCKLLQDNTDVRVRVD  164
H. sapiens   131   RFQTLVAQ AVDKCSYRDVVKMVADTSEVKLRIR  163
M. musculus   83   RFQTLVAQ AVDKCSYRDVVKMIADTSEVKLRIR  115
F35G12.6     132   DSKILWLKFYKLHNS- - - - - - - - - - - - -  146

C. briggsae   50   DKYTVQITCAFRCNGIWPRSASHWPLAGLPWPN   82
C. elegans   165   DKYTVQITCAFRCNGIWPRSASHWPIAGLPWPN  197
H. sapiens   164   DRYVVQITPAFKCTGIWPRSAAHWPLPHIPWPG  196
M. musculus  116   ERYVVQITPAFKCTGIWPRSAAHWPLPHIPWPG  148
F35G12.6     147   - - - - - - - - - - - - - - - - - - - - - - - - - -GLPWPN  152

C. briggsae   83   TALANQTKAEGFDLTSRETAITQHNNPNKQAST  115
C. elegans   198   AALANQTKAEGFDLTSRETAITQQNNPNKQASS  230
H. sapiens   197   PNRVAEVKAEGFNLLSKECHSLAG- - -KQ- -SS  224
M. musculus  149   PNRVAEVKAEGFNLLSKECYSLTG- - -KQ- -AS  176
F35G12.6     153   AALANQTKAEGFDLTSRETAITQQNNPNKQASS  185

C. briggsae  116   MEADAWAMKMHGAENMLLTGGRR-KTLSILKCL  147
C. elegans   231   MEADAWAMKMHGAENMLLTGGRR-KTLSILKCL  262
H. sapiens   225   AESDAWVLQFAEAENRLQMGGCRKKCLSILKTL  257
M. musculus  177   AESDAWVLQFGEAENRLLMGGCRNKCLSVQKTL  209
F35G12.6     186   MEADAWAMKMHGAENMLLTGGRR-KTLSILKCL  217
```

FIGURE 8C

```
C. briggsae   148  RD AHMD FPGTPVTN YI LKTLVLYECEKHCSEYE      180
C. elegans    263  RD AHMD FPGTPVTN YI LKTLVLYECEKHCSEYE      295
H. sapiens    258  RDRHLELPGQPLNN YHMKTLVLYECEKHPRESD         290
M. musculus   210  RDRHLELPGQPLNN YHMKTLLLYECEKHPRETD         242
F35G12.6      218  RD AHMD FPGTPVTN YI LKTLVLYECEKHCSEYE      250

C. briggsae   181  WEDTNIGDRLVGVLLQLVSCLQCRRCAHYFLPS          213
C. elegans    296  WEDPNIGDRLVGILLQLVSCLQCRRCAHYFLPS          328
H. sapiens    291  WDESCLGDRLNGILLQLISCLQCRRCPHYFLPN          323
M. musculus   243  WDEACLGDRLNGILLQLISCLQCRRCPHYFLPN          275
F35G12.6      251  WEDPNIGDRLVGILLQLVSCLQCRRCAHYFLPS          283

C. briggsae   214  LDLLRAKPTHT-IEHSAKLTWHLVRKLMIDPNA          245
C. elegans    329  LDLLRSKPVHS-IEHSAQLAWHLVRKLMIDPNA          360
H. sapiens    324  LDLFQGKP-IHSALENAAKQTWRLAREILTNPKS         355
M. musculus   276  LDLFQGKP-HSALESAAKQTWRLAREILTNPKS          307
F35G12.6      284  LDLLRSKPVHS-IEHSAQLAWHLVRKLMIDPNA          315

C. briggsae   246  LQTL                                        249
C. elegans    361  LQSL                                        364
H. sapiens    356  LEKL                                        359
M. musculus   308  LDKL                                        311
F35G12.6      316  LQSL                                        319
```

FIGURE 9A *Caenorhabditis briggsae mab-21* homolog sequences
Genomic sequence with translation product deduced from comparison with *C. elegans* sequence DNA sequence 5'GAATTCATAACGCTTCGGGATATCTTTCGGCTCGAAAAATTCGTCACCGATTCCAAA
ACATTGTGCCCAAGTTCTCCAGACTCCACAATTTAGTAATTCAAAAAAAGCACTAATC
ACGTTTTGTAAAACTTCAGCGAATACTGTAAACTTCTACAAGACAACACTGATGTACGA
GTAAGAGTGGATGATAAGTACACGGTTCAAATCACTTGTGCATTCGATGTAATGGAATT
TGGCCTAGATCAGCCAGTCATTGGCCTTTAGCTGGTCTACCATGGCCGAATACGGCATTG
GCTAATCAAACAAAAGCAGAAGGATTCGATCTGACTAGTCGAGAAACTGCAATTACTCAG
CATAACAATCCGAATAAACAGGCTAGCACAATGGAAGCGGACGCTTGGGCAATGAAGATG
CACGGAGCCGAGAACATGCTACTGACTGGAGGTAGACGGAGAAACTTTGAGCATTCTGAAA
TGCCTTCGAGATGCTCATATGGACTTTCCTGGAACACCAGTAACAAACTATATCCTGAAG
ACCTTGGTTCTATACGAATGTGAGAAGCACTGTAGTGAGTGAATGGAAGACACAAAC
ATTGGAGATCGCCTTGTCGGGTAAGTT..........GGNCCTCCAGGGANNCN
AGCAAANNCAAGGCNGGAAAAGGGCGGNNGACCCCCAATGGGAAGGNGGNACGNCTNG
GGCCCATTGGGNGGNTGCGNGGAACCNCGAAGAAAAATTCCTCCCTGGCCTGGGGGNN
AGANAAGGAAGAAACNTNTGANCCAATTCTTGAGGAATGCCCAACGNAGATGCTCCAGGGT
GGAGACGTTCCCTGGGGACACCACCCAGTTAGCGACCTAATATCGCTGGAAAACTCNTTGTT
CTGTGCCGAATGTGAGAAAGCCCCTGTAGTGAGTATGAAATGGAAGGACACANAACAT
TGGAGATCGTCTCGTTGGTGAGTATTTCAATAATTGAAATTAAAGTAGTCTGTGACTTGTCGT
ACAACATTTTTCATTCTAAAATGTACTCTTCTTCTGATGACAATTCTGTGACTTGTCGT
TTTTAACTTCCACAGAAGCCGTTAAAAAAGCATTGCGTGACAAAAGAAGAACGACGCCTT
CGTTTTTTCTTGCTCCTGCTTCTATCCATCTTCCTCGAGGTGCTGCCCTCCCTATTTTTCT
TTCTATTTCTGAGAGCCTCGGCATGCATTCCTAATGGATTCCTTCGTGTTCAACCGGAAA
GTGCCTACACGGAAAGGAAGAAAAAAACGAGGAGTTTGTTCTTCTTTGTATATTGCATAT
ACGTTATATTCATCTTATTTCCCTCCTAATCAACTAGTGCGTGAAATCTTTGAAGAAG
TGAAGAGCAGACAGTGTGAAATGAAGGAGGGCATAGACACAAAAGATGTCATACCGAATTA

FIGURE 9B

```
GGTTTGCGGNCTNNCACCCAGNGAGGAAACGATTTCAATTCATNGAAAAACAAACGTTT
GAAACTGACTATGAGGGGTTGGGCAGAGAAAAAAAGATTTGGATTCTTGATCAAGAACTGG
AACCGAAAAACGACTTTCAGGTGTTCTCCTACAACTGTCAGCTGTCTCCAATGTCGCCG
ATGTGCTCATTATTCCTCCCATCGTTGGATTTACTCCGTGCAAACCAACCACACAAT
CGAACATTCTGCCAAACTCACCTGGCACCTGTTCGCAAACTTATGATTGACCCGAATGC
TTTGCAAACTTTATGATTGATACAGTATTCCTTCTCTTTTCTCACTCTGTTCTTTTCA
TTCTTTCTCACCGATTTGATACAGTATTCCTTCTCTTTTTTCTCATAATAAATTTTTT
GTACCCTAATTACCTGAGCACCTGAGCGTTCAGGAACAACGACTCCAGGACGATGA
AGAATAGATCTGAAGCGGTCACAGATAGCGTTCAGGAACAACGACTCCAGGACGATGA
GTTTGGCAGCAGTGGAGAAGCACGCACTTTCTCCCTGTAATTAGGTATTTAAAGCATCCAAT
CTCAGGTTGCGTCACTCTTTCTCTTAAATGGTGCTCCAAAGCATCATCGTCGTTTGACAAAATGGCATGAGC
TATAGAATATATCCTTTAAATGGTGCTCCAAAGCATCATCGTCGTTTGACAAAATGGCATGAGC
CCCAAACTACTGCGGNCTTGTCCCTCCACTCTCAGGTGCCTTNTCTCATTNNNNNGGAAAAGGA
AATTAGAAGTAAGCTCCCGCTCCACTCTCAGGTGCCTTNTCTCATTNNNNNGGAAAAGGA
AGGAGGGGGGAAGGGGTTCTTAAAGAGATTCACTTCTTGGGGTGAGTGGGGCCGAAA
AATGAGAAAGCGAAATGTTTGTANNCNGAGNNGNACCCATTCCGAACAGAAAGAGATTGG
GAAAGGGTTNCTGAGTGATGAGAAACAACGAGGAGTGTGAAACTATAGTAAACTGGAATCT
GCGATTTTGAAGAAGAAACAACGAGGAGTGTGAAACTATAGTAAACTGGAATCT
GAGACTCCCGTGAACANCCTAGGAAGCTTAATAATCTGTAGGCACCCATACCAACTGTC
ACCAAAATAACATCTGTCGAATTC 3'
```

Protein sequence

EFITASGYLSARKIRHRFQNIVAQVLQTPQFSEYCKLLQDNTDVRVRVDDKYTVQITCAF
RCNGIWPRSASHWPLAGLPWPNTALANQTKAEGFDLTSRETAITQHNNPNKQASTMEADA
WAMKMHGAENMLLTGGRRKTLSILKCLRDAHMDFPGTPVTNYILKTLVLYECEKHCS...
EYEWEDTNIGDRLVGVLLQLVSCLQCRRCAHYFLPSLDLLRAKPTHTIEHSAKLTWHLVR
KLMIDPNALQTL

FIGURE 10

*Brugia malayi mab-21* homolog sequence

EST sequence from the parasitic nematode sequence database

DNA sequence

5' ATTTTTGGACTCTACGATAATTTGCATAGCAACCAAACAGGCAAGGATGTCAGGCCAG
AATGCTGCCGTTACTTCCTACCAAGTATCGCATTATTCAACGAAAGGGTAGCCACTCGA
AAAAGTCATGTACACAAGGCAATCTATATGATTGCTAAAATTGTGCAAGAAATCCTTAAA
GAAGTTGAAGCACAGGAACCTCGATTCATTTCTACACTCATTGAAAATAATGGTCGATAT
GAAGGGATTATAGTTCATTCACCGTGCGAATATGAAGTAATCCTATACCTCAATCAAATG
GGAGTTTTCAATTTCGTCGATGATGGCTCTATTCAAGGATGTGCAGTACTAAAATTAAGT
GATGGTAGAAAACGATCAATGTCATTATGGGTGGAATTTATTACCGCCAGCGGCTATCTG
TCA 3'

Protein sequence

MSGQNAAVTSYQVSHYFNERVATRKSHVHKAIYMIAKIVQEILKEVEAQEPRFISTLIEN
NGRYEGIIVHSPCEYEVILYLNQMGVFNFVDDGSIQGCAVLKLSDGRKRSMSLWVEFITA
SGYLS

FIGURE 11

*Caenorhabditis elegans mab-21* sequence from multiple cDNA sequence compilation

```
cDNA sequence

5' CTTCATCATCATCGAAAAAAGAACACACACACGCATATCTGTTTGTGTGCATTTTTC
CCGGTTTCCGCGTGTCCAACATGCTAGGACATAACCAGAACGTTGTTTATCAGGTGAATA
ACTATTTCAACGAAAAGTTCAACATCGTAAAGTTCGTGTCACAAAAACAGTACAAAGAA
TCGCCAAAGTGGTACAAGAAATATTGAAAGAAGTTGAAGCACAAGAACCTCGATTCATTA
ATACATTAAGTGAAACTACAACTGGAAGATTCGATGGAATTGTGGTACATTCTCCATCCG
AGTATGAGGCAGTGCTATACCTCAACCAGATGGGTGTCTTCAATTTTGTTGACGACGGAA
CAATTCAAGGATGTGCAGTTCTCAAACTAAGTGATGGTCGGAAAAGATCAATGTCCCTTT
GGGTCGAGTTCATTACTGCTTCTGGATATTTATCAGCTCGCAAGATTCGCCACCGATTCC
AAAATATTGTGGCTCAAGTTTTACAAACTCCACAATTCAGTGATTACTGTAAGTTGCTAC
AAGATAACACTGATGTGAGAGTTCGAGTAGATGACAAGTACACCGTTCAAATTACTTGTG
CATTTCGATGCAACGGAATCTGGCCTCGATCAGCGAGTCATTGGCCAATTGCAGGACTTC
CATGGCCGAACGCCGCGTTGGCGAATCAGACAAAAGCCGAGGGATTCGACTTGACGAGTC
GTGAAACTGCAATCACTCAACAAAATAATCCGAATAAGCAAGCGAGCAGTATGGAAGCCG
ATGCCTGGGCAATGAAGATGCATGGTGCAGAGAACATGTTACTAACTGGAGGTCGGCGGA
AGACATTGAGCATTCTGAAATGTCTTCGAGATGCTCACATGGACTTTCCGGGAACACCAG
TAACAAACTACATACTGAAGACATTGGTATTGTACGAATGTGAGAAGCACTGTAGTGAAT
ACGAATGGGAAGATCCAAATATCGGAGATCGCCTTGTCGGAATTCTTCTACAACTAGTCA
GCTGCCTCCAATGTCGTCGCTGTGCTCACTATTTCCTTCCATCTTTGGATCTTTTACGTT
CAAAACCAGTCCATTCCATTGAACATTCCGCCCAACTCGCTTGGCATCTCGTTCGCAAAC
TAATGATCGACCCAAATGCTTTGCAAAGTTTGTAATTTTTGATTATCAATTCCCTCAAAC
TCTTTCTCACTCAACTACTGATACAGTTCATACTTATAAATAAATTATTTTCTCCCAAAA
AAAAAAAAAAAAAAAAAAA 3'

Protein sequence

MLGHNQNVVYQVNNYFNEKVQHRKVRVTKTVQRIAKVVQEILKEVEAQEPRFINTLSETT
TGRFDGIVVHSPSEYEAVLYLNQMGVFNFVDDGTIQGCAVLKLSDGRKRSMSLWVEFITA
SGYLSARKIRHRFQNIVAQVLQTPQFSDYCKLLQDNTDVRVRVDDKYTVQITCAFRCNGI
WPRSASHWPIAGLPWPNAALANQTKAEGFDLTSRETAITQQNNPNKQASSMEADAWAMKM
HGAENMLLTGGRRKTLSILKCLRDAHMDFPGTPVTNYILKTLVLYECEKHCSEYEWEDPN
IGDRLVGILLQLVSCLQCRRCAHYFLPSLDLLRSKPVHSIEHSAQLAWHLVRKLMIDPNA
LQSL
```

FIGURE 12A

**Human *Mab21* homolog sequence** from multiple human cDNA sequence compilation cDNA sequence

```
5' GAATTCCACAATAAGGTAATTAGATTTAGAAGTACTCAGTCACTTTAAGTGGATAAAT
GTATTAGTTAAAACTTTAGGGTTTGCTTTTTTGCTGTTTAGATCAAAGTTTTTTCTGATT
CTTCTGTCCTCATTGTGAACATAACCGTGTAGTTGAAACAGTCAAACTTATTTTTGTAAT
GTATGTTATTGTGTGATGCAGTTTTTTGCTTCTGTCTCCAATATTAAACCATTTTCCTAA
TACTTGTTTCTCTCTCTGCGTGTTGTATTGTTGGTAGTCATTATATGTTGGTGATACATC
TGCACACTCACCCCGGACACACACTCAGCACACTTTTCCTCCATTTGATTAACAGTGCTG
CACACACAATGATTACGGGAAAGCSSAWMWAAWKRMGGAAARGKGTGCTTAKTKTGWSTM
CKGGRWGAGCTTTGCTGGGTCTCAGCGCAACTTTTGTTTTTATTCCTGAGAAGGTGATC
TCTCCATGCGGTTCTCTCACACAAGGATTCTTTAAAAGAGGAAGAGAGACAAGCAGAGGG
GGGAGGACAGTCTTTCACTTTAAGAACGGCTGGGCTCAAAGATAAAAGGAAGGGAAAAGC
AGCAGCAGCAGCAGCAGCAGCAGCAGCAGCAGCAGCAGCAGCAGCAGCAGCAGCAGCAGC
AGGGAAACCAACGCTGCAGCACTTCCGAAAGGCATTTTTGATCCATTTCTGAGTGTTGCG
GCCCGTTTCTCCACCGAAGTTGGCTCCAGCTCTAGCAGCCGCATTGGATCCCACAGCTTA
CTGCGAGACTCCGGTGTACAATCCGGATCTCTGCCCCAACATGATTGCGGCCCAGGCCAA
GCTGGTCTACCATCTGAATAAATACTACAACGAAAAATGCCAAGCCAGGAAAGCTGCCAT
TGCCAAAACTATCCGGGAAGTCTGCAAAGTAGTTTCCGACGTACTGAAGGAAGTGGAAGT
GCAGGAGCCGCGGTTCATCAGCTCTCTCAACGAGATGGACAATCGCTACGAGGGCCTCGA
GGTCATCTCCCCCACCGAATTTGAAGTGGTGCTTTATCTCAACCAAATGGGGGTGTTCAA
CTTCGTGGACGATGGCTCACTGCCCGGCTGCGCGGTGCTGAAGTTGAGCGACGGGCGCAA
GAGGAGCATGTCCCTCTGGGTGGAATTCATTACCGCCTCCGGCTACCTCTCGGCGCGCAA
AATCCGGTCCAGGTTTCAGACGCTGGTGGCTCAAGCGGTAGACAAATGTAGCTACCGGGA
TGTGGTAAAGATGGTGGCAGACACCAGCGAAGTGAAACTGAGAATCCGAGATAGGTACGT
GGTGCAGATCACGCCGGCCTTTAAATGCACCGGGATCTGGCCGAGGAGTGCTGCCCACTG
GCCACTTCCCCACATCCCCTGGCCGGGACCCAACCGGGTGGCGGAGGTCAAGGCGGAAGG
TTTCAATCTCTTGTCCAAGGAGTGCCACTCCTTGGCCGGCAAGCAGAGCTCGGCGGAGAG
CGACGCCTGGGTGCTGCAGTTCGCGGAGGCAGAGAACAGACTGCAGATGGGGGCTGCAG
AAAGAAGTGCCTCTCCATCCTCAAAACCTTAAGGGATCGTCACCTTGAACTGCCGGGCCA
GCCCTTGAACAATTACCATATGAAGACTCTGGTTTCCTACGAGTGTGAAAAGCATCCCCG
AGAGTCGGACTGGGACGAGTCTTGCCTGGGTGATCGGCTGAACGGGATTTTGCTGCAACT
TATCTCCTGCCTGCAGTGCCGGCGGTGTCCCCACTACTTTCTACCGAACTTAGATCTGTT
TCAAGGCAAACCTCACTCAGCTCTGGAAAACGCTGCCAAACAAACGTGGCGACTGGCAAG
```

FIGURE 12B

```
AGAGATCCTGACCAACCCGAAAAGTTTGGAAAAACTTTAGAGGATGATTTAATCAAGAGC
CGAAATTATTACCCTTCTCAAAGTCCTTATTAAGTGTAAACTTCTGTTCAATTCCTAATA
TTCCACTCCGCAGTGCAAACAATCTCTTCCTTTAAAAAGGAATAATAATACAATATTTAA
ACATCATCTCACCCACCCCACAAGGGGAGAAAAAGTAGGGGAAGCGGATGGAGAAAAAC
CCAAAGCCACTAGTATTAGAAGACTTCTTTCCACACGATTTCCTATCTCCCTTGAAAAGT
ACACCGTAACACTCCGTAAACAGCCCAGCTGTAACGCCAGACCGAGACGAACACTCTGCC
TAACTATCAAAGGATTATAGCAATCCTGGTGATTTAGGTGCATCTGTCTGTGAGTAAACA
CGATTTGGATATGCCATCTGAAAGAAACTGTAATGTATATTTTGATTTGTAACAAATATT
GTGATCTCACATTGTCTTTGAAAGTGTGGATGTTGGTGTTTTGTGATTTGGTGAACAGAA
CTTAAATTGCCATTCTGGATACTTCCAGACATTTTCCACTAACAAAGATATCATTTAAAG
GTAGATTTCTTCCTGGTACTTTTATCTGTCTTTGAAAGTGTCTGAACTTTAAAAAGTTTA

CATTTTGTTTCAAATATTGCTTGTTCTATTTCTAACATTCCATAAATATACTTGAAATGT
TATTTAAATATATTCAAAGAAATTTGAATTCAGCTTATATAATAACGCTTGAATATCTGA
ATTATATATTTGAAAAATGCACTTGAAATACACTGGATAATTACTTTTGTGATTTAGATT
TTAATTTGTTGCTGGTTTTTATTTAATTAGATGGTAATAAATGAAGTAAAATAAAAAAAA
AAAAAAGGAATTC
```

Protein Sequence

```
MIAAQAKLVYHLNKYYNEKCQARKAAIAKTIREVCKVVSDVLKEVEVQEPRFISSLNEMD
NRYEGLEVISPTEFEVVLYLNQMGVFNFVDDGSLPGCAVLKLSDGRKRSMSLWVEFITAS
GYLSARKIRSRFQTLVAQAVDKCSYRDVVKMVADTSEVKLRIRDRYVVQITPAFKCTGIW
PRSAAHWPLPHIPWPGPNRVAEVKAEGFNLLSKECHSLAGKQSSAESDAWVLQFAEAENR
LQMGGCRKKCLSILKTLRDRHLELPGQPLNNYHMKTLVSYECEKHPRESDWDESCLGDRL
NGILLQLISCLQCRRCPHYFLPNLDLFQGKPHSALENAAKQTWRLAREILTNPKSLEKL
```

FIGURE 13

**Human EST clone, ym36d10, with homology to *mab-21***

DNA sequence

5'
5' ACCATCTGAATAAATACTACAACGAAAAATGCCAAGCCAGGAAAGCTGCCATTGCCAA
AACTATCCGGGAAGTCTGCAAAGTAGTTTCCGACGTACTGAAGGAAGTGGAAGTGCAGGA
GCCGCGGTTCATCAGCTCTCTCAACGAGATGGACAATCGCTACGAGGGCCTCGAGGTCAT
CCCCCCCACCGAATTTGAAGTGGTGCTTTATCTCAACCAAATGGGGGTGTTCAACTTCGT
GGACGATGGCTCACTGCCCGGCTGCGCGGTGCTGAAGTTGAGCGACGGGCGCAAGAGGAG
CATGTCCCTCTGGGTGGAATTCATTACCGCCTCCGGCTAACCTCTCGGCGCGCAAAATCC
GGTCCAGGTTTCAGACGCTGGTGGCTCAAGCGGTAGACAAATGTTAGCTACCGGGATGTG
GTAAAGATNGTGGCAGACACCAGCGAAGTGAAACTNAGAATCCGAGATAGGTACGTTGTN
CAGATCAAGTCCGNCTTTTAATTCT

3'
5' TTTTTTTTTTATTTTACTTCATTTATTACCATCTAATTAAATAAAAACCAGCAACAAA
TTAAAATCTAAATCACAAAAGTAATTATCCAGTGTATTTCAAGTGCATTTTTCAAATATA
TAATTCAGATATTCAAGCGTTATTATATAAGCTGAATTCAAATTTCTTTGAATATATTTA
AATAACATTTCAAGTATATTTATGGAATGTTAGAAATAGAACAAGCAATATTTGAAACAA
AATGTAAACTTTTTAAAGTTCAGACACTTTCAAAGACAGATAAAAGTACCNGGGAGAAAT
CTACCTTTAAATGATATCTTTGTTAGTGGGAAAATGTCTGGGAAGTAT

LNKYYNEKCQARKAAIAKTIREVCKVVSDVLKEVEVQEPRFISSLNERYEGLEVIPPTEF
EVVLYLNQMGVFNFVDDGSLPGCAVLKLSDGRKRSMSLWVEFITAGLSARKIRSRFQTLV
AQAVYRDVVKMVADTSEVKLRIRDRYVVQIKSAF

FIGURE 14

**Human EST clone, ym45d11, with homology to *mab-21***

DNA sequence

5'end sequence
5' CCATCTGAATAAATACTACAACGAAAAATGCCAAGCCAGGAAAGCTGCCATTGCCAAA
ACTATCCGGGAAGTCTGCAAAGTAGTTTCCGACGTACTGAAGGAAGTGGAAGTGCAGGAG
CCGCGGTTCATCAGCTCTCTCAACGAGATGGACAATCGCTACGAGGGCCTCGAGGTCATC
CCCCCCACCGAATTTGAAGTGGTGCTTTATCTCAACCAAATGGGGGTGTTCAACTTCGTG
GACGATGGCTCACTGCCCGGCTGCGCGGTGCTGAAGTTGAGCGACGGGCGCAAGAGGAGC
ATGTCCCTCTGGGTGGAATTCATTACCGCCTCCGGCTAACCTCTTCGGCGCGCAAAATCC
GGTCCAGGTTTTCAGACGCTGGTGGCTCAAGCGGTAGACAAATGTTAGCTTACCGGGATG
TGGTAAAGATGGTGGCCAGACACCAGCGAAGTGAAAATTGAGAATCCGAGATAGGTTACG
TGGTTGCAGATCACGNCGGCTTTT 3'

3'end sequence
5' ATTTTACTTCATTTATTACCATCTAATTAAATAAAAACCAGCAACAAATTAAAATCTA
AATCACAAAAGTAATTATCCAGTGTATTTCAAGTGCATTTTTCAAATATATAATTCAGAT
ATTCAAGCGTTATTATATAAGCTGAATTCAAATTTCTTTGAATATATTTAAATAACATTT
CAAGTATATTTATGGGAATGTTAGAAATAGAACAAGCAATATTTGANACAAAATGTAAAC
TTTTTAAAGTTCAGACACTTTCAAAGGACAGATAAANGTACCNGGGGGGGAATCTACCTT
TAAAATGATATCTTTGTTAGTGGGAAATGTCTGGGAGTATCCGGAATGGCNATTTAAGGT
TCTGTTCCNCCAAATCACCAAAACACCNACCTTCCACACTTTCCAAGGNCATTGTGGGGT
CCCCCTANTTTGTT 3'

Protein sequence

NKYYNEKCQARKAAIAKTIREVCKVVSDVLKEVEVQEPRFISSLNERYEGLEVIPPTEFE
VVLYLNQMGVFNFVDDGSLPGCAVLKLSDGRKRSMSLWVEFITASGSARKIRSRFSD

FIGURE 15

**Mouse *Mab21* homolog sequence** from PCR product aligned with multiple cDNA sequences

DNA sequence

```
5' CAGGAGCCGCGGTTCATCAGCTCCCTCAATGAGATGGACAACCGCTACGAGGGCCTGG
AGGTTATCTCTCCCACCGAGTTCGAGGTGGTATACCTCAACCAGATGGGAGTCTTCAACT
TCGTGGACGACGGATCTCTGCCCGGCTGTGCAGTGCTCAAACTAAGCGATGGGCGGAAAC
GGACGATGTCTCTTTGGGTCGAGTTCATCACAGCGTCTGGCTACCTTTCTGCGCGCAAGA
TCCGCTCGCGTTTCCAGACACTAGTAGCCCAGGCGGTGGACAAGTGCAGCTACCGGGACG
TGGTCAAGATGATCGCCGACACTAGTGAGGTCAAGTTGCGCATCAGGGAGCGCTACGTGG
TGCAAATCACCCCAGCGTTCAAGTGCACCGGGATCTGGCCTCGCAGCGCGGCACACTGGC
CTATGCCCCACATCCCTGGCCCGGCCCCAATCGGGTGGCGGAGGTCAAGGCCGAAGGTT
TCAACTTGCTCTCCAAGGAGTGCTACTCGCTGACTGGCAAGCAGAGCTCCGCAGAAAGCG
ACGCCTGGGTGCTGCAGTTCGGTGAGGCGGAGAACCGCTTGCTGATGGGCGGCTGTAGAA
ACAAGTGCCTCTCGGTGCAGAAGACGCTGCGGGACCGGCACCTGGAGCTGCCTGGCCAGC
CGCTCAATAACTACCACATGAAGACGCTGCTGCTGTACGAGTGCGAGAAACACCCGAGGG
AAACGGACTGGGACGAGGCTTGCTTGGGCGACCGTCTGAACGGCATCCTGCTACAGCTCA
TCTCCTGCCTGCAGTGCCGCCGCTGCCCTCACTACTTTTTGCCCAACCTCGACCTCTTCC
AGGGTAAGCCCCACTCGGCCCTGGAGAGCGCTGCCAAGCAGACCTGGAGATTGGCCAGGG
AAATCCTCACCAATCCCAAAAGCTTGGACAAACTATAGAGTGCTGCCGACTGCGTGGAAA
GCAACATAAATGGGCATGCTCTCCCAGAACACACAACAACAGCAAAAACTCGAAACACAA
ACTTTTATGTAAATCACCTGAAAGAACGGGAGT 3'
```

Protein sequence

```
QEPRFISSLNEMDNRYEGLEVISPTEFEVVYLNQMGVFNFVDDGSLPGCAVLKLSDGRKR
TMSLWVEFITASGYLSARKIRSRFQTLVAQAVDKCSYRDVVKMIADTSEVKLRIRERYVV
QITPAFKCTGIWPRSAAHWPLPHIPWPGPNRVAEVKAEGFNLLSKECYSLTGKQSSAESD
AWVLQFGEAENRLLMGGCRNKCLSVQKTLRDRHLELPGQPLNNYHMKTLLLYECEKHPRE
TDWDEACLGDRLNGILLQLISCLQCRRCPHYFLPNLDLFQGKPHSALESAAKQTWRLARE
ILTNPKSLDKL
```

FIGURE 19A

Sera from Mouse

| | 1 | 2 | 3 | 4 | 5 | 6 | 7 | 8 | 9 | 10 | 11 | 12 |
|---|---|---|---|---|---|---|---|---|---|---|---|---|
| 1 | 0.764 | 0.835 | 0.929 | 0.941 | 0.837 | 0.905 | 0.958 | 1.069 | 0.912 | 0.694 | 0.944 | 1.107 |
| 2 | 0.734 | BLANK | 0.944 | 0.018 | 0.600 | -0.001 | 0.980 | 0.008 | 0.788 | -0.013 | 0.907 | 0.023 |
| 3 | 0.810 | BLANK | 0.833 | -0.020 | 0.930 | -0.017 | 0.933 | -0.006 | 0.796 | -0.012 | 0.783 | 0.024 |
| 4 | 0.852 | -0.027 | 0.832 | -0.016 | 0.773 | 0.013 | 0.716 | 0.034 | 0.788 | 0.086 | 0.779 | 0.094 |
| 5 | 0.716 | -0.031 | 0.818 | 0.009 | 0.635 | 0.020 | 0.648 | 0.057 | 0.898 | 0.083 | 0.921 | 0.069 |
| 6 | 0.793 | 0.860 | 0.771 | 0.780 | 0.869 | 0.811 | 0.902 | 1.031 | 0.721 | 1.477 | 0.895 | 0.586 |
| 7 | 0.759 | 0.796 | 0.686 | 0.678 | 0.740 | 1.115 | 0.872 | 1.026 | 0.795 | 1.736 | 0.709 | 0.591 |
| 8 | 0.761 | 0.736 | 0.745 | 1.147 | 0.784 | 0.856 | 0.862 | 0.686 | 0.708 | 2.214 | 0.928 | 0.875 |

ABSORBANCE AT 450 NM WAVELENGTH
*FIXED ANTIGEN CONCENTRATION THROUGHOUT
*SERIAL DILUTION ANTIBODY FOR ELISA

FIGURE 19B

Absorbance at 450 nm wavelength
*Fixed antigen concentration throughout
*Serial dilution of antibody for ELISA

| Odd no. row | Even no. row |
|---|---|
| 1/12800 | 1/100 |
| 1/6400 | Blank |
| 1/3200 | Blank |
| 1/1600 | pre-immune serum |
| 1/800 | pre-immune serum |
| 1/400 | 1/102400 |
| 1/200 | 1/51200 |
| 1/100 | 1/25600 |

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 125 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Met Ser Gly Gln Asn Ala Ala Val Thr Ser Tyr Gln Val Ser His Tyr
 1               5                  10                  15

Phe Asn Glu Arg Val Ala Thr Arg Lys Ser His Val His Lys Ala Ile
                20                  25                  30

Tyr Met Ile Ala Lys Ile Val Gln Glu Ile Leu Lys Glu Val Glu Ala
            35                  40                  45

Gln Glu Pro Arg Phe Ile Ser Thr Leu Ile Glu Asn Asn Gly Arg Tyr
50                  55                  60

Glu Gly Ile Ile Val His Ser Pro Cys Glu Tyr Glu Val Ile Leu Tyr
65                  70                  75                  80

Leu Asn Gln Met Gly Val Phe Asn Phe Val Asp Asp Gly Ser Ile Gln
                85                  90                  95

Gly Cys Ala Val Leu Lys Leu Ser Asp Gly Arg Lys Arg Ser Met Ser
            100                 105                 110

Leu Trp Val Glu Phe Ile Thr Ala Ser Gly Tyr Leu Ser
        115                 120                 125
```

(2) INFORMATION FOR SEQ ID NO:2:

(i) SEQUENCE CHARACTERISTICS:
      (A) LENGTH: 249 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

```
Glu Phe Ile Thr Ala Ser Gly Tyr Leu Ser Ala Arg Lys Ile Arg His
 1               5                  10                  15

Arg Phe Gln Asn Ile Val Ala Gln Val Leu Gln Thr Pro Gln Phe Ser
                20                  25                  30

Glu Tyr Cys Lys Leu Leu Gln Asp Asn Thr Asp Val Arg Val Arg Val
            35                  40                  45

Asp Asp Lys Tyr Thr Val Gln Ile Thr Cys Ala Phe Arg Cys Asn Gly
50                  55                  60

Ile Trp Pro Arg Ser Ala Ser His Trp Pro Leu Ala Gly Leu Pro Trp
65                  70                  75                  80

Pro Asn Thr Ala Leu Ala Asn Gln Thr Lys Ala Glu Gly Phe Asp Leu
                85                  90                  95

Thr Ser Arg Glu Thr Ala Ile Ser Thr Gln His Asn Asn Pro Asn Lys Gln
            100                 105                 110

Ala Ser Thr Met Glu Ala Asp Ala Trp Ala Met Lys Met His Gly Ala
```

```
            115                 120                 125
Glu Asn Met Leu Leu Thr Gly Gly Arg Arg Lys Thr Leu Ser Ile Leu
            130                 135                 140

Lys Cys Leu Arg Asp Ala His Met Asp Phe Pro Gly Thr Pro Val Thr
145                 150                 155                 160

Asn Tyr Ile Leu Lys Thr Leu Val Leu Tyr Glu Cys Glu Lys His Cys
                    165                 170                 175

Ser Glu Tyr Glu Trp Glu Asp Thr Asn Ile Gly Asp Arg Leu Val Gly
                180                 185                 190

Val Leu Leu Gln Leu Val Ser Cys Leu Gln Cys Arg Arg Cys Ala His
                195                 200                 205

Tyr Phe Leu Pro Ser Leu Asp Leu Leu Arg Ala Lys Pro Thr His Thr
210                 215                 220

Ile Glu His Ser Ala Lys Leu Thr Trp His Leu Val Arg Lys Leu Met
225                 230                 235                 240

Ile Asp Pro Asn Ala Leu Gln Thr Leu
                    245
```

(2) INFORMATION FOR SEQ ID NO:3:

(i) SEQUENCE CHARACTERISTICS:
        (A) LENGTH: 364 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Leu Gly His Asn Gln Asn Val Val Tyr Gln Val Asn Asn Tyr Phe
1               5                   10                  15

Asn Glu Lys Val Gln His Arg Lys Val Arg Val Thr Lys Thr Val Gln
                20                  25                  30

Arg Ile Ala Lys Val Val Gln Glu Ile Leu Lys Glu Val Glu Ala Gln
                35                  40                  45

Glu Pro Arg Phe Ile Asn Thr Leu Ser Glu Thr Thr Thr Gly Arg Phe
50                  55                  60

Asp Gly Ile Val Val His Ser Pro Ser Gly Tyr Glu Ala Val Leu Tyr
65                  70                  75                  80

Leu Asn Gln Met Gly Val Phe Asn Phe Val Asp Asp Gly Thr Ile Gln
                85                  90                  95

Gly Cys Ala Val Leu Lys Leu Ser Asp Gly Arg Lys Arg Ser Met Ser
                100                 105                 110

Leu Trp Val Glu Phe Ile Thr Ala Ser Gly Tyr Leu Ser Ala Arg Lys
                115                 120                 125

Ile Arg His Arg Phe Gln Asn Ile Val Ala Gln Val Leu Gln Thr Pro
                130                 135                 140

Gln Phe Ser Asp Tyr Cys Lys Leu Leu Gln Asp Asn Thr Asp Val Arg
145                 150                 155                 160

Val Arg Val Asp Asp Lys Tyr Thr Val Gln Ile Thr Cys Ala Phe Arg
                165                 170                 175

Cys Asn Gly Ile Trp Pro Arg Ser Ala Ser His Trp Pro Ile Ala Gly
                180                 185                 190

Leu Pro Trp Pro Asn Ala Ala Leu Ala Asn Gln Thr Lys Ala Glu Gly
                195                 200                 205

Phe Asp Leu Thr Ser Arg Glu Thr Ala Ile Thr Gln Gln Asn Asn Pro
```

-continued

```
            210                 215                 220
Asn Lys Gln Ala Ser Ser Met Glu Ala Asp Ala Trp Ala Met Lys Met
225                 230                 235                 240

His Gly Ala Glu Asn Met Leu Leu Thr Gly Gly Arg Arg Lys Thr Leu
                    245                 250                 255

Ser Ile Leu Lys Cys Leu Arg Asp Ala His Met Asp Phe Pro Gly Thr
                260                 265                 270

Pro Val Thr Asn Tyr Ile Leu Lys Thr Leu Val Leu Tyr Glu Cys Glu
            275                 280                 285

Lys His Cys Ser Glu Tyr Glu Trp Glu Asp Pro Asn Ile Gly Asp Arg
        290                 295                 300

Leu Val Gly Ile Leu Leu Gln Leu Val Ser Cys Leu Gln Cys Arg Arg
305                 310                 315                 320

Cys Ala His Tyr Phe Leu Pro Ser Leu Asp Leu Leu Arg Ser Lys Pro
                325                 330                 335

Val His Ser Ile Glu His Ser Ala Gln Leu Ala Trp His Leu Val Arg
            340                 345                 350

Lys Leu Met Ile Asp Pro Asn Ala Leu Gln Ser Leu
        355                 360

(2) INFORMATION FOR SEQ ID NO:4:

(i) SEQUENCE CHARACTERISTICS:
        (A) LENGTH: 359 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Ile Ala Ala Gln Ala Lys Leu Val Tyr His Leu Asn Lys Tyr Tyr
1               5                   10                  15

Asn Glu Lys Cys Gln Ala Arg Lys Ala Ala Ile Ala Lys Thr Ile Arg
                20                  25                  30

Glu Val Cys Lys Val Val Ser Asp Val Leu Lys Glu Val Glu Val Gln
            35                  40                  45

Glu Pro Arg Phe Ile Ser Ser Leu Asn Glu Met Asp Asn Arg Tyr Glu
        50                  55                  60

Gly Leu Glu Val Ile Ser Pro Thr Glu Phe Glu Val Val Leu Tyr Leu
65                  70                  75                  80

Asn Gln Met Gly Val Phe Asn Phe Val Asp Asp Gly Ser Leu Pro Gly
                85                  90                  95

Cys Ala Val Leu Lys Leu Ser Asp Gly Arg Lys Arg Ser Met Ser Leu
                100                 105                 110

Trp Val Glu Phe Ile Thr Ala Ser Gly Tyr Leu Ser Ala Arg Lys Ile
            115                 120                 125

Arg Ser Arg Phe Gln Thr Leu Val Ala Gln Ala Val Asp Lys Cys Ser
130                 135                 140

Tyr Arg Asp Val Val Lys Met Val Ala Asp Thr Ser Glu Val Lys Leu
145                 150                 155                 160

Arg Ile Arg Asp Arg Tyr Val Val Gln Ile Thr Pro Ala Phe Lys Cys
                165                 170                 175

Thr Gly Ile Trp Pro Arg Ser Ala Ala His Trp Pro Leu Pro His Ile
                180                 185                 190

Pro Trp Pro Gly Pro Asn Arg Val Ala Glu Val Lys Ala Glu Gly Phe
```

-continued

```
                195                 200                 205
Asn Leu Leu Ser Lys Glu Cys His Ser Leu Ala Gly Lys Gln Ser Ser
    210                 215                 220

Ala Glu Ser Asp Ala Trp Val Leu Gln Phe Ala Glu Ala Glu Asn Arg
225                 230                 235                 240

Leu Gln Met Gly Gly Cys Arg Lys Lys Cys Leu Ser Ile Leu Lys Thr
                245                 250                 255

Leu Arg Asp Arg His Leu Glu Leu Pro Gly Gln Pro Leu Asn Asn Tyr
                260                 265                 270

His Met Lys Thr Leu Val Ser Tyr Glu Cys Glu Lys His Pro Arg Glu
                275                 280                 285

Ser Asp Trp Asp Glu Ser Cys Leu Gly Asp Arg Leu Asn Gly Ile Leu
            290                 295                 300

Leu Gln Leu Ile Ser Cys Leu Gln Cys Arg Arg Cys Pro His Tyr Phe
305                 310                 315                 320

Leu Pro Asn Leu Asp Leu Phe Gln Gly Lys Pro His Ser Ala Leu Glu
                325                 330                 335

Asn Ala Ala Lys Gln Thr Trp Arg Leu Ala Arg Glu Ile Leu Thr Asn
                340                 345                 350

Pro Lys Ser Leu Glu Lys Leu
            355
```

(2) INFORMATION FOR SEQ ID NO:5:

(i) SEQUENCE CHARACTERISTICS:
        (A) LENGTH: 311 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Gln Glu Pro Arg Phe Ile Ser Ser Leu Asn Glu Met Asp Asn Arg Tyr
1               5                   10                  15

Glu Gly Leu Glu Val Ile Ser Pro Thr Glu Phe Glu Val Val Tyr Leu
                20                  25                  30

Asn Gln Met Gly Val Phe Asn Phe Val Asp Asp Gly Ser Leu Pro Gly
                35                  40                  45

Cys Ala Val Leu Lys Leu Ser Asp Gly Arg Lys Arg Thr Met Ser Leu
50                  55                  60

Trp Val Glu Phe Ile Thr Ala Ser Gly Tyr Leu Ser Ala Arg Lys Ile
65                  70                  75                  80

Arg Ser Arg Phe Gln Thr Leu Val Ala Gln Ala Val Asp Lys Cys Ser
                85                  90                  95

Tyr Arg Asp Val Val Lys Met Ile Ala Asp Thr Ser Glu Val Lys Leu
                100                 105                 110

Arg Ile Arg Glu Arg Tyr Val Val Gln Ile Thr Pro Ala Phe Lys Cys
                115                 120                 125

Thr Gly Ile Trp Pro Arg Ser Ala His Trp Pro Leu Pro His Ile
130                 135                 140

Pro Trp Pro Gly Pro Asn Arg Val Ala Glu Val Lys Ala Glu Gly Phe
145                 150                 155                 160

Asn Leu Leu Ser Lys Glu Cys Tyr Ser Leu Thr Gly Lys Gln Ser Ser
                165                 170                 175

Ala Glu Ser Asp Ala Trp Val Leu Gln Phe Gly Glu Ala Glu Asn Arg
```

-continued

```
                    180                 185                 190
Leu Leu Met Gly Gly Cys Arg Asn Lys Cys Leu Ser Val Gln Lys Thr
            195                 200                 205

Leu Arg Asp Arg His Leu Glu Leu Pro Gly Gln Pro Leu Asn Asn Tyr
    210                 215                 220

His Met Lys Thr Leu Leu Leu Tyr Glu Cys Glu Lys His Pro Arg Glu
225                 230                 235                 240

Thr Asp Trp Asp Glu Ala Cys Leu Gly Asp Arg Leu Asn Gly Ile Leu
                245                 250                 255

Leu Gln Leu Ile Ser Cys Leu Gln Cys Arg Arg Cys Pro His Tyr Phe
            260                 265                 270

Leu Pro Asn Leu Asp Leu Phe Gln Gly Lys Pro His Ser Ala Leu Glu
    275                 280                 285

Ser Ala Ala Lys Gln Thr Trp Arg Leu Ala Arg Glu Ile Leu Thr Asn
290                 295                 300

Pro Lys Ser Leu Asp Lys Leu
305                 310
```

(2) INFORMATION FOR SEQ ID NO:6:

(i) SEQUENCE CHARACTERISTICS:
        (A) LENGTH: 319 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Leu Gly His Asn Gln Asn Val Val Tyr Gln Val Asn Asn Tyr Phe
1               5                   10                  15

Asn Glu Lys Val Gln His Arg Lys Val Arg Val Thr Lys Thr Val Gln
            20                  25                  30

Arg Ile Ala Lys Val Val Gln Glu Ile Leu Lys Glu Val Glu Ala Gln
        35                  40                  45

Glu Pro Arg Phe Ile Asn Thr Leu Ser Glu Thr Thr Thr Gly Arg Phe
    50                  55                  60

Asp Gly Ile Val Val His Ser Pro Ser Glu Tyr Glu Ala Val Leu Tyr
65                  70                  75                  80

Leu Asn Gln Met Gly Val Phe Asn Phe Val Asp Asp Gly Thr Ile Gln
                85                  90                  95

Gly Cys Ala Val Leu Lys Leu Ser Asp Gly Arg Lys Arg Ser Met Ser
            100                 105                 110

Phe Gly Ser Ser Ser Leu Leu Leu Asp Ile Tyr Gln Leu Ala Arg
        115                 120                 125

Phe Ala Thr Asp Ser Lys Ile Leu Trp Leu Lys Phe Tyr Lys Leu His
    130                 135                 140

Asn Ser Gly Leu Pro Trp Pro Asn Ala Ala Leu Ala Asn Gln Thr Lys
145                 150                 155                 160

Ala Glu Gly Phe Asp Leu Thr Ser Arg Glu Thr Ala Ile Thr Gln Gln
                165                 170                 175

Asn Asn Pro Asn Lys Gln Ala Ser Ser Met Glu Ala Asp Ala Trp Ala
            180                 185                 190

Met Lys Met His Gly Ala Glu Asn Met Leu Leu Thr Gly Gly Arg Arg
        195                 200                 205

Lys Thr Leu Ser Ile Leu Lys Cys Leu Arg Asp Ala His Met Asp Phe
```

```
              210                 215                  220
Pro Gly Thr Pro Val Thr Asn Tyr Ile Leu Lys Thr Leu Val Leu Tyr
225                 230                 235                 240

Glu Cys Glu Lys His Cys Ser Glu Tyr Glu Trp Glu Asp Pro Asn Ile
                245                 250                 255

Gly Asp Arg Leu Val Gly Ile Leu Leu Gln Leu Val Ser Cys Leu Gln
            260                 265                 270

Cys Arg Arg Cys Ala His Tyr Phe Leu Pro Ser Leu Asp Leu Leu Arg
        275                 280                 285

Ser Lys Pro Val His Ser Ile Glu His Ser Ala Gln Leu Ala Trp His
290                 295                 300

Leu Val Arg Lys Leu Met Ile Asp Pro Asn Ala Leu Gln Ser Leu
305                 310                 315
```

(2) INFORMATION FOR SEQ ID NO:7:

(i) SEQUENCE CHARACTERISTICS:
        (A) LENGTH: 2585 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

```
GAATTCATAA CGGCTTCGGG ATATCTTTCG GCTCGAAAAA TTCGTCACCG ATTCCAAAAC      60
ATTGTTGCCC AAGTTCTCCA GACTCCACAA TTTAGGTAAT TCAAAAAAAG CACTAATCAC     120
GTTTTTGTAA AACTTCAGCG AATACTGTAA ACTTCTACAA GACAACACTG ATGTACGAGT     180
AAGAGTGGAT GATAAGTACA CGGTTCAAAT CACTTGTGCA TTTCGATGTA ATGGAATTTG     240
GCCTAGATCA GCCAGTCATT GGCCTTTAGC TGGTCTACCA TGGCCGAATA CGGCATTGGC     300
TAATCAAACA AAAGCAGAAG GATTCGATCT GACTAGTCGA GAAACTGCAA TTACTCAGCA     360
TAACAATCCG AATAAACAGG CTAGCACAAT GGAAGCGGAC GCTTGGGCAA TGAAGATGCA     420
CGGAGCCGAG AACATGCTAC TGACTGGAGG TAGACGGAAA ACTTTGAGCA TTCTGAAATG     480
CCTTCGAGAT GCTCATATGG ACTTTCCTGG AACACCAGTA ACAAACTATA TCCTGAAGAC     540
CTTGGTTCTA TACGAATGTG AGAAGCACTG TAGTGAGTAT GAATGGGAAG ACACAAACAT     600
TGGAGATCGC CTTGTCGGGT AAGTTGGNCC TCCAGGGANN CNAGCAAANN CAAGGCNGGA     660
AAAGGGCGGG GNNGACCCCC AATGGGAAGG NGGNACGNCT NGGGCCCATT GGGNGGNTGC     720
GNGGGAACCN CGAAGAAAAA TTCCTCCCTG GCCTGGGGGG NNAGANAAGG AAGAACNTNT     780
GANCCAATTC TTGAGGAATG CCCAACGNAG ATGCTCCAGG GTGGAGACGT TCCCTGGGGA     840
CACCCAGTTA GCGGACCTAA TATCGCTGGA AAACTCNTTG TTCTGTGCCG AATGTGAGAA     900
AGCCCCTGTA GTGAGTATGA AATGGGGAAG GACACACANAAC ATTGGAGATC GTCTCGTTGG     960
TGAGTATTTC AATAATTTGA AATTAAAGTA GTGTTGGCTA TCACAACATT TTTTCATTCT    1020
AAAATGTACT CTTCTTCTGA TGACAATTCT GTGACTTGTC GTTTTTAACT TCCACAGAAG    1080
CCGTTAAAAA AGCATTGCGT GACAAAAGAA GAACGACGCC TTCGTTTTTT CTTGCTCCTG    1140
CTTCTATCCA TCTTCCTAGG TGCTGCCCTC CCTATTTTTT CTTTCTATTT CTGAGAGCCT    1200
CGGCATGCAT TCCTAATGGA TTCCTTCGTG TTCAACCGGA AAGTGCCTAC ACGGAAAGGA    1260
AAAAAAAACG GAGGGAGTTT GTTCTCTTTG TATATTGCAT ATACGTTATA TTCATCTTAT    1320
TTTCCCTCCT AATCAACTAG TGGCGTGAAA TCTTTGAAGA AGTGAAGAGC AGACAGTGTG    1380
```

-continued

| | |
|---|---|
| AAAATGAAGG AGGGCATAGA CAAAAGATGT CATACCGAAT TAGGTTTTGC GGNCTNNCAC | 1440 |
| CCAGNGAGGA AACGATTTCA ATTCATNGAA AAACAAACGT TTGAAACTGA CTATGAGGGG | 1500 |
| TTGGGCAGAA AAAAAGATT TGGATTCTTG ATCAAGAACT GGAACCGAAA AACGACTTTC | 1560 |
| AGGTGTTCTC CTACAACTTG TCAGCTGTCT CCAATGTCGC CGATGTGCTC ATTATTTCCT | 1620 |
| CCCATCGTTG GATTTACTCC GTGCAAAACC AACCCACACA ATCGAACATT CTGCCAAACT | 1680 |
| CACCTGGCAC CTTGTTCGCA AACTTATGAT TGACCCGAAT GCTTTGCAAA CTTTATGATT | 1740 |
| GATACCCCTT TTTCTTTTTC TCTTCACTCT GTTCTCTTTT CATTCTTTCT CACCGATTTG | 1800 |
| ATACAGGTAT TTCCTTCTTT TTTTCTCATA ATAAATTTTT TTGTACCCTA ATTACCTGAG | 1860 |
| CACACTGTTT CTTGTAGTTT GGATCAGATT CGTTCGCATC GAAGAATAGA TCTGAAGCGG | 1920 |
| TCACAGATAG CGTTCCAGGA ACAACGACTC CAGGGACGAT GAGTTTGGCA GCAGTGGAGA | 1980 |
| AGCACGCACT TTCTGTAATT AGGTATTTTA AAAGCATCCA ATCTCAGGTT GCTCACTCTT | 2040 |
| TCTCTTCCCT CAGGAACCCC ATAAAAACGT TCACTGCTAA ATATAGAATA TATCCTTTAA | 2100 |
| ATGGTGCTCC AAAGGCATCA TCATTAATCC ATTTCTTTCT TCCCAAACTA CTGCGGNCTT | 2160 |
| GTCCTCATAG ATCATCGTCG TTTTGACAAA ATGGCATGAG CAATTAGAAG TAAGCTCCGC | 2220 |
| TCCACTCTCA GGTGCCTTNT CTCATTTNNN NNGGAAAAGG AAGGAGGGGG GGGAAGGGGG | 2280 |
| TTCTTAAAGA GATTCACTTC TTGGGGTGAG TGGGGCCGAA AAATGAGAAA GCGAATGTTT | 2340 |
| GTANNCNGAG NNGNACCCAT TCCCGAACAG AAAGAGATTG GGAAAGGGTT NCTGAGTGAT | 2400 |
| GAATTACCGA AACAACTGAC ACTCAACCAC AAAAGTTAGN TGCGATTTTG AAGAAGAAAC | 2460 |
| AACGAGGAGT GTGAAACTGA AACTATAGTA AACTGGAATC TGAGACTCCC GTGGAACANC | 2520 |
| CTAGGAAGCT TAATAATCTG TAGGCACCCA TACCAACTGT CACCAAAATA ACATCTGTCG | 2580 |
| AATTC | 2585 |

(2) INFORMATION FOR SEQ ID NO:8:

(i) SEQUENCE CHARACTERISTICS:
        (A) LENGTH: 249 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Glu Phe Ile Thr Ala Ser Gly Tyr Leu Ser Ala Arg Lys Ile Arg His
 1               5                  10                  15

Arg Phe Gln Asn Ile Val Ala Gln Val Leu Gln Thr Pro Gln Phe Ser
             20                  25                  30

Glu Tyr Cys Lys Leu Leu Gln Asp Asn Thr Asp Val Arg Val Arg Val
         35                  40                  45

Asp Asp Lys Tyr Thr Val Gln Ile Thr Cys Ala Phe Arg Cys Asn Gly
     50                  55                  60

Ile Trp Pro Arg Ser Ala Ser His Trp Pro Leu Ala Gly Leu Pro Trp
 65                  70                  75                  80

Pro Asn Thr Ala Leu Ala Asn Gln Thr Lys Ala Glu Gly Phe Asp Leu
                 85                  90                  95

Thr Ser Arg Glu Thr Ala Ile Thr Gln His Asn Asn Pro Asn Lys Gln
            100                 105                 110

Ala Ser Thr Met Glu Ala Asp Ala Trp Ala Met Lys Met His Gly Ala
        115                 120                 125
```

```
Glu Asn Met Leu Leu Thr Gly Gly Arg Arg Lys Thr Leu Ser Ile Leu
    130                 135                 140

Lys Cys Leu Arg Asp Ala His Met Asp Phe Pro Gly Thr Pro Val Thr
145                 150                 155                 160

Asn Tyr Ile Leu Lys Thr Leu Val Leu Tyr Glu Cys Glu Lys His Cys
                165                 170                 175

Ser Glu Tyr Glu Trp Glu Asp Thr Asn Ile Gly Asp Arg Leu Val Gly
            180                 185                 190

Val Leu Leu Gln Leu Val Ser Cys Leu Gln Cys Arg Arg Cys Ala His
                195                 200                 205

Tyr Phe Leu Pro Ser Leu Asp Leu Leu Arg Ala Lys Pro Thr His Thr
        210                 215                 220

Ile Glu His Ser Ala Lys Leu Thr Trp His Leu Val Arg Lys Leu Met
225                 230                 235                 240

Ile Asp Pro Asn Ala Leu Gln Thr Leu
                245
```

(2) INFORMATION FOR SEQ ID NO:9:

(i) SEQUENCE CHARACTERISTICS:
        (A) LENGTH: 421 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

```
ATTTTTGGAC TCTACGATAA TTTGCATAGC AACCAAACAG GCAAGGATGT CAGGCCAGAA     60

TGCTGCCGTT ACTTCCTACC AAGTATCGCA TTATTTCAAC GAAAGGGTAG CCACTCGAAA    120

AAGTCATGTA CACAAGGCAA TCTATATGAT TGCTAAAATT GTGCAAGAAA TCCTTAAAGA    180

AGTTGAAGCA CAGGAACCTC GATTCATTTC TACACTCATT GAAAATAATG GTCGATATGA    240

AGGGATTATA GTTCATTCAC CGTGCGAATA TGAAGTAATC CTATACCTCA ATCAAATGGG    300

AGTTTTCAAT TTCGTCGATG ATGGCTCTAT TCAAGGATGT GCAGTACTAA AATTAAGTGA    360

TGGTAGAAAA CGATCAATGT CATTATGGGT GGAATTTATT ACCGCCAGCG GCTATCTGTC    420

A                                                                   421
```

(2) INFORMATION FOR SEQ ID NO:10:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Met Ser Gly Gln Asn Ala Ala Val Thr Ser Tyr Gln Val Ser His Tyr
1               5                   10                  15

Phe Asn Glu Arg Val Ala Thr Arg Lys Ser His Val His Lys Ala Ile
            20                  25                  30

Tyr Met Ile Ala Lys Ile Val Gln Glu Ile Leu Lys Glu Val Glu Ala
            35                  40                  45

Gln Glu Pro Arg Phe Ile Ser Thr Leu Ile Glu Asn Asn Gly Arg Tyr
        50                  55                  60

Glu Gly Ile Ile Val His Ser Pro Cys Glu Tyr Glu Val Ile Leu Tyr
```

-continued

```
65                   70                  75                  80
Leu Asn Gln Met Gly Val Phe Asn Phe Val Asp Asp Gly Ser Ile Gln
                         85                  90                  95
Gly Cys Ala Val Leu Lys Leu Ser Asp Gly Arg Lys Arg Ser Met Ser
                100                 105                 110
Leu Trp Val Glu Phe Ile Thr Ala Ser Gly Tyr Leu Ser
        115                 120                 125
```

(2) INFORMATION FOR SEQ ID NO:11:

(i) SEQUENCE CHARACTERISTICS:
        (A) LENGTH: 1278 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

```
CTTCATCATC ATCGAAAAAA GAACACACAC ACGCATATCT GTTTGTGTGC ATTTTTTCCC     60
GGTTTCCGCG TGTCCAACAT GCTAGGACAT AACCAGAACG TTGTTTATCA GGTGAATAAC    120
TATTTCAACG AAAAGTTCA ACATCGTAAA GTTCGTGTCA CAAAAACAGT ACAAAGAATC    180
GCCAAAGTGG TACAAGAAAT ATTGAAAGAA GTTGAAGCAC AAGAACCTCG ATTCATTAAT    240
ACATTAAGTG AAACTACAAC TGGAAGATTC GATGGAATTG TGGTACATTC TCCATCCGAG    300
TATGAGGCAG TGCTATACCT CAACCAGATG GGTGTCTTCA ATTTTGTTGA CGACGGAACA    360
ATTCAAGGAT GTGCAGTTCT CAAACTAAGT GATGGTCGGA AAAGATCAAT GTCCCTTTGG    420
GTCGAGTTCA TTACTGCTTC TGGATATTTA TCAGCTCGCA AGATTCGCCA CCGATTCCAA    480
AATATTGTGG CTCAAGTTTT ACAAACTCCA CAATTCAGTG ATTACTGTAA GTTGCTACAA    540
GATAACACTG ATGTGAGAGT TCGAGTAGAT ACAAGTACA CCGTTCAAAT TACTTGTGCA    600
TTTCGATGCA ACGGAATCTG GCCTCGATCA GCGAGTCATT GGCCAATTGC AGGACTTCCA    660
TGGCCGAACG CCGCGTTGGC GAATCAGACA AAAGCCGAGG GATTCGACTT GACGAGTCGT    720
GAAACTGCAA TCACTCAACA AAATAATCCG AATAAGCAAG CGAGCAGTAT GGAAGCCGAT    780
GCCTGGGCAA TGAAGATGCA TGGTGCAGAG AACATGTTAC TAACTGGAGG TCGGCGGAAG    840
ACATTGAGCA TTCTGAAATG TCTTCGAGAT GCTCACATGG ACTTTCCGGG AACACCAGTA    900
ACAAACTACA TACTGAAGAC ATTGGTATTG TACGAATGTG AGAAGCACTG TAGTGAATAC    960
GAATGGGAAG ATCCAAATAT CGGAGATCGC CTTGTCGGAA TTCTTCTACA ACTAGTCAGC   1020
TGCCTCCAAT GTCGTCGCTG TGCTCACTAT TTCCTTCCAT CTTTGGATCT TTTACGTTCA   1080
AAACCAGTCC ATTCCATTGA ACATTCCGCC CAACTCGCTT GGCATCTCGT TCGCAAACTA   1140
ATGATCGACC CAAATGCTTT GCAAAGTTTG TAATTTTTGA TTATCAATTC CCTCAAACTC   1200
TTTCTCACTC AACTACTGAT ACAGTTCATA CTTATAAATA AATTATTTTC TCCCAAAAAA   1260
AAAAAAAAAA AAAAAAAA                                                  1278
```

(2) INFORMATION FOR SEQ ID NO:12:

(i) SEQUENCE CHARACTERISTICS:
        (A) LENGTH: 364 amino acids
        (B) TYPE: amino acid
        (C) STRANDEDNESS: single
        (D) TOPOLOGY: linear (ii) MOLECULE TYPE: protein -continued (xi) SEQUENCE DESCRIPTION: SEQ ID NO:12:

| | | | | | | | | | | | | | | |
|---|---|---|---|---|---|---|---|---|---|---|---|---|---|---|
|Met|Leu|Gly|His|Asn|Gln|Asn|Val|Val|Tyr|Gln|Val|Asn|Asn|Tyr|Phe|
|1| | | |5| | | | |10| | | | |15|

Asn Glu Lys Val Gln His Arg Lys Val Arg Val Thr Lys Thr Val Gln
           20                   25               30

Arg Ile Ala Lys Val Val Gln Glu Ile Leu Lys Glu Val Glu Ala Gln
    35                   40               45

Glu Pro Arg Phe Ile Asn Thr Leu Ser Glu Thr Thr Gly Arg Phe
50                   55                 60

Asp Gly Ile Val Val His Ser Pro Ser Glu Tyr Glu Ala Val Leu Tyr
65                  70              75             80

Leu Asn Gln Met Gly Val Phe Asn Phe Val Asp Asp Gly Thr Ile Gln
           85               90                95

Gly Cys Ala Val Leu Lys Leu Ser Asp Gly Arg Lys Arg Ser Met Ser
      100              105             110

Leu Trp Val Glu Phe Ile Thr Ala Ser Gly Tyr Leu Ser Ala Arg Lys
     115              120            125

Ile Arg His Arg Phe Gln Asn Ile Val Ala Gln Val Leu Gln Thr Pro
130                 135             140

Gln Phe Ser Asp Tyr Cys Lys Leu Leu Gln Asp Asn Thr Asp Val Arg
145             150             155         160

Val Arg Val Asp Asp Lys Tyr Thr Val Gln Ile Thr Cys Ala Phe Arg
          165            170            175

Cys Asn Gly Ile Trp Pro Arg Ser Ala Ser His Trp Pro Ile Ala Gly
      180             185            190

Leu Pro Trp Pro Asn Ala Ala Leu Ala Asn Gln Thr Lys Ala Glu Gly
     195              200            205

Phe Asp Leu Thr Ser Arg Glu Thr Ala Ile Thr Gln Gln Asn Asn Pro
210                 215             220

Asn Lys Gln Ala Ser Ser Met Glu Ala Asp Ala Trp Ala Met Lys Met
225             230             235         240

His Gly Ala Glu Asn Met Leu Leu Thr Gly Gly Arg Arg Lys Thr Leu
      245             250            255

Ser Ile Leu Lys Cys Leu Arg Asp Ala His Met Asp Phe Pro Gly Thr
      260             265            270

Pro Val Thr Asn Tyr Ile Leu Lys Thr Leu Val Leu Tyr Glu Cys Glu
     275              280            285

Lys His Cys Ser Glu Tyr Glu Trp Glu Asp Pro Asn Ile Gly Asp Arg
290                 295             300

Leu Val Gly Ile Leu Leu Gln Leu Val Ser Cys Leu Gln Cys Arg Arg
305             310             315         320

Cys Ala His Tyr Phe Leu Pro Ser Leu Asp Leu Leu Arg Ser Lys Pro
         325           330            335

Val His Ser Ile Glu His Ser Ala Gln Leu Ala Trp His Leu Val Arg
         340           345           350

Lys Leu Met Ile Asp Pro Asn Ala Leu Gln Ser Leu
355                 360

(2) INFORMATION FOR SEQ ID NO:13:

(i) SEQUENCE CHARACTERISTICS:
        (A) LENGTH: 2770 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

```
GAATTCCACA ATAAGGTAAT TAGATTTAGA AGTACTCAGT CACTTTAAGT GGATAAATGT      60
ATTAGTTAAA ACTTTAGGGT TTGCTTTTTT GCTGTTTAGA TCAAAGTTTT TTCTGATTCT     120
TCTGTCCTCA TTGTGAACAT AACCGTGTAG TTGAAACAGT CAAACTTATT TTTGTAATGT     180
ATGTTATTGT GTGATGCAGT TTTTTGCTTC TGTCTCCAAT ATTAAACCAT TTTCCTAATA     240
CTTGTTTCTC TCTCTGCGTG TTGTATTGTT GGTAGTCATT ATATGTTGGT GATACATCTG     300
CACACTCACC CCGGACACAC ACTCAGCACA CTTTTCCTCC ATTTGATTAA CAGTGCTGCA     360
CACACAATGA TTACGGGAAA GCSSAWMWAA WKRMGGAAAR GKGTGCTTAK TKTGWSTMCK     420
GGRWGAGCTT TGCTGGGTCT CAGCGCAACT TTTGTTTTTT ATTCCTGAGA AGGTGATCTC     480
TCCATGCGGT TCTCTCACAC AAGGATTCTT TAAAAGAGGA AGAGAGACAA GCAGAGGGGG     540
GAGGACAGTC TTTCACTTTA AGAACGGCTG GGCTCAAAGA TAAAAGGAAG GGAAAAGCAG     600
CAGCAGCAGC AGCAGCAGCA GCAGCAGCAG CAGCAGCAGC AGCAGCAGCA GCAGCAGCAG     660
GGAAACCAAC GCTGCAGCAC TTCCGAAAGG CATTTTTGAT CCATTTCTGA GTGTTGCGGC     720
CCGTTTCTCC ACCGAAGTTG GCTCCAGCTC TAGCAGCCGC ATTGGATCCC ACAGCTTACT     780
GCGAGACTCC GGTGTACAAT CCGGATCTCT GCCCCAACAT GATTGCGGCC CAGGCCAAGC     840
TGGTCTACCA TCTGAATAAA TACTACAACG AAAAATGCCA AGCCAGGAAA GCTGCCATTG     900
CCAAAACTAT CCGGGAAGTC TGCAAAGTAG TTTCCGACGT ACTGAAGGAA GTGGAAGTGC     960
AGGAGCCGCG GTTCATCAGC TCTCTCAACG AGATGGACAA TCGCTACGAG GGCCTCGAGG    1020
TCATCTCCCC CACCGAATTT GAAGTGGTGC TTTATCTCAA CCAAATGGGG GTGTTCAACT    1080
TCGTGGACGA TGGCTCACTG CCCGGCTGCG CGGTGCTGAA GTTGAGCGAC GGGCGCAAGA    1140
GGAGCATGTC CCTCTGGGTG GAATTCATTA CCGCCTCCGG CTACCTCTCG GCGCGCAAAA    1200
TCCGGTCCAG GTTTCAGACG CTGGTGGCTC AAGCGGTAGA CAAATGTAGC TACCGGGATG    1260
TGGTAAAGAT GGTGGCAGAC ACCAGCGAAG TGAAACTGAG AATCCGAGAT AGGTACGTGG    1320
TGCAGATCAC GCCGGCCTTT AAATGCACCG GGATCTGGCC GAGGAGTGCT GCCCACTGGC    1380
CACTTCCCCA CATCCCCTGG CCGGGACCCA ACCGGGTGGC GGAGGTCAAG GCGGAAGGTT    1440
TCAATCTCTT GTCCAAGGAG TGCCACTCCT TGGCCGGCAA GCAGAGCTCG GCGGAGAGCG    1500
ACGCCTGGGT GCTGCAGTTC GCGGAGGCAG AGAACAGACT GCAGATGGGG GGCTGCAGAA    1560
AGAAGTGCCT CTCCATCCTC AAAACCTTAA GGGATCGTCA CCTTGAACTG CCGGGCCAGC    1620
CCTTGAACAA TTACCATATG AAGACTCTGG TTTCCTACGA GTGTGAAAAG CATCCCCGAG    1680
AGTCGGACTG GGACGAGTCT TGCCTGGGTG ATCGGCTGAA CGGGATTTTG CTGCAACTTA    1740
TCTCCTGCCT GCAGTGCCGG CGGTGTCCCC ACTACTTTCT ACCGAACTTA GATCTGTTTC    1800
AAGGCAAACC TCACTCAGCT CTGGAAAACG CTGCCAAACA AACGTGGCGA CTGGCAAGAG    1860
AGATCCTGAC CAACCCGAAA AGTTTGGAAA AACTTTAGAG GATGATTTAA TCAAGAGCCG    1920
AAATTATTAC CCTTCTCAAA GTCCTTATTA AGTGTAAACT TCTGTTCAAT TCCTAATATT    1980
CCACTCCGCA GTGCAAACAA TCTCTTCCTT TAAAAAGGAA TAATAATACA ATATTTAAAC    2040
ATCATCTCCC CACCCCCACA AGGGGAGAAA AAGTAGGGGA AGCGGATGGA GAAAAACCCA    2100
AAGCCACTAG TATTAGAAGA CTTCTTTCCA CACGATTTCC TATCTCCCTT GAAAAGTACA    2160
CCGTAACACT CCGTAAACAG CCCAGCTGTA ACGCCAGACC GAGACGAACA CTCTGCCTAA    2220
```

-continued

```
CTATCAAAGG ATTATAGCAA TCCTGGTGAT TTAGGTGCAT CTGTCTGTGA GTAAACACGA      2280

TTTGGATATG CCATCTGAAA GAAACTGTAA TGTATATTTT GATTTGTAAC AAATATTGTG      2340

ATCTCACATT GTCTTTGAAA GTGTGGATGT TGGTGTTTTG TGATTTGGTG AACAGAACTT      2400

AAATTGCCAT TCTGGATACT TCCAGACATT TTCCACTAAC AAAGATATCA TTTAAAGGTA      2460

GATTTCTTCC TGGTACTTTT ATCTGTCTTT GAAAGTGTCT GAACTTTAAA AAGTTTACAT      2520

TTTGTTTCAA ATATTGCTTG TTCTATTTCT AACATTCCAT AAATATACTT GAAATGTTAT      2580

TTAAATATAT TCAAAGAAAT TTGAATTCAG CTTATATAAT AACGCTTGAA TATCTGAATT      2640

ATATATTTGA AAAATGCACT TGAAATACAC TGGATAATTA CTTTTGTGAT TTAGATTTTA      2700

ATTTGTTGCT GGTTTTTATT TAATTAGATG GTAATAAATG AAGTAAAATA AAAAAAAAA      2760

AAAGGAATTC                                                             2770
```

(2) INFORMATION FOR SEQ ID NO:14:

(i) SEQUENCE CHARACTERISTICS:
        (A) LENGTH: 359 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Met Ile Ala Ala Gln Ala Lys Leu Val Tyr His Leu Asn Lys Tyr Tyr
1               5                   10                  15

Asn Glu Lys Cys Gln Ala Arg Lys Ala Ala Ile Ala Lys Thr Ile Arg
            20                  25                  30

Glu Val Cys Lys Val Val Ser Asp Val Leu Lys Glu Val Glu Val Gln
        35                  40                  45

Glu Pro Arg Phe Ile Ser Ser Leu Asn Glu Met Asp Asn Arg Tyr Glu
    50                  55                  60

Gly Leu Glu Val Ile Ser Pro Thr Glu Phe Glu Val Val Leu Tyr Leu
65                  70                  75                  80

Asn Gln Met Gly Val Phe Asn Phe Val Asp Asp Gly Ser Leu Pro Gly
                85                  90                  95

Cys Ala Val Leu Lys Leu Ser Asp Gly Arg Lys Arg Ser Met Ser Leu
            100                 105                 110

Trp Val Glu Phe Ile Thr Ala Ser Gly Tyr Leu Ser Ala Arg Lys Ile
        115                 120                 125

Arg Ser Arg Phe Gln Thr Leu Val Ala Gln Ala Val Asp Lys Cys Ser
    130                 135                 140

Tyr Arg Asp Val Val Lys Met Val Ala Asp Thr Ser Glu Val Lys Leu
145                 150                 155                 160

Arg Ile Arg Asp Arg Tyr Val Val Gln Ile Thr Pro Ala Phe Lys Cys
                165                 170                 175

Thr Gly Ile Trp Pro Arg Ser Ala Ala His Trp Pro Leu Pro His Ile
            180                 185                 190

Pro Trp Pro Gly Pro Asn Arg Val Ala Glu Val Lys Ala Glu Gly Phe
        195                 200                 205

Asn Leu Leu Ser Lys Glu Cys His Ser Leu Ala Gly Lys Gln Ser Ser
    210                 215                 220

Ala Glu Ser Asp Ala Trp Val Leu Gln Phe Ala Glu Ala Glu Asn Arg
225                 230                 235                 240

Leu Gln Met Gly Gly Cys Arg Lys Lys Cys Leu Ser Ile Leu Lys Thr
```

```
                    245                 250                 255
Leu Arg Asp Arg His Leu Glu Leu Pro Gly Gln Pro Leu Asn Asn Tyr
                260                 265                 270

His Met Lys Thr Leu Val Ser Tyr Glu Cys Glu Lys His Pro Arg Glu
        275                 280                 285

Ser Asp Trp Asp Glu Ser Cys Leu Gly Asp Arg Leu Asn Gly Ile Leu
    290                 295                 300

Leu Gln Leu Ile Ser Cys Leu Gln Cys Arg Arg Cys Pro His Tyr Phe
305                 310                 315                 320

Leu Pro Asn Leu Asp Leu Phe Gln Gly Lys Pro His Ser Ala Leu Glu
                325                 330                 335

Asn Ala Ala Lys Gln Thr Trp Arg Leu Ala Arg Glu Ile Leu Thr Asn
                340                 345                 350

Pro Lys Ser Leu Glu Lys Leu
        355
```

(2) INFORMATION FOR SEQ ID NO:15:

(i) SEQUENCE CHARACTERISTICS:
        (A) LENGTH: 503 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

```
ACCATCTGAA TAAATACTAC AACGAAAAAT GCCAAGCCAG GAAAGCTGCC ATTGCCAAAA    60
CTATCCGGGA AGTCTGCAAA GTAGTTTCCG ACGTACTGAA GGAAGTGGAA GTGCAGGAGC   120
CGCGGTTCAT CAGCTCTCTC AACGAGATGG ACAATCGCTA CGAGGGCCTC GAGGTCATCC   180
CCCCCACCGA ATTTGAAGTG GTGCTTTATC TCAACCAAAT GGGGGTGTTC AACTTCGTGG   240
ACGATGGCTC ACTGCCCGGC TGCGCGGTGC TGAAGTTGAG CGACGGGCGC AAGAGGAGCA   300
TGTCCCTCTG GGTGGAATTC ATTACCGCCT CCGGCTAACC TCTCGGCGCG CAAAATCCGG   360
TCCAGGTTTC AGACGCTGGT GGCTCAAGCG GTAGACAAAT GTTAGCTACC GGGATGTGGT   420
AAAGATNGTG GCAGACACCA GCGAAGTGAA ACTNAGAATC CGAGATAGGT ACGTTGTNCA   480
GATCAAGTCC GNCTTTTAAT TCT                                          503
```

(2) INFORMATION FOR SEQ ID NO:16:

(i) SEQUENCE CHARACTERISTICS:
        (A) LENGTH: 346 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:

```
TTTTTTTTTT ATTTTACTTC ATTTATTACC ATCTAATTAA ATAAAAACCA GCAACAAATT    60
AAAATCTAAA TCACAAAAGT AATTATCCAG TGTATTTCAA GTGCATTTTT CAAATATATA   120
ATTCAGATAT TCAAGCGTTA TTATATAAGC TGAATTCAAA TTTCTTTGAA TATATTTAAA   180
TAACATTTCA AGTATATTTA TGGAATGTTA GAAATAGAAC AAGCAATATT TGAAACAAAA   240
TGTAAACTTT TTAAAGTTCA GACACTTTCA AAGACAGATA AAAGTACCNG GGAGAAATCT   300
ACCTTTAAAT GATATCTTTG TTAGTGGGAA AATGTCTGGG AAGTAT                  346
```

(2) INFORMATION FOR SEQ ID NO:17:

(i) SEQUENCE CHARACTERISTICS:
        (A) LENGTH: 154 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Leu Asn Lys Tyr Tyr Asn Glu Lys Cys Gln Ala Arg Lys Ala Ala Ile
1               5                   10                  15

Ala Lys Thr Ile Arg Glu Val Cys Lys Val Val Ser Asp Val Leu Lys
            20                  25                  30

Glu Val Glu Val Gln Glu Pro Arg Phe Ile Ser Ser Leu Asn Glu Arg
        35                  40                  45

Tyr Glu Gly Leu Glu Val Ile Pro Pro Thr Glu Phe Glu Val Val Leu
    50                  55                  60

Tyr Leu Asn Gln Met Gly Val Phe Asn Phe Val Asp Asp Gly Ser Leu
65                  70                  75                  80

Pro Gly Cys Ala Val Leu Lys Leu Ser Asp Gly Arg Lys Arg Ser Met
                85                  90                  95

Ser Leu Trp Val Glu Phe Ile Thr Ala Gly Leu Ser Ala Arg Lys Ile
            100                 105                 110

Arg Ser Arg Phe Gln Thr Leu Val Ala Gln Ala Val Tyr Arg Asp Val
        115                 120                 125

Val Lys Met Val Ala Asp Thr Ser Glu Val Lys Leu Arg Ile Arg Asp
    130                 135                 140

Arg Tyr Val Val Gln Ile Lys Ser Ala Phe
145                 150
```

(2) INFORMATION FOR SEQ ID NO:18:

(i) SEQUENCE CHARACTERISTICS:
        (A) LENGTH: 503 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

```
CCATCTGAAT AAATACTACA ACGAAAAATG CCAAGCCAGG AAAGCTGCCA TTGCCAAAAC    60
TATCCGGGAA GTCTGCAAAG TAGTTTCCGA CGTACTGAAG GAAGTGGAAG TGCAGGAGCC   120
GCGGTTCATC AGCTCTCTCA ACGAGATGGA CAATCGCTAC GAGGGCCTCG AGGTCATCCC   180
CCCCACCGAA TTTGAAGTGG TGCTTTATCT CAACCAAATG GGGGTGTTCA ACTTCGTGGA   240
CGATGGCTCA CTGCCCGGCT GCGCGGTGCT GAAGTTGAGC GACGGGCGCA AGAGGAGCAT   300
GTCCCTCTGG GTGGAATTCA TTACCGCCTC CGGCTAACCT CTTCGGCGCG CAAAATCCGG   360
TCCAGGTTTT CAGACGCTGG TGGCTCAAGC GGTAGACAAA TGTTAGCTTA CCGGGATGTG   420
GTAAAGATGG TGGCCAGACA CCAGCGAAGT GAAAATTGAG AATCCGAGAT AGGTTACGTG   480
GTTGCAGATC ACGNCGGCTT TTN                                          503
```

(2) INFORMATION FOR SEQ ID NO:19:

(i) SEQUENCE CHARACTERISTICS:
        (A) LENGTH: 432 base pairs (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

```
ATTTTACTTC ATTTATTACC ATCTAATTAA ATAAAAACCA GCAACAAATT AAAATCTAAA      60

TCACAAAAGT AATTATCCAG TGTATTTCAA GTGCATTTTT CAAATATATA ATTCAGATAT     120

TCAAGCGTTA TTATATAAGC TGAATTCAAA TTTCTTTGAA TATATTTAAA TAACATTTCA     180

AGTATATTTA TGGGAATGTT AGAAATAGAA CAAGCAATAT TTGANACAAA ATGTAAACTT     240

TTTAAAGTTC AGACACTTTC AAAGGACAGA TAAANGTACC NGGGGGGGAA TCTACCTTTA     300

AAATGATATC TTTGTTAGTG GGAAATGTCT GGGAGTATCC GGAATGGCNA TTTAAGGTTC     360

TGTTCCNCCA AATCACCAAA ACACCNACCT TCCACACTTT CCAAGGNCAT TGTGGGGTCC     420

CCCTANTTTG TT                                                        432
```

(2) INFORMATION FOR SEQ ID NO:20:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

```
Asn Lys Tyr Tyr Asn Glu Lys Cys Gln Ala Arg Lys Ala Ala Ile Ala
1               5                  10                  15

Lys Thr Ile Arg Glu Val Cys Lys Val Val Ser Asp Val Leu Lys Glu
            20                  25                  30

Val Glu Val Gln Glu Pro Arg Phe Ile Ser Ser Leu Asn Glu Arg Tyr
        35                  40                  45

Glu Gly Leu Glu Val Ile Pro Pro Thr Glu Phe Glu Val Val Leu Tyr
    50                  55                  60

Leu Asn Gln Met Gly Val Phe Asn Phe Val Asp Asp Gly Ser Leu Pro
65                  70                  75                  80

Gly Cys Ala Val Leu Lys Leu Ser Asp Gly Arg Lys Arg Ser Met Ser
                85                  90                  95

Leu Trp Val Glu Phe Ile Thr Ala Ser Gly Ser Ala Arg Lys Ile Arg
            100                 105                 110

Ser Arg Phe Ser Asp
        115
```

(2) INFORMATION FOR SEQ ID NO:21:

(i) SEQUENCE CHARACTERISTICS:
        (A) LENGTH: 1051 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:21:

```
CAGGAGCCGC GGTTCATCAG CTCCCTCAAT GAGATGGACA ACCGCTACGA GGGCCTGGAG      60

GTTATCTCTC CCACCGAGTT CGAGGTGGTA TACCTCAACC AGATGGGAGT CTTCAACTTC     120

GTGGACGACG GATCTCTGCC CGGCTGTGCA GTGCTCAAAC TAAGCGATGG GCGGAAACGG     180
```

```
ACGATGTCTC TTTGGGTCGA GTTCATCACA GCGTCTGGCT ACCTTTCTGC GCGCAAGATC      240

CGCTCGCGTT TCCAGACACT AGTAGCCCAG GCGGTGGACA AGTGCAGCTA CCGGGACGTG      300

GTCAAGATGA TCGCCGACAC TAGTGAGGTC AAGTTGCGCA TCAGGGAGCG CTACGTGGTG      360

CAAATCACCC CAGCGTTCAA GTGCACCGGG ATCTGGCCTC GCAGCGCGGC ACACTGGCCT      420

ATGCCCCACA TCCCCTGGCC CGGCCCCAAT CGGGTGGCGG AGGTCAAGGC CGAAGGTTTC      480

AACTTGCTCT CCAAGGAGTG CTACTCGCTG ACTGGCAAGC AGAGCTCCGC AGAAAGCGAC      540

GCCTGGGTGC TGCAGTTCGG TGAGGCGGAG AACCGCTTGC TGATGGGCGG CTGTAGAAAC      600

AAGTGCCTCT CGGTGCAGAA GACGCTGCGG GACCGGCACC TGGAGCTGCC TGGCCAGCCG      660

CTCAATAACT ACCACATGAA GACGCTGCTG CTGTACGAGT GCGAGAAACA CCCGAGGGAA      720

ACGGACTGGG ACGAGGCTTG CTTGGGCGAC CGTCTGAACG GCATCCTGCT ACAGCTCATC      780

TCCTGCCTGC AGTGCCGCCG CTGCCCTCAC TACTTTTTGC CCAACCTCGA CCTCTTCCAG      840

GGTAAGCCCC ACTCGGCCCT GGAGAGCGCT GCCAAGCAGA CCTGGAGATT GGCCAGGGAA      900

ATCCTCACCA ATCCCAAAAG CTTGGACAAA CTATAGAGTG CTGCCGACTG CGTGGAAAGC      960

AACATAAATG GGCATGCTCT CCCAGAACAC ACAACAACAG CAAAAACTCG AAACACAAAC     1020

TTTTATGTAA ATCACCTGAA AGAACGGGAG T                                    1051
```

(2) INFORMATION FOR SEQ ID NO:22:

(i) SEQUENCE CHARACTERISTICS:
        (A) LENGTH: 311 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

```
Gln Glu Pro Arg Phe Ile Ser Ser Leu Asn Glu Met Asp Asn Arg Tyr
 1               5                  10                  15

Glu Gly Leu Glu Val Ile Ser Pro Thr Glu Phe Glu Val Val Tyr Leu
            20                  25                  30

Asn Gln Met Gly Val Phe Asn Phe Val Asp Asp Gly Ser Leu Pro Gly
        35                  40                  45

Cys Ala Val Leu Lys Leu Ser Asp Gly Arg Lys Arg Thr Met Ser Leu
    50                  55                  60

Trp Val Glu Phe Ile Thr Ala Ser Gly Tyr Leu Ser Ala Arg Lys Ile
65                  70                  75                  80

Arg Ser Arg Phe Gln Thr Leu Val Ala Gln Ala Val Asp Lys Cys Ser
                85                  90                  95

Tyr Arg Asp Val Val Lys Met Ile Ala Asp Thr Ser Glu Val Lys Leu
            100                 105                 110

Arg Ile Arg Glu Arg Tyr Val Val Gln Ile Thr Pro Ala Phe Lys Cys
        115                 120                 125

Thr Gly Ile Trp Pro Arg Ser Ala Ala His Trp Pro Leu Pro His Ile
    130                 135                 140

Pro Trp Pro Gly Pro Asn Arg Val Ala Glu Val Lys Ala Glu Gly Phe
145                 150                 155                 160

Asn Leu Leu Ser Lys Glu Cys Tyr Ser Leu Thr Gly Lys Gln Ser Ser
                165                 170                 175

Ala Glu Ser Asp Ala Trp Val Leu Gln Phe Gly Glu Ala Glu Asn Arg
            180                 185                 190
```

-continued

```
Leu Leu Met Gly Gly Cys Arg Asn Lys Cys Leu Ser Val Gln Lys Thr
        195                 200                 205

Leu Arg Asp Arg His Leu Glu Leu Pro Gly Gln Pro Leu Asn Asn Tyr
    210                 215                 220

His Met Lys Thr Leu Leu Tyr Glu Cys Glu Lys His Pro Arg Glu
225                 230                 235                 240

Thr Asp Trp Asp Glu Ala Cys Leu Gly Asp Arg Leu Asn Gly Ile Leu
            245                 250                 255

Leu Gln Leu Ile Ser Cys Leu Gln Cys Arg Arg Cys Pro His Tyr Phe
        260                 265                 270

Leu Pro Asn Leu Asp Leu Phe Gln Gly Lys Pro His Ser Ala Leu Glu
    275                 280                 285

Ser Ala Ala Lys Gln Thr Trp Arg Leu Ala Arg Glu Ile Leu Thr Asn
    290                 295                 300

Pro Lys Ser Leu Asp Lys Leu
305                 310
```

METHOD OF DETECTING EXPRESSION OF MAB-21

This application is a continuation-in-part of U.S. Ser. No. 08/835,604, filed Apr. 9, 1997 which claims priority of U.S. Provisional Application No. 60/011,607, filed Apr. 10, 1996, the content of which is incorporated herein by references.

Within this application, publications are referenced within parentheses. Full citations for these references may be found at the end of each series of experiments. The disclosures of these publications in their entireties are hereby incorporated by reference into this application in order to more fully describe the state of the art to which this invention pertains.

BACKGROUND OF THE INVENTION

The C. elegans gene mab-21 is required for the choice of alternate cell fates by four epidermal and neuronal cells present in the lateral epidermis on each side of the male tail. Three of the four cells are products of one of nine cell sublineages leading to nine sensory rays. In mab-21 mutants, two cells, one neuronal and one glial-like, in one of the nine rays assume characteristics of the same cells found in a more anterior ray. In addition, a hypodermal cell generated by the same cell sublineage makes a different choice of fusion partner. The fourth cell affected is a hypodermal cell, which in mab-21 mutants is transformed into a neuroblast. All these cells lie together in the lateral tail epidermis, suggesting that mab-21 acts as part of a localized pattern formation mechanism. mab-21 mutant males and hermaphrodites have additional pleiotropic phenotypes affecting movement, body shape, and fecundity, suggesting that mab-21 has functions outside the tail region of males. Applicant shows that the three known alleles of mab-21 are hypomorphs of a new essential gene with an embryonic function. The mab-21 gene encodes a novel protein of 386 amino acids. In further studies of the action of mab-21 in the male tail epidermis, applicant shows by mosaic analysis that mab-21 acts cell autonomously to specify the properties of one sensory ray, but non-autonomously in the hypodermal versus neuroblast cell fate choice. Presence of cell signaling in the choice of the neuroblast fate was confirmed by cell ablation experiments. Mutations in mab-21 were shown previously to be genetic modifiers of the effects of HOM-C/Hox gene mutations on ray identity specification. The results presented here support the conclusion that mab-21 acts as part of a mechanism required for correct cell fate choice, possibly involving the function of HOM-C/Hox genes in several body regions.

During animal development, pattern formation mechanisms guide the generation of variant forms of a variety of serially repeated structures, such as segments, rhombomeres, digits, or cell sublineages. One way in which these pattern formation mechanisms exert their influence is by determining unique states of expression of HOM-C/Hox transcription factors within cells (McGinnis and Krumlauf, 1992). HOM-C/Hox transcription factors, in turn, dictate transcription of characteristic patterns of downstream target genes that determine the individual properties of separate units (Andrew and Scott, 1992; Botas, 1993).

In C. elegans, HOM-C/Hox genes determine variant forms of epidermal and neuronal cell sublineages that are serially repeated along the anteroposterior body axis (Sulston and Horvitz, 1977; Wang et al. 1993). As one example of this process, applicant has studied development of a set of nine bilateral pairs of peripheral sensory organs known as rays present in the posterior region of males. Each ray develops from an identical ray cell sublineage, yet each develops at a different epidermal site, can have a distinct morphology and pattern of neurotransmitter expression, and can mediate distinct behavioral responses during mating (Suiston et al., 1980; Loer and Kenyon, 1993; Liu and Sternberg, 1995). In addition, the cells of each ray appear to express a unique combination of cell recognition functions necessary for their assembly as a separate organelle. Evidence for such distinct ray morphogenetic identities came from studies of mutations in several genes required for independent development of subsets of rays (Baird et al., 1991). In males mutant for these genes, neighboring rays fuse together during development, suggesting that they have lost their distinct identities and instead express common assembly functions.

It was shown that HOM- C/Hox genes play a role in endowing separate developmental and morphological identities to the rays (Chow and Emmons, 1994). Levels of expression of these genes within the terminal cells of the ray lineages dictate distinct morphological identities that allow the rays to assemble independently. Several of the ray fusion genes applicant identified were shown to be genetic modifiers of HOM-CiHox effects on ray development, suggesting that ray fusion genes act in a common pathway with HOM-CoHox genes (Chow and Emmons, 1994). In the present paper applicant characterizes further one of these HOM-C/Hox gene modifier loci.

Mutations in the gene mab-21 resulted in the specific transformation of the identity of one of the rays into that of a more anterior ray (Baird et al., 1991). Here applicant characterizes this transformation in greater detail, and document effects of mnab-21 mutations on the cell fate choices and/or differentiation of neural and hypodermal cells. mab-21 also appears to function outside of the tail region of males, and applicant shows that his amab-21 mutations are hypomorphic alleles of a new essential gene with an embryonic function. Applicant cloned the gene and show that it encodes a novel protein of 386 amino acids. In further studies of its action in the male tail, applicant shows that mab-21 acts cell autonomously in specifying a ray identity, and thus could function together with the autonomously-acting HOM-C/Hox genes. Its action in the choice of epidermal or neuroblast cell fate by a neighboring cell was non-autonomous, however. The results are consistent with a model in which mab-21 acts as part of a localized pattern formation mechanism that dictates the fates of cells in the male tail lateral epidermis. It could as well have a wider function in specification by HOM-C/Hox genes of specialized structures or cell identities elsewhere in the body.

SUMMARY OF THE INVENTION

This invention provides an isolated polynucleotide comprising a member selected from the group consisting of: (a) a polynucleotide encoding MAB-21 protein; (b) a polynucleotide capable of hybridizing to and which is at least 60% identical to the polynucleotide of (a); and (c) a polynucleotide fragment of the polynucleotide of (a) or (b). This invention also provides a vector comprising the above-described DNA.

This invention also provides a host cell comprising the above-described vector. This invention further provides a host vector system for the production of MAB-21 protein comprising the above vector and a suitable host. In an embodiment, the suitable host is selected from a group consisting of a bacterial cell, plant and animal cell.

This invention provides a nucleic acid molecule of at least 15 nucleotides capable of specifically hybridizing with a unique sequence of a nucleic acid molecule which is complementary to the above-described nucleic acid molecule.

This invention also provides methods of detecting expression of nmab-21 or its homologs in a sample which comprises steps of: a) obtaining total mRNA from the sample; b) contacting the mRNA so obtained with a labelled nucleic acid probe molecules which are described above under hybridizing conditions; and c) determining the presence of mRNA hybridized to the molecule, and thereby detecting the expression of the mab-21 or its homologs in the sample.

This invention provides methods of detecting expression of protein products of mab-21 or mab-21 homologs in a sample which comprises steps of: a) obtaining protein extracts from the sample; b) contacting the obtained protein extract with an antibody capable of specifically recognizing the protein products of mab-21 or mab-21 homologs under conditions permitting the formation of complexes between the antibody and the protein products, measuring the amount of the formed complexes, thereby detecting the expression of the protein product of mab-21 and mab-21 homologs.

This invention also provides purified MAB-21 proteins or fragments thereof.

This invention also provides methods for production of an antibody capable of binding to protein products of mab-21 or mab-21 homologs comprising: a) administering an amount of purified protein products of mab-21 or mab-21 homologs to a suitable animal effective to produce an antibody against the protein in the animal; and b) testing the produced antibody for capability to bind the administered protein. In an embodiment, the antibody is produced by in vitro immunization.

This invention also provides methods for production of an antibody capable of binding to protein products of mab-21 or mab-21 homologs comprising: a) determining conserved regions revealed by alignment of MAB-21 protein and the protein product of mab-21 homologs; b) synthesizing peptides corresponding to the revealed conserved regions; c) administering an amount of the synthesized peptides to a suitable animal effective to produce an antibody against the peptides in the animal; and d) testing the produced antibody for capability to bind the administered protein. In an embodiment, the antibodies are produced by in vitro immunization.

This invention further provides antibodies produced by the above methods. In an embodiment, these antibodies are monoclonal.

This invention further provides antibodies capable of binding specifically to MAB-21 protein. In an embodiment, the antibodies are monoclonal.

This invention also provides assays for measuring the amount of protein product of mab-21 or mab-21 homologs comprising steps of: a) contacting the sample with at least one of the antibody capable of binding specifically to MAB-21 protein to form a complex with said antibody and the protein, and b) measuring the amount of the protein in said biological sample by measuring the amount of said complex.

This invention also provides methods to purify MAB-21 protein or the protein product of mab-21 homologs comprising steps of: a) coupling at least one antibody capable of binding specifically to the protein products of mab-21 or its homologs to a solid matrix; b) incubating the coupled antibody of a) with a cell lysate containing MAB-21 protein or the protein product of mab-21 homologs under the condition permitting binding of the coupled antibody and protein; c) washing the solid matrix to eliminate impurities and d) eluting the protein from the coupled antibody.

This invention also provides transgenic animal comprising DNA molecule comprising a member selected from the group consisting of: (a) a polynucleotide encoding MAB-21 protein;(b) a polynucleotide capable of hybridizing to and which is at least 60% identical to the polynucleotide of (a); and (c) a polynucleotide fragment of the polynucleotide of (a) or (b). In an embodiment, the transgenic animal is a *Caenorhabditis elegans*. This invention further provides a transgenic *Caenorhabditis elegans* animal comprising a human homologous mab-21 gene.

This invention provides methods for identifying a mutant mab-21 gene in animals which have reduced mab-21 function comprising steps of: a) treating wild type *Caenorhabditis elegans* hermaphrodite animals with effective amount of a mutagen; b) screening in F1, F2 or F3 generations for animals with Mab-21 mutant phenotype; and c) identifying, isolating and segregating the mutant animals in subsequent generations to homozygosity.

This invention also provides a mutant mab-21 animal identified by the above method.

This invention also provides methods for identification of a mutant gene which reduce mab-21 comprising performing DNA sequence analysis of the mutant mab-21 animal identified by the above method. This invention also provides mutant gene identified by the above method.

This invention provides methods for identifying mutations in mab-21 homologs in animals comprising steps of: a) obtaining DNA from the mutated and wild-type animals; b) amplifying on both wild-type and the mutant DNAs with appropriate mab-21 primers by polymerase chain reactions; c) hybridizing the amplified DNA under conditions permitting the formation of mismatched hybrid molecules a nd complementary hybrid molecules; d) separating the mismatched and complementary hybrid amolecules by electrophoresis; e) isolating the mismatched hybrid molecule; and f) determining the mismatched sequences, thereby identifying mutations in mab-21 homologs.

Finally, this invention also provides methods for identifying various suppressor, enhancer and modifier mutations in animals carrying mab-21 mutation. This invention provides animals carrying these suppressor, enhancer and modifier mutations. This invention also provides the suppressor, enhancer and modifier genes comprising steps of genetic mapping, physical mapping and DNA sequence analysis of these genes.

BRIEF DESCRIPTION OF THE FIGURES

FIG. 1A. wild type *C. elegans* male tail, ventral view, showing fan and rays. Arrow, ray 4, arrowhead, ray 6. Nomarski photomicrograph, scale bar=10 microns.

FIG. 1B. mab-21mutant male tail. Arrow indicates large ray consisting of a fusion of rays 4 and 6, E indicates the "ectopic" tenth ray.

FIG. 1C. Arrangement of seam cells in the lateral epidermis of the male tail, late L3 larval stage. Rn cells (n=1–9) are ray precursor cells, T.apapa is a hypodermal cell. Most of the remainder of the surface is covered by a hypodermal syncytium. The lineal relationships of cells affected by mab-21 mutations is indicated above.

FIG 1D. Arrangement of seam cells approximately 5 hours later than the arrangement shown in C. At this time, the Rn cells in wild type express the ray sublineage, shown for R6 below. T.apapa fuses with the surrounding hypodermal syncytium. A, RnA; B, RnB; st, Rnst; hyp, hypodermal cell; X, programmed cell death.

FIGS. 2A–2B. Tip of ray 4 in wild type. The dendritic ending of R4B narrows and is exposed to the exterior (thin arrow). It is surrounded by a surface density at the point of narrowing (thick arrow).

FIG. 2C. Cross section near the tip of ray 6 in wild type. This and adjacent sections through the tip reveal no surface density surrounding the dendritic ending of R6B.

FIGS. 2M–2N. Representative cross section of the "ectopic" ray generated by T.apapa in mab-21, showing that it has normal structure, typical of rays 1–5, 7–9 in wild type. The level of this section is indicated in J. Scale bars: in C, applies to A–C; in F applies to F–I; in M, applies to K–N. Definitions: hyp, hypodermis; str, structural cell; ext, exterior; fan, cuticular fan; RnA" and RnB", second pair of neurons in fused ray.

FIGS. 3A–3D. Photomicrographs and diagrams of cell boundaries in the left lateral tail hypodermis, visualized by indirect immunofluorescence staining. In mab-21, the cell boundaries delineating R6.p, which normally contact ray 5, have disappeared, and ray 5 lies within the SET. An additional Rn.p cell (T.apapap) and an ectopic ray (E) are present. Ph, phasmid.

FIGS. 3E–3F. Visualization of cell boundaries in the left lateral tail hypodermis, visualized by SDS treatment. In wild type there are 5 nuclei within the SET, and R6.p can be seen as a separate cell. In mab-21, there are 6 nuclei in the SET.

A signal from R6 causes T.apapa to express the ray neuroblast cell fate. Action of mab-21 within either cell blocks the effect of this signal.

FIG. 8: Alignment of Caenorhabditis elegans MAB-21 protein with other protein products of mab-21 homologs from B.malayi (SEQ ID NO:1), C.briggsae (SEQ ID NO:2), H.sapiens (SEQ ID NO:4), M.musculs and predicted ORF (SEQ ID NO:5), F35G12.6 (SEQ ID NO:6), from C.elegans (SEQ ID NO:3) genome project consortium.

FIG. 9. Genomic sequence of C.briggsae mab-21 locus and the putative MAB-21 protein amino acid sequence (SEQ ID NO:8) predicted from genomic sequence (SEQ ID NO:7).

FIG. 10. DNA sequence of the EST clone from parasitic nematode, Brugia malayi (SEQ ID NO:9), and the putative MAB-21 protein amino acid sequence (SEQ ID NO:10).

FIG. 11. cDNA sequence of C.elegans mab-21 gene (SEQ ID NO:11) and the predicted protein amino acid sequence (SEQ ID NO:12).

FIG. 12. cDNA sequence of human mab-21 gene (SEQ ID NO:13) and the predicted protein amino acid sequence (SEQ ID NO:14).

FIG. 13. DNA sequence of the EST clone (SEQ ID NO:15), ym36d10 (SEQ ID NO:16), from human and the putative MAB-21 protein amino acid sequence (SEQ ID NO:17).

FIG. 14. DNA sequence of the EST clone (SEQ ID NO:18), ym45d11 (SEQ ID NO:19), from human and the putative MAB-21 protein amino acid sequence (SEQ ID NO:20).

FIG. 15. cDNA sequence of mouse mab-21 gene (SEQ ID NO:21) and the predicted protein amino acid sequence (SEQ ID NO:22).

Figure 16:
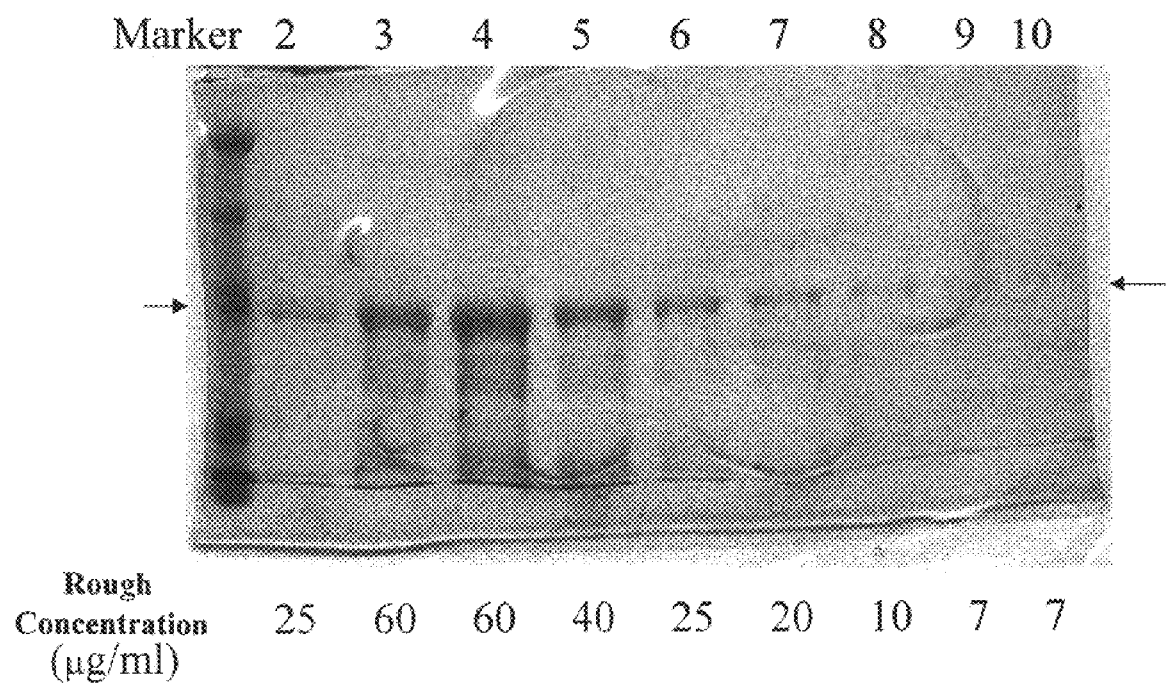

FIG. 16. Protein electrophoresis of the fusion protein purified from affinity chromatography using maltose binding protein (MBP) tag and chromatographic column with maltose conjugated resin. Fractions collected were loaded into 12% polyacrylamide gel, electrophoresed, and stained with Coomassie Brilliant Blue. The purified protein is marked with an arrow.

Figure 17:
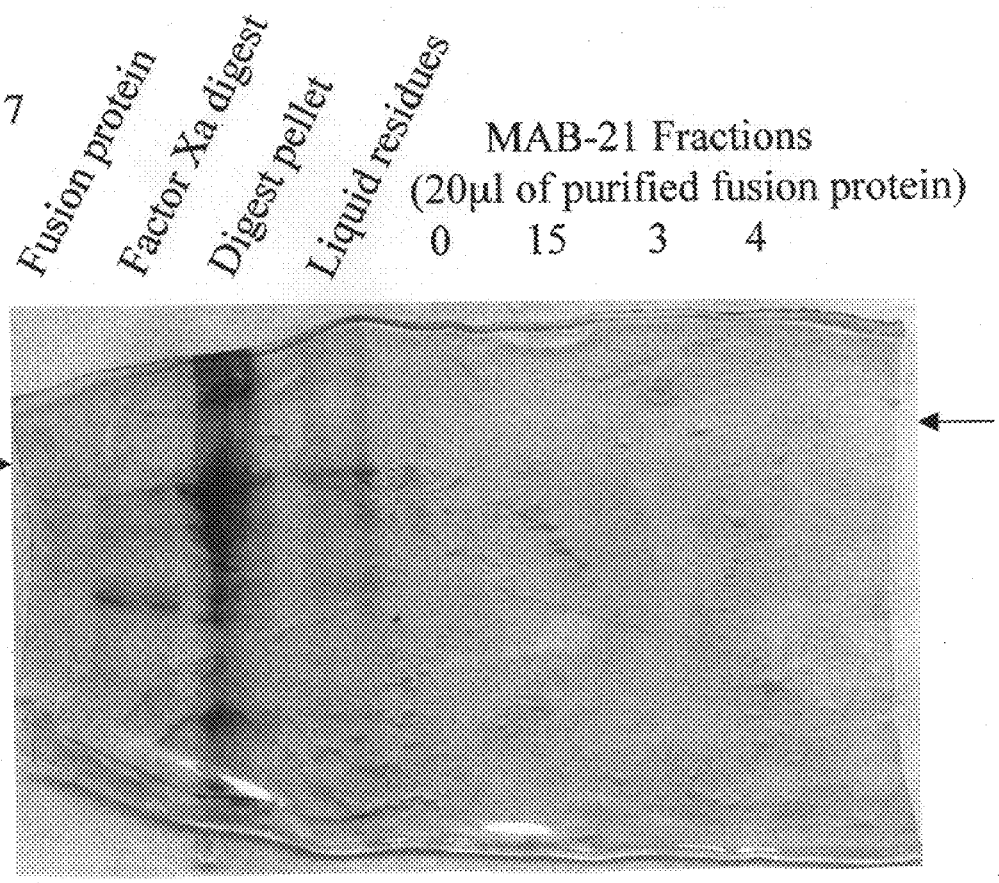

FIG. 17. Protein gel showing the purification of the MAB-21 from MBP-MAB-21 fusion protein. Fusion protein (arrow) was incubated with Factor Xa at 37° C. overnight. The cleavage product (*) generated was separated in polyacrylamide gel (12%), and visualized by Coomassie Brilliant Blue staining.

Figure 18A:
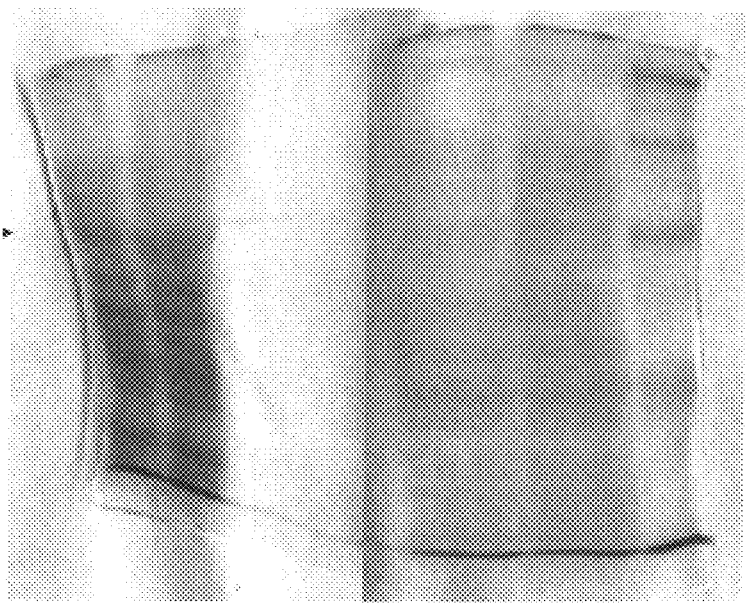

FIG. 18A. Coomassie Brilliant Blue staining of a polyacrylamide gel separating different preparation of protein extract as indicated on the figure. Fusion protein expressed in bacteria is shown with asterisk.

Figure 18B:
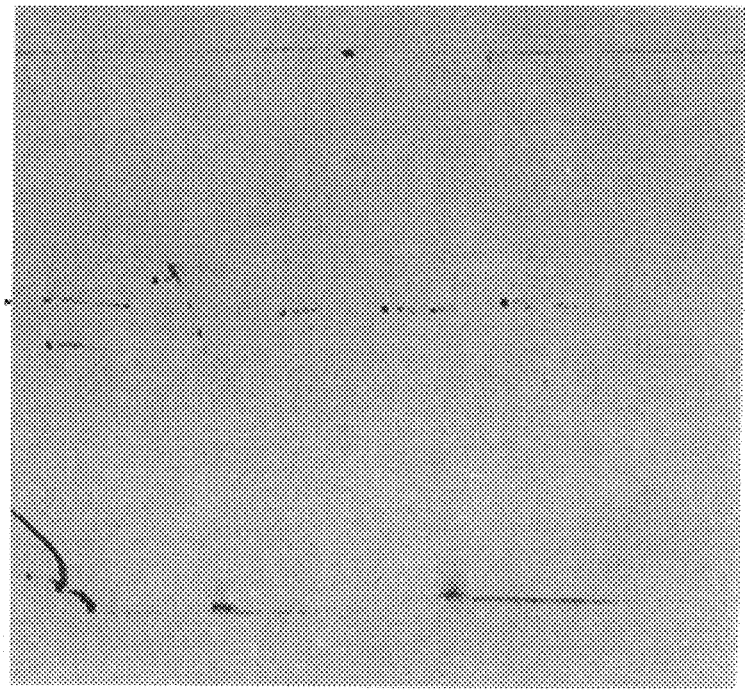

FIG. 18B. Western blot analysis of the membrane carrying the transferred protein. Polyclonal antibody generated in mice with the purified MAB-21 protein was used as the primary antibody. Sheep anti mouse IgG antibody conjugated with Horse Radish Peroxidase was used as the secondary antibody. The specific binding was visualized by adding diaminobenzidine (DAB) as substrate for the bound secondary antibody. The results suggest that the polyclonal antibody so obtained can recognize a specific protein in the worm extract with the same antigenicity as MAB-21.

FIG. 19. Result of an ELISA assay using polyclonal antibody generated from mice immunized with purified MAB-21 protein and MBP-MAB-21 protein as antigen. Serial dilution of the antibody in the assay shows that the serum has high titer of antibody specific for the MAB-21 protein.

DETAILED DESCRIPTION OF THE INVENTION

This invention provides an isolated polynucleotide comprising a member selected from the group consisting of: (a) a polynucleotide encoding MAB-21 protein; (b) a polynucleotide capable of hybridizing to and which is at least 60% identical to the polynucleotide of (a); and (c) a polynucleotide fragment of the polynucleotide of (a) or (b). In an embodiment, the polynucleotide is DNA.

The isolated polynucleotide of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected hosts; the provision of sites for cleavage by restriction endonuclease enzymes; and the provision of additional initial, terminal or intermediate DNA sequences that facilitate construction of readily expressed vectors.

Mab-21 homologs in other species can be obtained by screening genomic library or cDNA libraries of different species using polynucleotide fragment of mab-21 gene as labelled nucleic acid molecule, in conditions permitting DNA hybridization of DNA molecules. Clones forming stable hybrid with the labelled molecules can be purified, and amplified for characterization. mab-21 homologs in other species can be obtained by polymerase chain reaction performed with genomic DNA from various species and a pair of oligonucleotides complementing to specific conserved regions of mab-21 gene. The amplified fragment will be used as probe for subsequent screening of genomic or cDNA libraries. mab-21 homologs in other species can also be obtained screening expression library with antibody capable of binding specifically to MAB-21 protein, provided that antigenic epitopes are conserved in these homologs. However, other methods for performing these screening steps are well known to those skilled in the art, and the discussion above is merely an example.

This invention also provides a vector comprising the above-described DNA. In an embodiment, the vector is a plasmid.

This invention also provides a host cell comprising the above-described vector. This invention further provides a host vector system for the production of MAB-21 protein comprising the above vector and a suitable host. In an embodiment, the suitable host is selected from a group consisting of a bacterial cell, plant and animal cell. In another embodiment, the suitable host cells are insect cells.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the MAB-21 protein.

This invention further provides an isolated DNA or cDNA molecule described hereinabove wherein the host cell is selected from the group consisting of bacterial cells (such as *E. coli*), yeast cells, fungal cells, insect cells and animal cells. Suitable animal cells include, but are not limited to Vero cells, HeLa cells, Cos cells, CV1 cells and various primary mammalian cells.

This invention provides a nucleic acid molecule of at least 15 nucleotides capable of specifically hybridizing with a unique sequence of a nucleic acid molecule which is complementary to the above-described nucleic acid molecule. In an embodiment, this probe molecule is a DNA molecule. In another embodiment, this probe molecule is an RNA molecule.

This nucleic acid molecule of at least 15 nucleotides capable of specifically hybridizing with a sequence of a nucleic acid molecule encoding MAB-21 protein can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes MAB-21 protein into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting a selected nucleic acid molecule downstream of a bacteriophage promoter such as T3, T7 or SP6. Large amounts of RNA probe may be produced by incubating the labeled nucleotides with the linearized mab-21 fragment where it contains an upstream promoter in the presence of the appropriate RNA polymerase.

This invention also provides methods of detecting expression of mab-21 or its homologs in a sample which comprises steps of: a) obtaining total mRNA from the sample; b) contacting the mRNA so obtained with a labelled nucleic acid probe molecules which are described above under hybridizing conditions; and c) determining the presence of mRNA hybridized to the molecule, and thereby detecting the expression of the mab-21 or its homologs in the sample.

In one embodiment of this invention, nucleic acids are extracted by precipitation from lysed cells and the mRNA is isolated from the extract using an oligo-dT column which binds the poly-A tails of the mRNA molecules. The mRNA is then exposed to radioactively labelled probe on a nitrocellulose membrane, and the probe hybridizes to and thereby labels complementary mRNA sequences. Binding may be detected by luminescence autoradiography or scintillation counting. However, other methods for performing these steps are well known to those skilled in the art, and the discussion above is merely an example.

This invention provides methods of detecting expression of protein products of mab-21 or mab-21 homologs in a sample which comprises steps of: a) obtaining protein extracts from the sample; b) contacting the obtained protein extract with an antibody capable of specifically recognizing the protein products of mab-21 or mab-21 homologs under conditions permitting the formation of complexes between the antibody and the protein products, measuring the amount of the formed complexes, thereby detecting the expression of the protein product of mab-21 and mab-21 homologs.

As used herein, the sample may include any biological samples obtained from an living organism. The sample may contain animal tissues or animal cells. Animals tissue or clinical samples can be obtained by biopsy, or sample can be cell lines generated from tissue from animals or patients. These samples will be processed to obtain purified protein or RNA for the detection assays, based on nucleic acid hybridization or on antibody-antigen complex formation.

This invention also provides purified MAB-21 proteins or fragments thereof.

This invention also provides purified MAB-21 proteins or fragments comprising steps of: a) inserting full length or truncated mab-21 cDNAs into a bacterial, yeast or mammalian expression vector with appropriate promoter regulatory elements, fusion protein cassettes (tag), and termination signals, b) expressing the fusion genes in the corresponding host cells, c) obtaining cell lysate containing the fusion protein, d) employing affinity chromatographic procedure using matrix coupled with antibody specific for the protein tag to permit binding of the fusion protein to the matrix, e) washing the matrix to eliminate impurities, f) eluting the protein from the coupled antibody, g) cleaving the tag from the fusion protein with appropriate protease, h) removing the tag in the solution by affinity chromotograpy, i) eluting the purified protein products of mab-21 or mab-21 homolog.

This invention also provides methods for production of an antibody capable of binding to protein products of mab-21 or mab-21 homologs comprising: a) administering an amount of purified protein products of mab-21 or mab-21 homologs to a suitable animal effective to produce an antibody against the protein in the animal; and b) testing the produced antibody for capability to bind the administered protein. In an embodiment, the antibody is produced by in vitro immunization.

This invention also provides methods for production of an antibody capable of binding to protein products of mab-21 or mab-21 homologs comprising: a) determining conserved regions revealed by alignment of MAB-21 protein and the protein product of mab-21 homologs; b) synthesizing peptides corresponding to the revealed conserved regions; c) administering an amount of the synthesized peptides to a suitable animal effective to produce an antibody against the peptides in the animal; and d) testing the produced antibody for capability to bind the administered protein. In an embodiment, the antibodies are produced by in vitro immunization.

This invention further provides antibodies produced by the above methods. In an embodiment, these antibodies are monoclonal.

This invention further provides antibodies capable of binding specifically to protein product of mab-21 or mab-21 homologs.

In an embodiment, the antibodies are monoclonal.

This invention provides a method to select specific regions on the MAB-21 or protein products of mab-21 homologs to generate antibodies. The protein sequence may be determined from the mab-21 sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to MAB-21 protein. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art.

This invention further provides a method for production of an antibody capable of binding to protein products of mab-21 and mab-21 homolog comprising steps of: a) stimulating antibody response in a mouse by non-specific antigen; b) isolating mRNA from the stimulated mouse; c) performing polymerase chain reaction on the isolated mRNA with appropriate primers to produce cDNAs of the antibodies; d) cloning the cDNAs into an expression library; e) screening the expression library resulting from step d), which contains clones of cDNAs, with the protein product of mab-21 or mab-21 homolog; f) identifying and isolate the clone capable of binding to the protein product. The above-described in vitro immunization procedure is known in art (See e.g. McCafferty, J. et al. (1990) Phage antibodies: Filamentous phage display antibody variable domains. Nature 348:552–554.). The expression library used may be a phage library. In a preferred embodiment, the library is a phage display library. The amplified cDNAs may be linked to a phage coat protein gene of a filamentous phage vector. Appropriate cells may be transformed by the vector to generate a library of phages expressing various immunoglobulin proteins on the phage surface. This library may then be screened with the antigen of interest. The identified clone will be the antibody capable of binding to the antigen of interest.

These antibodies are useful to detect the expression of protein product of mab-21 or mab-21 homologs in living animals, in humans, or in biological tissues or fluids isolated from animals or humans.

This invention also provides assays for measuring the amount of a protein product of mab-21 or mab-21 homologs comprising steps of: a) contacting the sample with at least one of the antibody capable of binding specifically to MAB-21 protein or protein product of mab-21 homologs to form a complex with said antibody and the protein, and b) measuring the amount of the protein in said biological sample by measuring the amount of said complex.

This invention also provides methods to purify MAB-21 protein or the protein product of mab-21 homologs comprising steps of:

a) coupling at least one antibody capable of binding specifically to MAB-21 protein or protein product of mab-21 homologs to a solid matrix; b) incubating the coupled antibody of a) with a cell lysate containing MAB-21 protein or the protein product of mab-21 homologs under the condition permitting binding of the coupled antibody and protein; c) washing the solid matrix to eliminate impurities and d) eluting the protein from the coupled antibody.

This invention also provides transgenic animal comprising DNA molecule comprising a member selected from the group consisting of: (a) a polynucleotide encoding MAB-21 protein;(b) a polynucleotide capable of hybridizing to and which is at least 60% identical to the polynucleotide of (a); and (c) a polynucleotide fragment of the polynucleotide of (a) or (b). In an embodiment, the transgenic animal a *Caenorhabditis elegans*. This invention further provides a transgenic *Caenorhabditis elegans* animal comprising a human homologous mab-21 gene.

This invention provides methods for identifying a mutant mab-21 animal which reduces mab-21 function comprising steps of: a) treating wild type *Caenorhabditis elegans* hermaphrodite animals with effective amount of a mutagen; b) screening in F1, F2 or F3 generations for animals with Mab-21 mutant phenotype; and c) identifying, isolating and segregating the mutant animals in subsequent generations to homozygosity.

This invention also provides a mutant mab-21 animal identified by the above method.

This invention also provides methods for identification of a mutant mab-21 gene which reduces mab-21 function comprising performing DNA sequence analysis of the mutant mab-21 animal identified by the above method.

This invention also provides mutant genes identified by the above method.

This invention provides methods for identifying mutations in mab-21 homologs in animals comprising steps of: a) obtaining DNA from the mutant and wild-type animals; b) amplifying both wild-type and the mutant DNAs with a pair of mab-21 homolog-specific oligonucleotide primers by polymerase chain reactions; c) hybridizing the amplified DNA under conditions permitting the formation of mismatched hybrid molecules and complementary hybrid molecules; d) separating the mismatched and complementary hybrid molecules by electrophoresis; e) isolating the mismatched hybrid molecule; and f) determining the mismatched sequences, thereby identifying mutations in mab-21 homologs.

This invention provides methods for producing an animal carrying an extragenic suppressor gene mutation of a mab-21 allele comprising: a) mutagenizing mab-21 mutant hermaphrodites with an effective amount of a mutagen; b) screening for revertants in the F1, F2 and F3 generations; and c) identifying, isolating and segregating the animals carrying the suppressor gene mutation in subsequent generations to homozygosity. This invention further provides an animal carrying a mutation of a mab-21 suppressor gene produced by the above method. This invention also provides methods for identification of a suppressor gene comprising performing genetic mapping, physical mapping and DNA sequence analysis of the suppressor mutation of the above isolated animal to identify the suppressor gene. This invention also provides a suppressor gene identified by the above method.

This invention provides methods for producing an animal carrying an extragenic enhancer mutation of a mab-21 allele comprising: a) mutagenizing mab-21 mutant hermaphrodites with an effective amount of a mutagen; b) screening for enhancement of Mab-21 mutant phenotype in the F1, F2 and F3 generations; and c) identifying, isolating and segregating the animals carrying the enhancer mutation in subsequent generations to homozygosity. This invention also provides an animal carrying a mutation of a mab-21 enhancer gene produced by the above method. This invention also provides a method for identification of an enhancer gene comprising performing genetic mapping, physical mapping and DNA sequence analysis of the enhancer mutation of the above isolated animal to identify the enhancer gene. This invention further provides an enhancer gene identified by above method.

This invention provides methods for producing an animal carrying an extragenic modifier mutation of a mab-21 allele comprising: a) mutagenizing mab-21 mutant hermaphrodites with an effective amount of a mutagen; b) screening for alteration of Mab-21 mutant phenotype in the F1, F2 and F3 generations; and c) identifying, isolating and segregating the animals carrying the modifier mutation in subsequent generations to homozygosity. This invention also provides an animal carrying a mutation of a mab-21 modifier gene produced by the above method. This invention also provides methods for identification of a modifier gene comprising performing genetic mapping, physical mapping and DNA sequence analysis of the modifier mutation of the isolated animal to identify the modifier gene. This invention further provides a modifier gene identified by above method.

The mutagen includes but is not limited to ethyl methanesulfonate, diethylsulfate, ethyl nitrosy-urea, diepoxybutane, diepoxyoctane, acetaldehyde, formaldehyde, porsalein, UV irradiation, ionizing radiation and activated transposons.

This invention will be better understood from the examples which follow. However, one skilled in the art will readily appreciate that the specific methods and results discussed are merely illustrative of the invention as described more fully in the claims which follow thereafter.

EXPERIMENTAL DETAILS

First Series of Experiments
Materials and Methods
  General Methods and Mapping

Figure 4A:
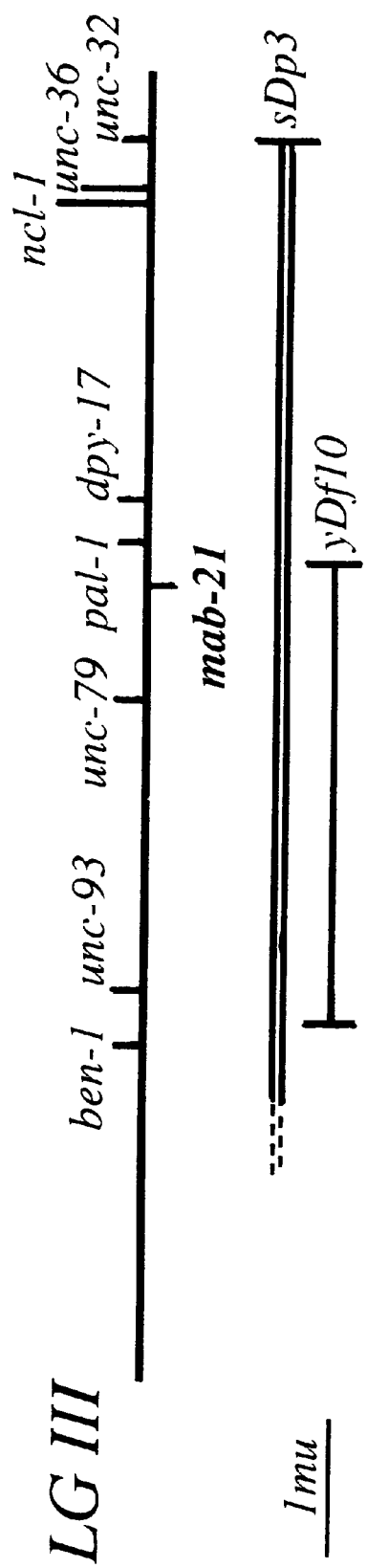
FIG. 4A. Genetic map of linkage group III in the region surrounding mab-21.
Figure 4B:
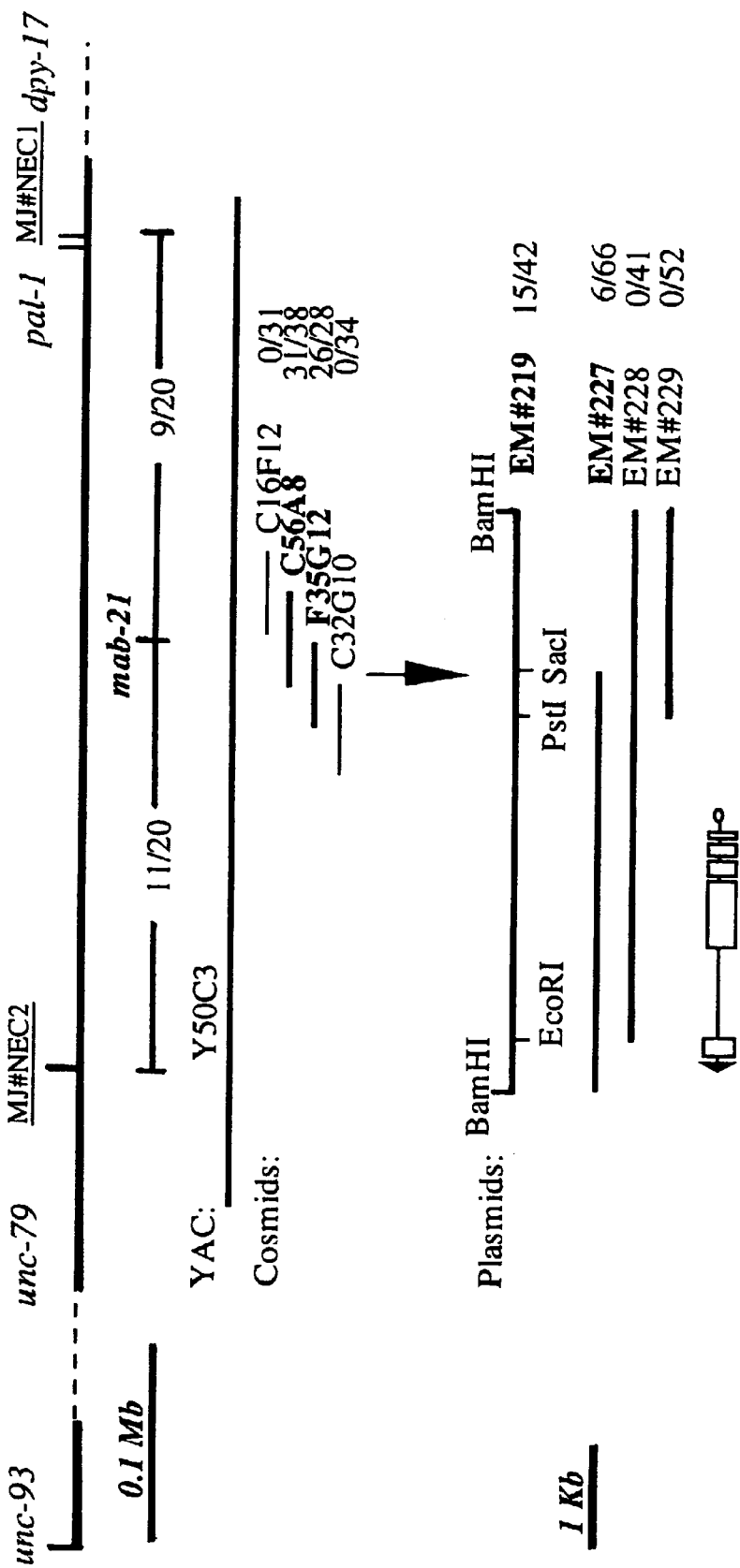
FIG. 4B. Physical map in the region surrounding mab-21. From top to bottom: relationship of physical and genetic markers; the number of recombination events between mab-21 and the two polymorphisms MJ#NEC2 and MJ#NEC1; YAC and cosmid clones and rescuing activity, those shown in bold rescued mab-21 (bx53) with the frequencies indicated; rescuing BamHI restriction fragment subcloned from cosmid C56A8; a BamHI/SacI subclone with rescuing activity and EcoRI/BamHI and PstI/BamHI subclones without rescuing activity; the structure of a mab-21 transcript deducted by comparing genomic and cDNA sequences (open boxes represent exons, circle and arrow represent 5' and 3' ends of the isolated cDNAs respectively).

Nematodes were reared at 20° C. following standard procedures (Brenner, 1974). Most strains carried the him-5(e1490) mutation, which results in a high frequency of spontaneous males in populations of selfing hermaphrodites (Hodgkin et al., 1979). Isolation after EMS mutagenesis of two alleles of mab-21 (bx41 and bx53) has been described previously (Baird et al., 1991); a third allele (sy155) was isolated from a mutant strain kindly provided by H. Chamberlin and P. Sternberg. mab-21 mutations were mapped to the left arm of linkage group III between unc-79 and pal-1 by four factor cross in which the following recombination events were scored: unc-79(12/18) mab-21(3/18) pal-1(3/18) dpy-17 (see FIG. 4A) . mab-21 was placed between two restriction fragment length polymorphisms, MJ#NEC2 and MH#NEC1, by crossing a mab-21 strain to strain EM375 of genotype unc-79 MJ#NEC2 MJ#NEC1 dyp-17 with the following recombination results: unc-79(29/59) MJ#NEC2 (11/59) mab-21(9/59)MJ#NEC1 (10/59)dpy-17(FIG. 4B). EM375 was generated from strain MJ569 provided by J. Miwa.

Cell Lineage Analysis and Cell Ablation Experiments

Cell lineages of mab-21(bx41) (3 sides) and mab-21(bx53) (5 sides) were followed in living animals by Nomarski microscopy following methods described by Sulston and Horvitz (1977). Lineages were followed from late L1 through the L3 molt and division of Rn.a cells. Division of Rn.a cells was taken as an indication of the expression of the ray sublineage.

Cells were ablated with a laser microbeam following procedures described in Chow and Emmons (1994).

Electron Microscopy

Young adult males were rinsed in M9 buffer and place into buffered aldehyde fixative at room temperature. While in fix, the tails were quickly cut off with a scalpel blade. After 1–3 hours in aldehyde fix, samples were transferred through several buffer rinses and refixed in 1% osmium tetroxide. Samples were then dehydrated and embedded in Medcast resion (Ted Pella) and serially sectioned on a diamond knife (cf. Hall, 1995). Some tails were sectioned transverse to the body axis, others lengthwise, either sagittal or frontal, in order to obtain different perspmicrograph the curving rays. Electron micrographs were collected with a Philips CM10 at 2,000–12,000×. Several rays that showed especially good fixation were reconstructed using the Eutectics Electronics 3D-SSRS computer program, after manual tracing of every 3–5th section on a digitizing table. In mab-21 males, normal rays, an ectopic ray, and a fused (4+6) ray could thus be compared from any perspective, and used ans models with which to compare sample sections from additional animals. In all, nine mab-21 adults and four wild type adults were compared in serial thin sections. In particular, effort was made to compare the details of ray openings, ciliary tip specializations, the relative sizes of cellular elements along the length of the rays, and the number and type of cell processes invading the base of each ray. Not all features could be assessed in each specimen, depending upon section angle and varying quality of preservation.

Complementation of Emb Genes

The following embryonic lethal mutations, all temperature sensitive and closely linked to mab-21, were tested for complementation with mab-21: emb-1(hc57), emb-2(hc58), emb-5(hc61), emb-7(hc66), errb-8(hc69), emb-13(g6), and emb-32(g58). Crosses were set up at 16° C. between mab-21(bx53); him-5(e1490) males and emb-n hermaphrodites. After mating took place for two days, the parents were removed, and plates with mostly eggs and a few L1 larvae were transferred to 25° C. mab-21/emb-n male cross progeny were scored for ray fusion phenotype.

Indirect Immunofluorescence Staining of Cell Boundaries

Animals were fixed with 1% paraformaldehyde and permeabilized by reduction and oxidation of the cuticle (Finney and Ruvkun, 1990). Permeabilized animals were incubated at 37° C. for 8 hr with a hundred fold dilution of monoclonal antibody MH27 (provided by J. Preiss), and then for 12 hr with a hundred fold dilution of secondary antibody (rhodamine isothiocyanate conjugate goat anti-mouse, Boehringer Mannheim Biochemical, Indianapolis Ind.). Stained animals were mounted in a solution containing 30mM Tris pH7.5, 70% glycerol, and 2% N-propylgalate. Observation and photography were performed with a Zeiss Axioplan microscope equipped for epifluorescence.

Visualization of Hypodermal Cell Boundaries

To visualize the SET compartment in the male tail, late L4 larval males were mounted for Nomarski microscopy (Sulston and Hodgkin, 1988) in 0.25% sodium dodecyl-sulfate (Austin and Kenyon, 1994). Animals were immediately observed at 1000×. The boundary of hypodermal cells, including the SET, gradually became visible and then started to deteriorate. When the boundaries were clear, SET nuclei were counted and photographed.

Transformation Rescue of mab-21

Cosmids for transformation rescue of mab-21 were obtained from R. Shownkeen and A. Coulson (MRC Laboratory of Molecular Biology, Cambridge, UK). Microinjection of cloned DNA into hermaphrodite gonads was performed following the procedure of Mello et al. (1991). The number of cosmids including those listed in FIG. 4B were individually injected at a concentration of 15 µg/ml together with the dominant rol-6(su1006) marker carried on plasmid pRF4 (Kramer et al., 1990) at a concentration of 20 µg/ml. mab-21 (bx53); him-5 (e1490) (EM128) was the host of microinjection. Rol males appearing among the progeny of injected hermaphrodites were scored for ray 6 to 4 transformation phenotype. A minimal rescuing genomic BamHI-SacI fragment was identified by deletion analysis (EM#227) (FIG. 4B), and its sequence determined (Sequenase Kit, US Biochemicals).

To confirm the identification of the mab-21 locus, a frame shift mutation was introduced into the open reading frame present in EM#219 (FIG. 4B). A unique EcoRI site in the 3' end of the open reading frame was filled in with Klenow polymerase and religated. This resulted in generation of a premature translation termination codon at position 311, and consequently a truncated MAB-21 conceptual protein lacking 79 amino acids from the carboxyl terminus. Transformation with DNA carrying this frame shift mutation failed to result in rescue of -mab-21(bx53) (0/54 Rol males showed a wild type ray 6 phenotype).

Isolation of cDNA Clones and Heat Shock-Induced Expression

Figure 5:
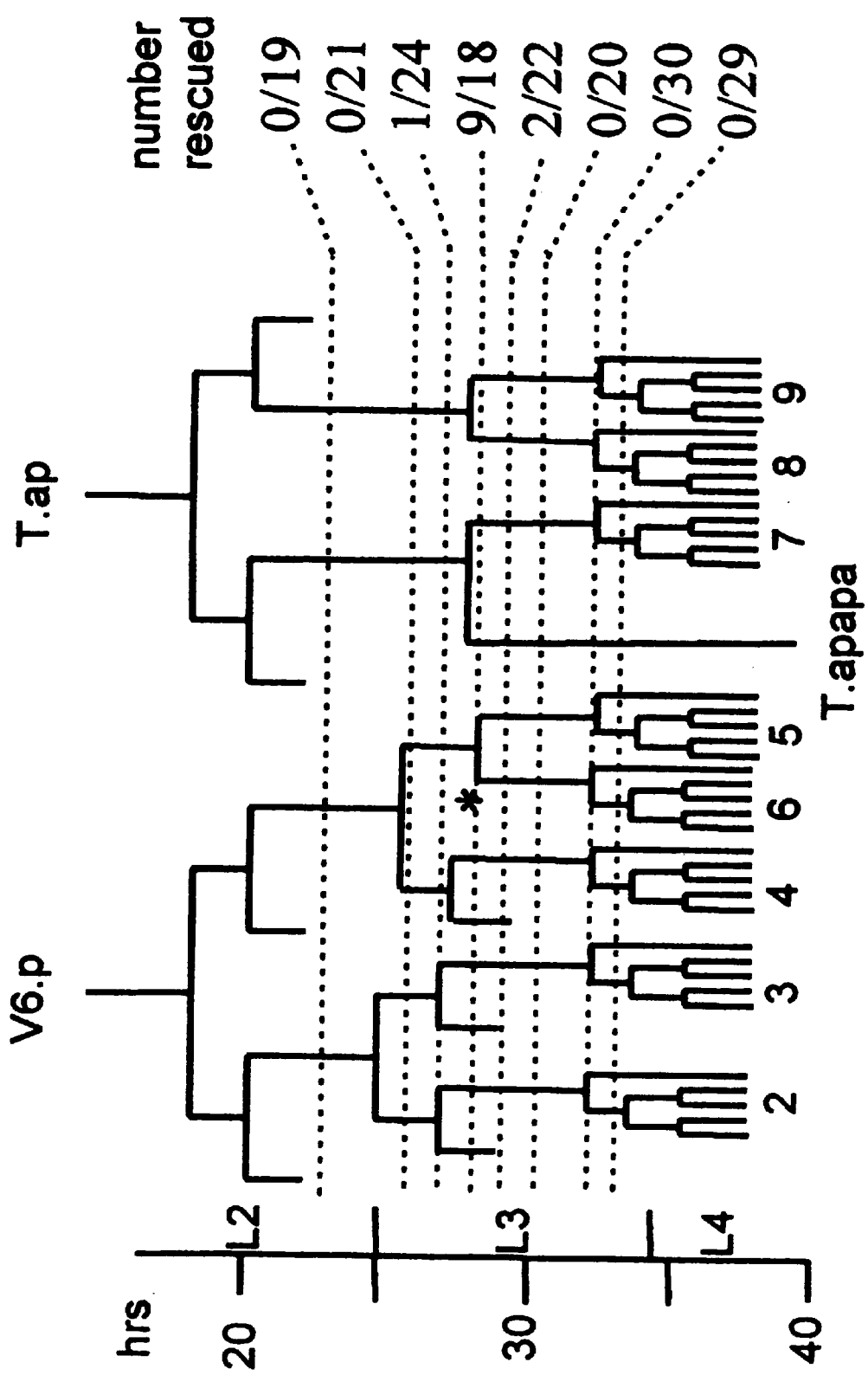
FIG. 5: Rescue of the mab-21 mutant phenotype by expression of a transgene from a heat shock promoter. Hours of postembryonic development and larval stages are shown at the left. At the stages of the cell lineage indicated by the dashed lines, animals were placed at 32° C. for 3 hr, then returned to 20° C. The number of adult males with fully wild type tails is shown to the right. R6 is marked by *.

A *C. elegans* lamda cDNA library (Palazzolo et al., 1990) was screened with EM#219 (FIG. 4B). Plasmid derivatives of the positive phage clones were obtained following the procedure described by Palazzolo et al. (1990). Inserts were sequenced with Sequenase Kit (US Biochemicals). DNA sequences were analyzed with GCG sequence analysis software (Sequence Analysis Software Package by Genetics Computer Group, Inc., [Devereux et al., 1984]). The Genbank Accession Number for the mab-21 cDNA sequence is U19861.

cDNA inserts A, B, and C (FIG. 4B) were released by digestion with ApaI and SacI and subcloned into pPD49.78 (Fire et al., 1990), which allows their expression from the heat shock promoter hsp16.2 (generating respectively plasmids EM#230, EM#231, and EM#220). After cotransformation with pRF4, stable integrated lines were isolated by gamma ray radiation (95 rads per minute for 40 minutes). For heat shock of synchronized populations, eggs were isolated with sodium hypochlorite and allowed to hatch into buffer (Sulston and Hodgkin, 1988). Synchronized, arrested L1 larvae were transferred after 24 hours to 50 mm plates seeded with bacteria and allowed to develop at 20° C. At various times during development, plates were shifted to 32° C. for 3 hours and returned to 20° C. Adult Rol males were scored for ray fusion phenotype. For determining the effective heat shock interval with individual animals, single animals were randomly picked and staged by observation with Nomarski microscopy. They were then heat shocked for 3 hours at 32° C., allowed to recover and develop at 20° C., and their adult phenotype recorded (FIG. 5).

Mosaic Analysis

Figure 6:
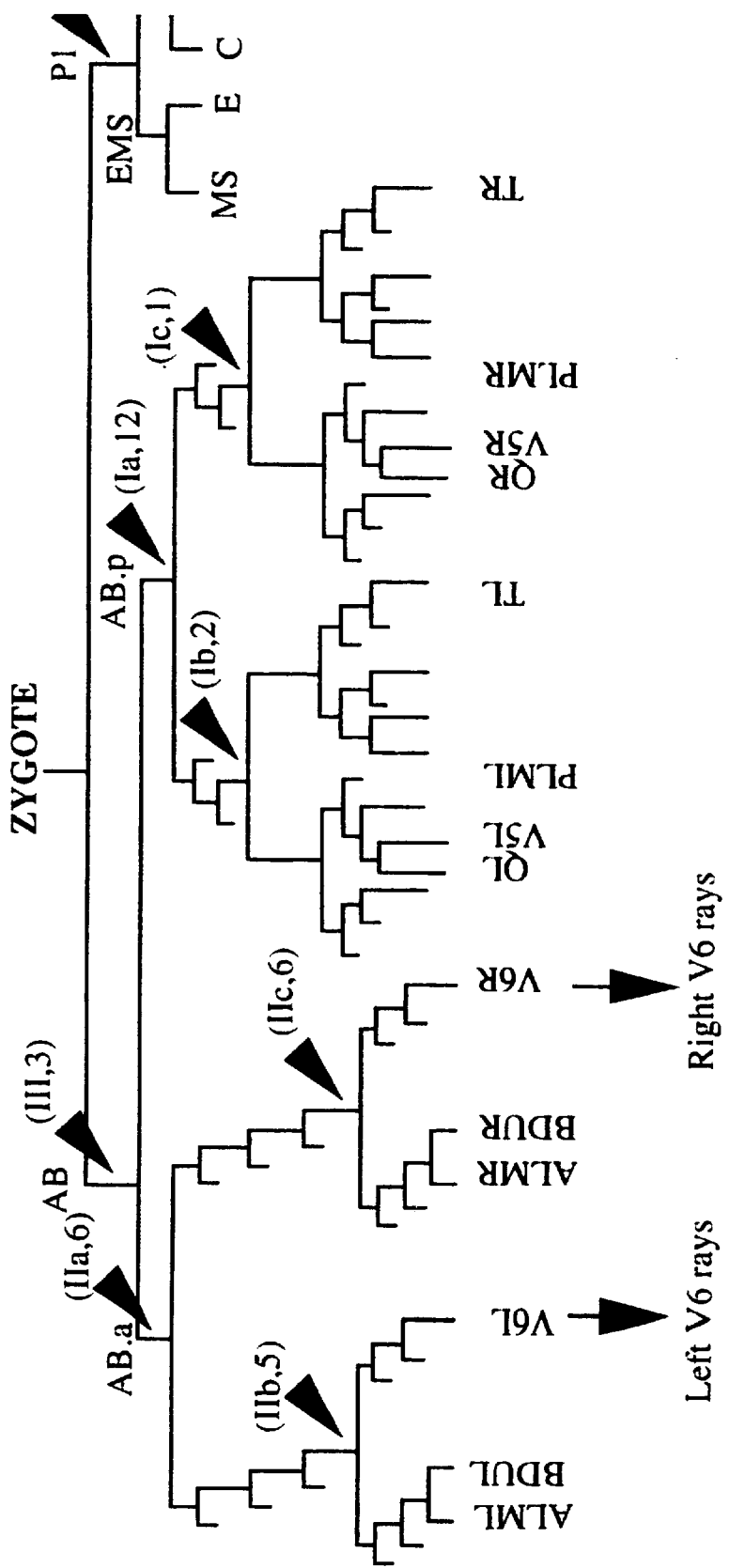
FIG. 6: Mosaic analysis of mab-21. The lineage diagram shows the relationships between V5, V6, T and the cells in which the Ncl phenotype was used to score for the presence of the free duplication. The arrowheads identify the point of loss of duplication. The arrowheads identify the point of loss of duplication in various classes of mosaics (number in parentheses is the number of animals scored in each class). When the point of duplication loss is ambiguous, the arrowhead points to the last cell in which the loss could have occurred.

Mosaic analysis (Herman, 1984, 1989) for determination of the focus of mab-21 gene activity was carried out in strain EM289, genotype mab-21 (bx53) ncl-1 (e1865) unc-36 (e251) III;him-5 (e1490)V;sDp3(III;f). The free duplication sDp3(III;f) (Rosenbluth et al., 1985) carries wild type copies of the LGIII genes and hence EM289 is generally nonMab nonUnc and nonNcl in phenotype. Genetic mosaics arise by spontaneous loss of the free duplication. ncl-1(e1865) results in enlarged nucleoli; its activity is cell-autonomous (Herman, 1989). The unc-36(e251) mutation results in very slow movement, probably due to loss of the gene in motor neurons; its focus of activity is among descendants of AB or AB.p (Kenyon, 1986; Herman, 1989). Mosaic males were identified as Unc animals with wild type rays, or as nonUnc or semiUnc animals with Mab rays. Because displacement of ray cell bodies during L4 morphogenesis of the male tail prevents identification of ray cells in the adult, the point of duplication loss was determined by examining the nuclei of lineally related cells (FIG. 6). The Ncl phenotype of PLM (L/R), V5.pa postdeirid neurons, and Q-derived neurons were scored to infer duplication loss in the AB.p branch; the Ncl phenotype in ALM(L/R) and BDU(L/R) were scored to infer loss in the AB.a branch. Loss of the duplication in the P1 lineage was scored by the Ncl phenotype of body muscle cells, pharyngeal neurons, and coelomocytes. In 4 putative mosaic animals, no Ncl nucleoli could be found in the cells examined. The observed mab-21 phenotype observed on one side in these animals could be accounted for by loss of the duplication in a subset of cells within the V6 lineage (in two cases within AB.apppap or one of its descendants, in two cases within AB.arpppp or one of its descendants); these are not shown in FIG. 6.

Figure 1A:
FIGS. 1A–1D: Morphology and development of wild type and mab-21 male tails.
Figure 2A:
FIGS. 2A–2N: Ultrastructure of wild type and fused rays.
Figure 2B:
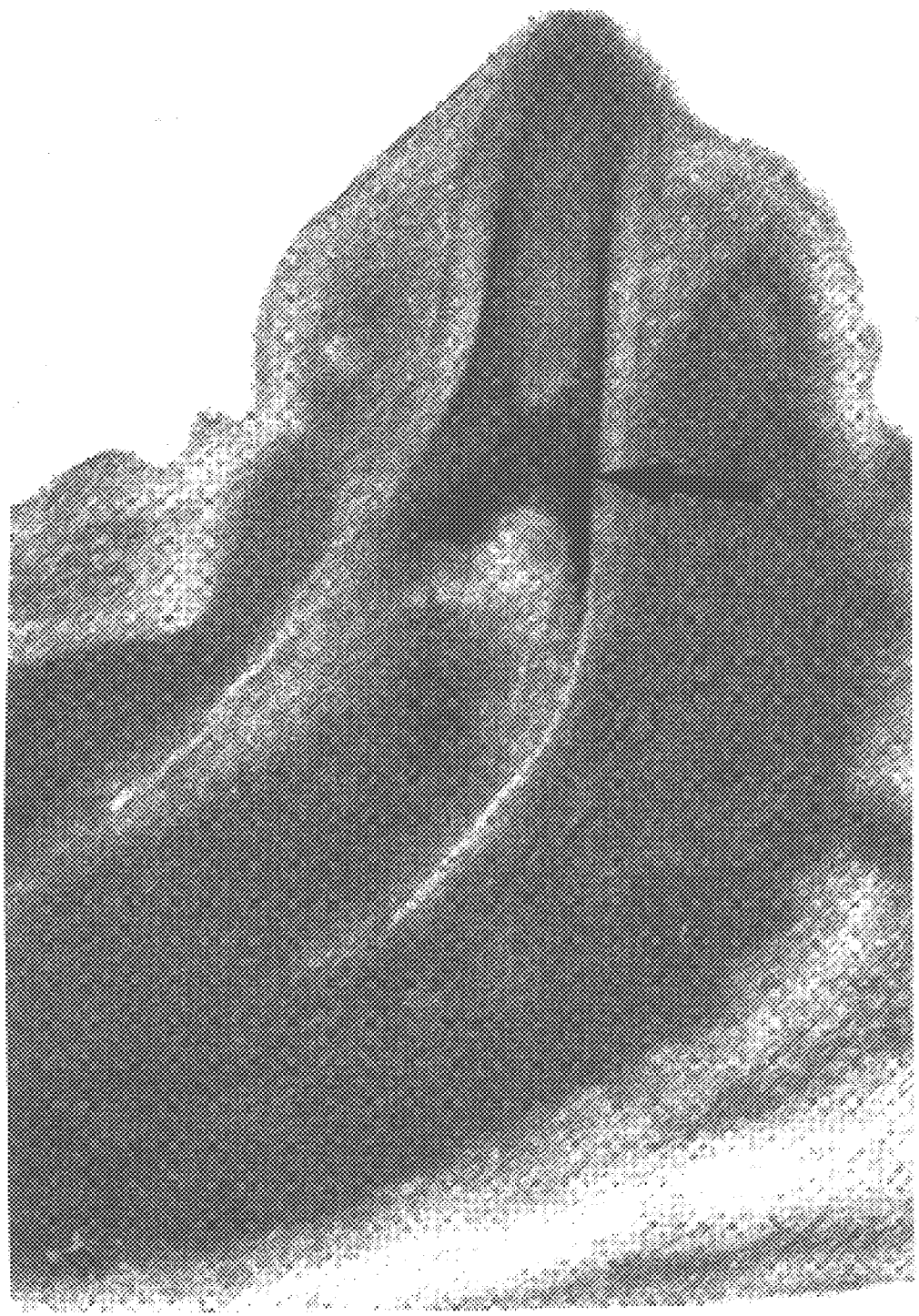
Figure 2D:
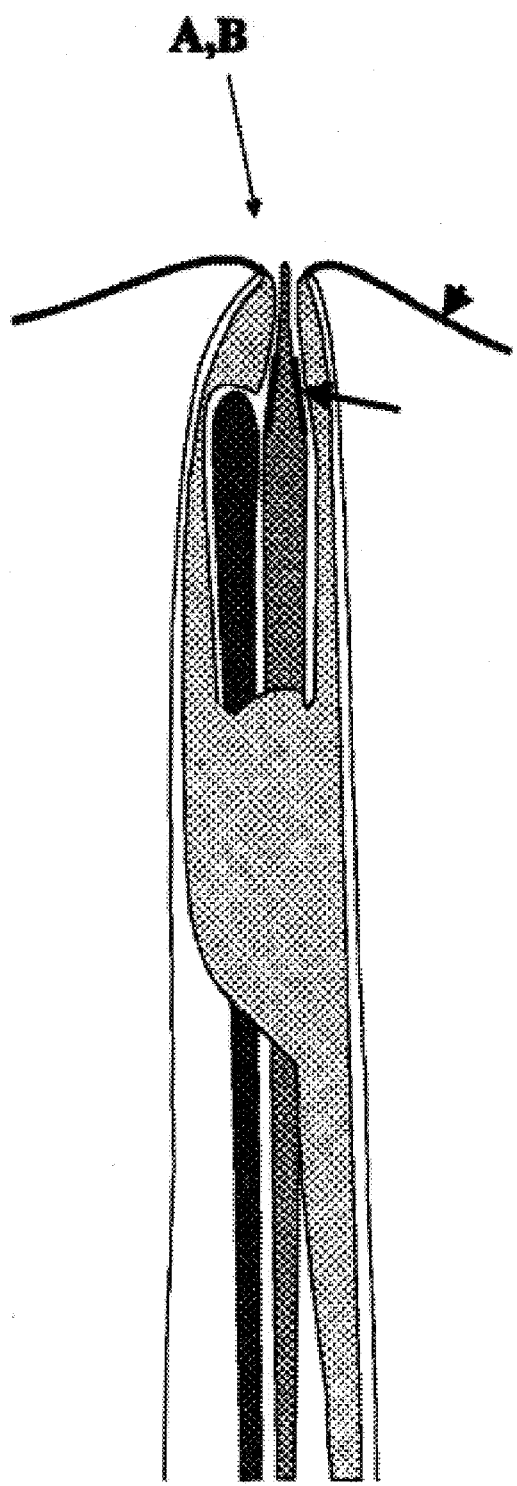
FIG. 2D. Diagram of the tip of a typical ray in wild type other than ray 6, viewed from the dorsal or ventral side (perpendicular to the fan). The density surrounding RnB near the tip is indicated by an arrow, the edge of the fan by an arrowhead. A channel within the structural cell enclosed the distal portion of both neuronal processes. Ray 6 is similar but lacks the open channel (or has only a very narrow channel through the structural cell not containing the ending of a neuron). The plane of section in A and B is indicated.
Figure 2E:
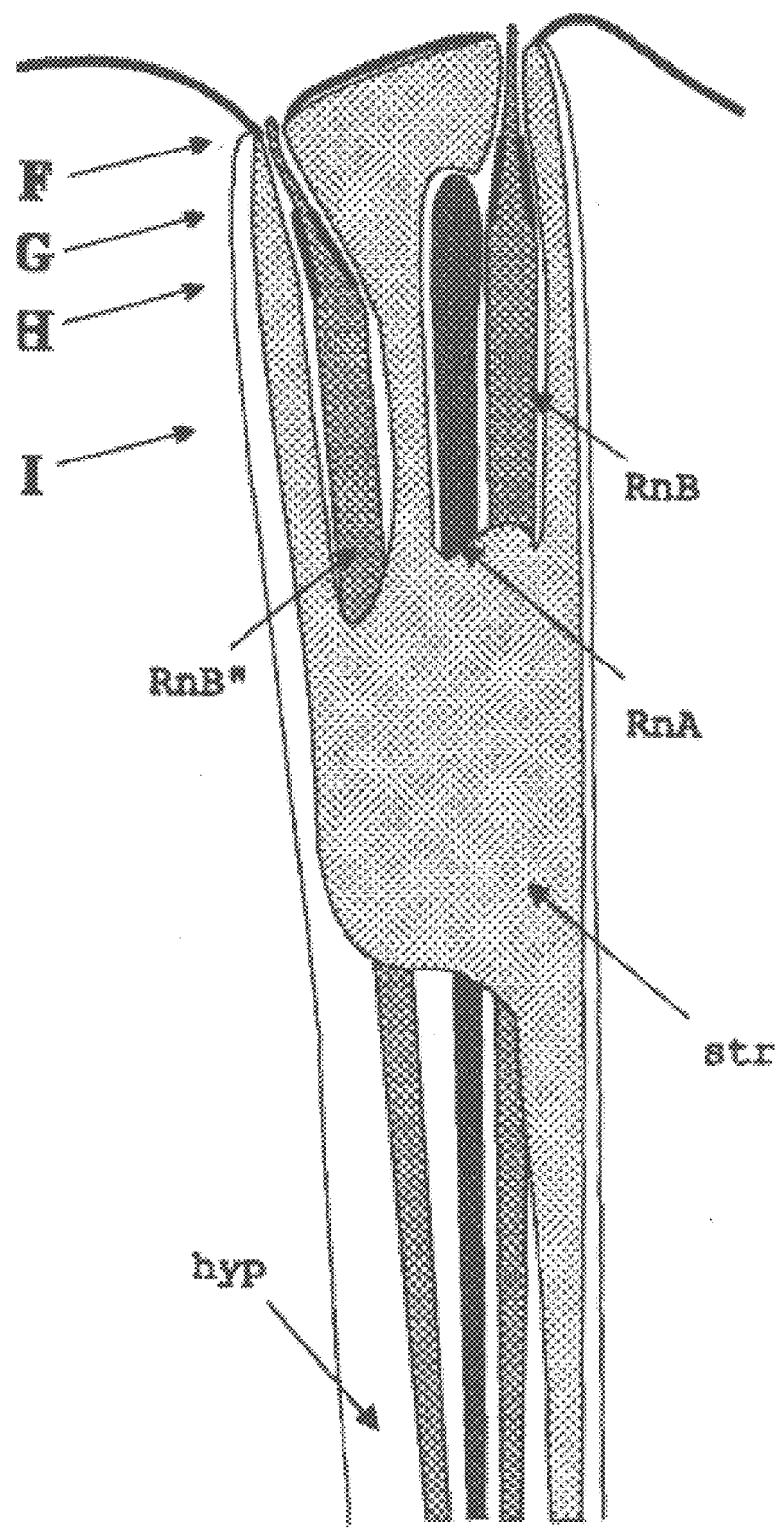
FIG. 2E. Diagram of the tip of a fused 4–6 ray in mab-21. Generally, three dendritic processes are present in two channels (n=13/14), RnA being missing from one channel. In one animal, a fourth dendritic process was present in a third channel. The positions of the sections shown in F–I are indicated.
Figure 2F:
FIGS. 2F–2I. Sections through a fused 4–6 ray in mab-21. Two channels are present in a single structural cell, one with two neuronal processes and one with one. A process with the ultrastructure of a B-type neuron, each with a density similar to that found in ray 4 in wild type (arrows in G and H), extends into each of two openings. The levels of these sections is shown in E.
Figure 2G:
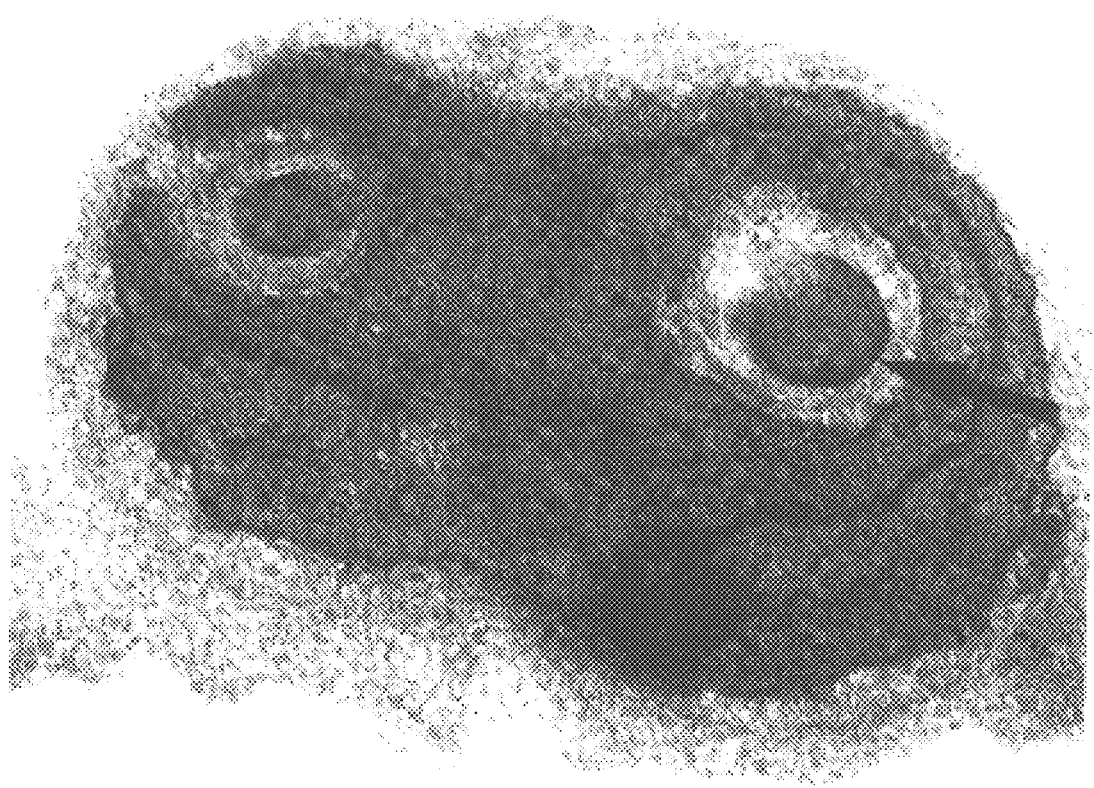
Figure 2H:
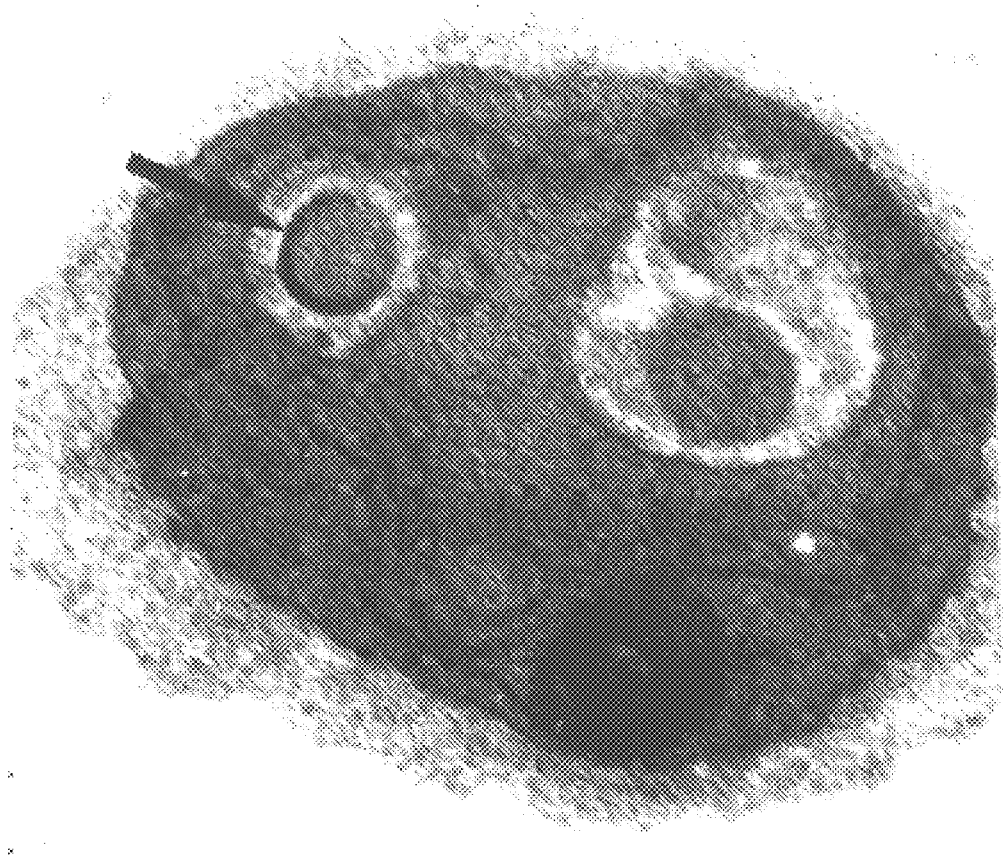
Figure 2I:
Figure 2J:
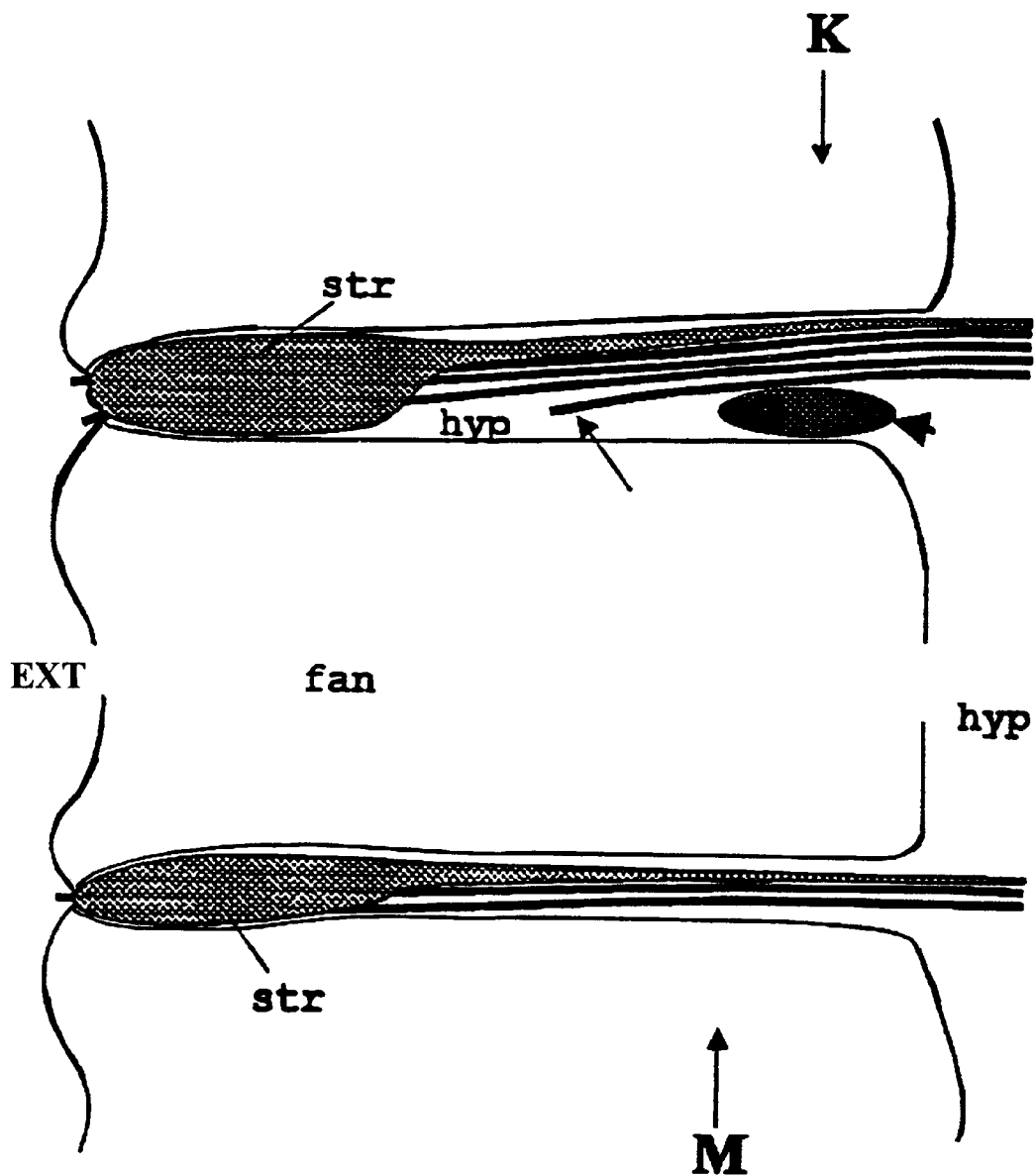
FIG. 2J. Schematic diagrams of complete rays, a fused 4–6 ray (top) and a normal ray (bottom). In the one fused ray reconstructed, the A-type neuron partially entered the ray as shown (thin arrow). A nucleus typically present within the base of the ray is indicated (arrowhead). The levels of the sections shown in K and M are indicated.
Figure 2K:
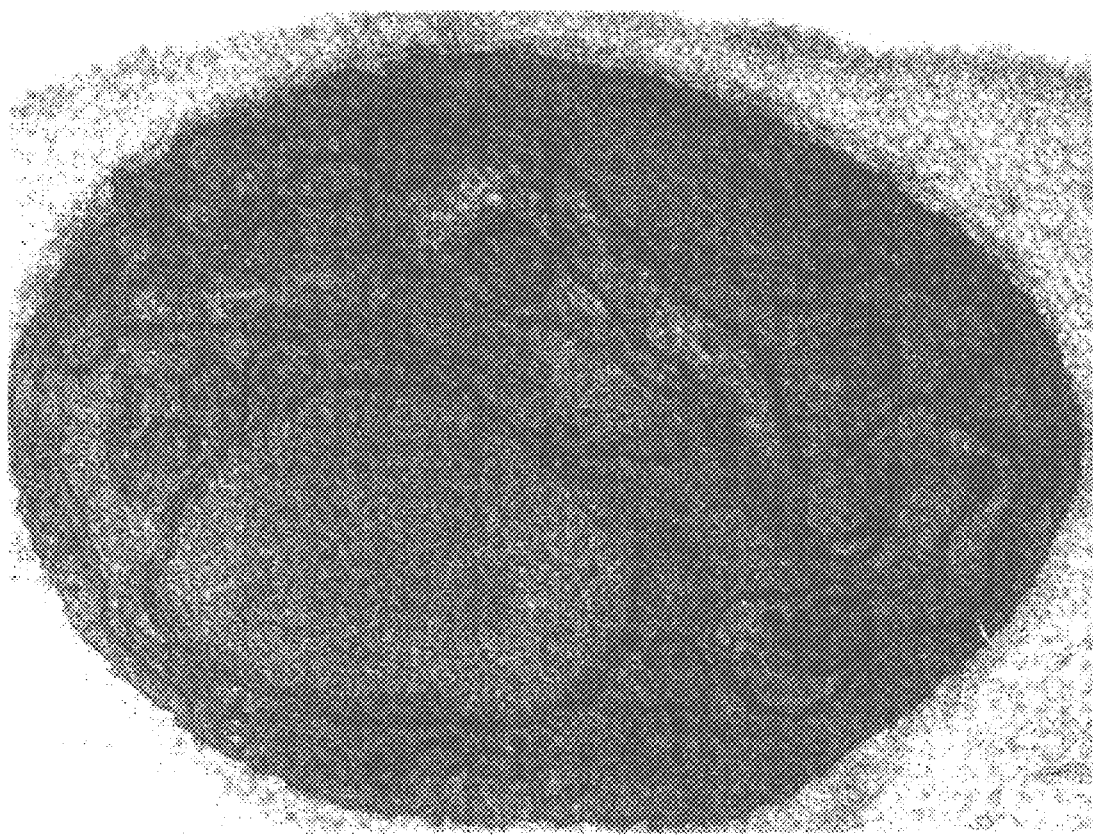
FIGS. 2K–2L. Representative cross section of a used 4–6 ray in mab-21. The processes of 4 neurons, two B type, one A-type, and one presumed A-type that fails to reach the tip, are present, as well as the process of a single structural cell. The bulk of the ray consists of the hypodermal syncytium, hyp7. The level of the section is indicated in J.
Figure 2L:
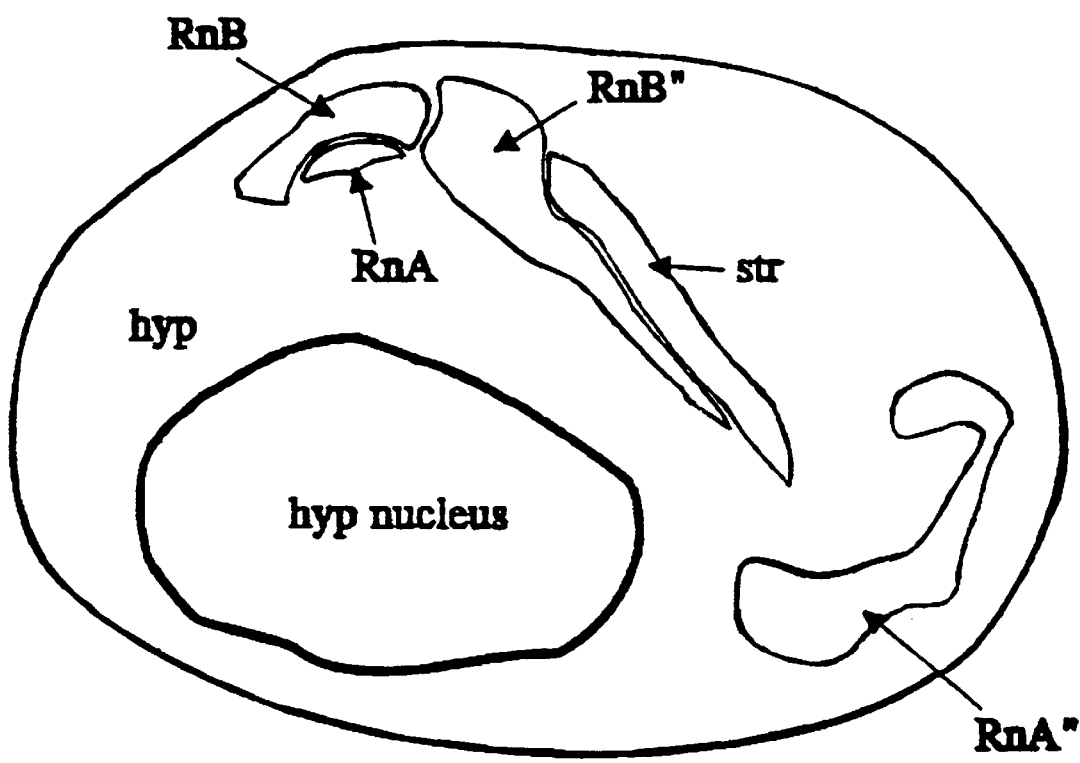
Figure 2M:
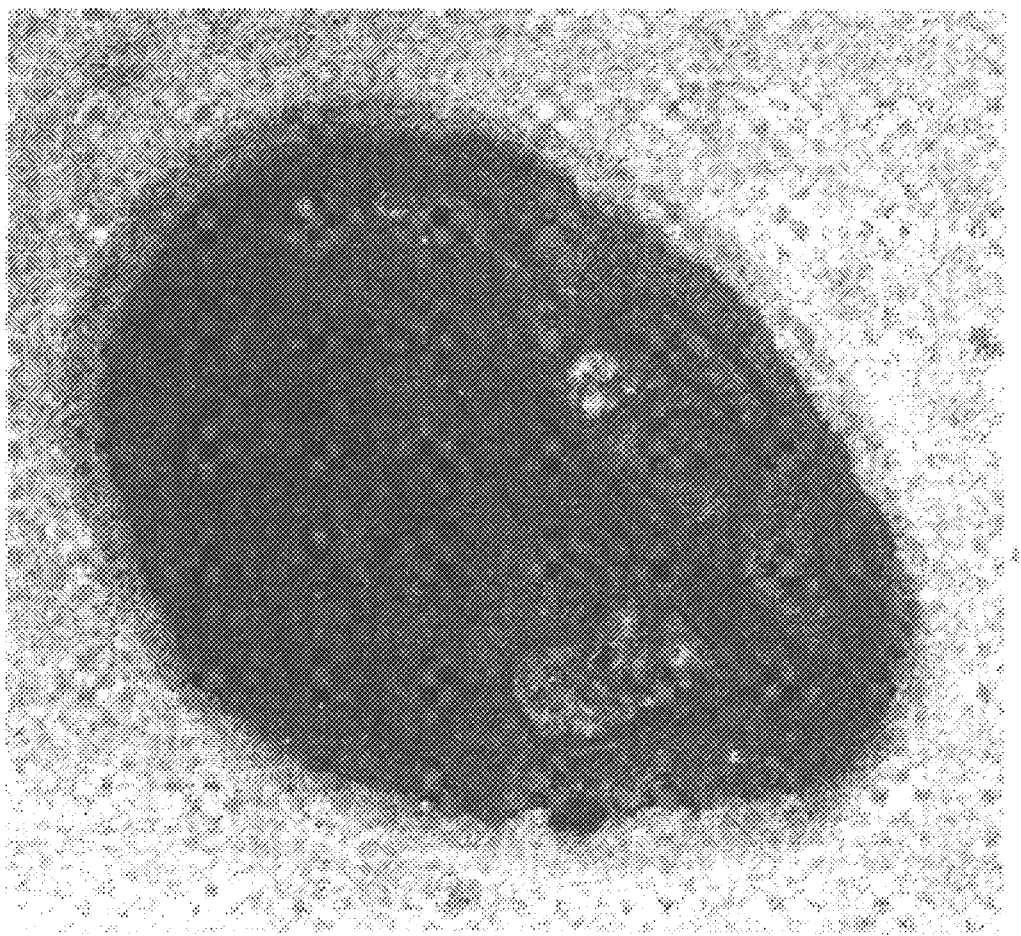
Figure 2N:
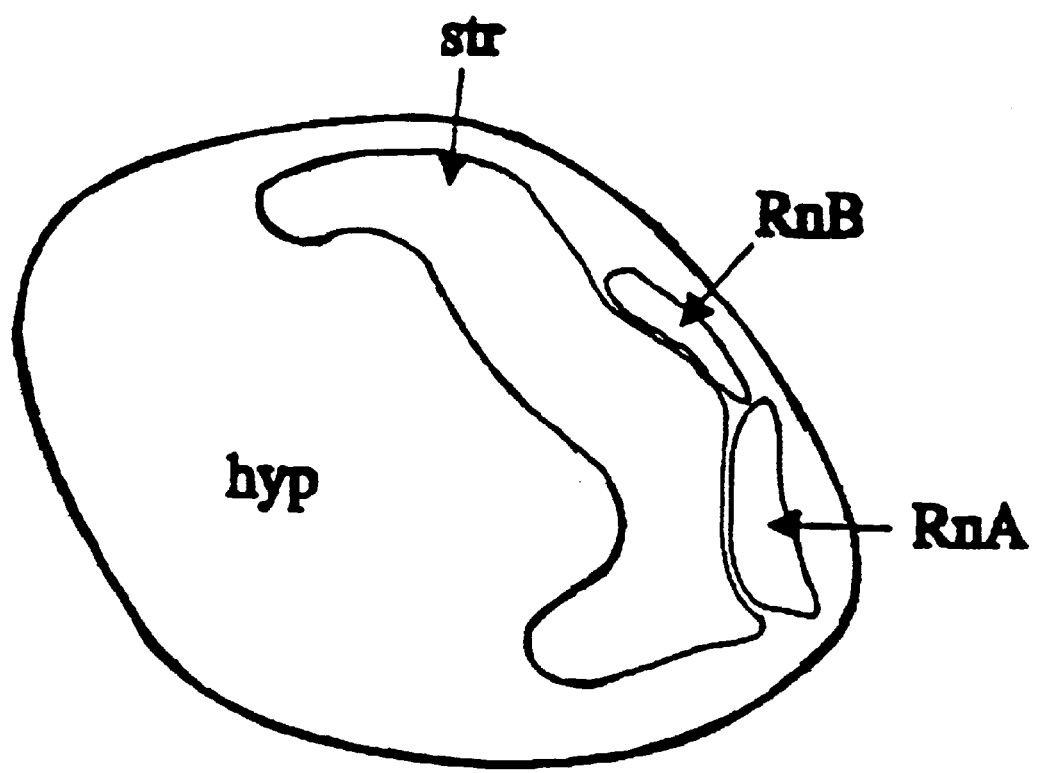
Figure 3A:
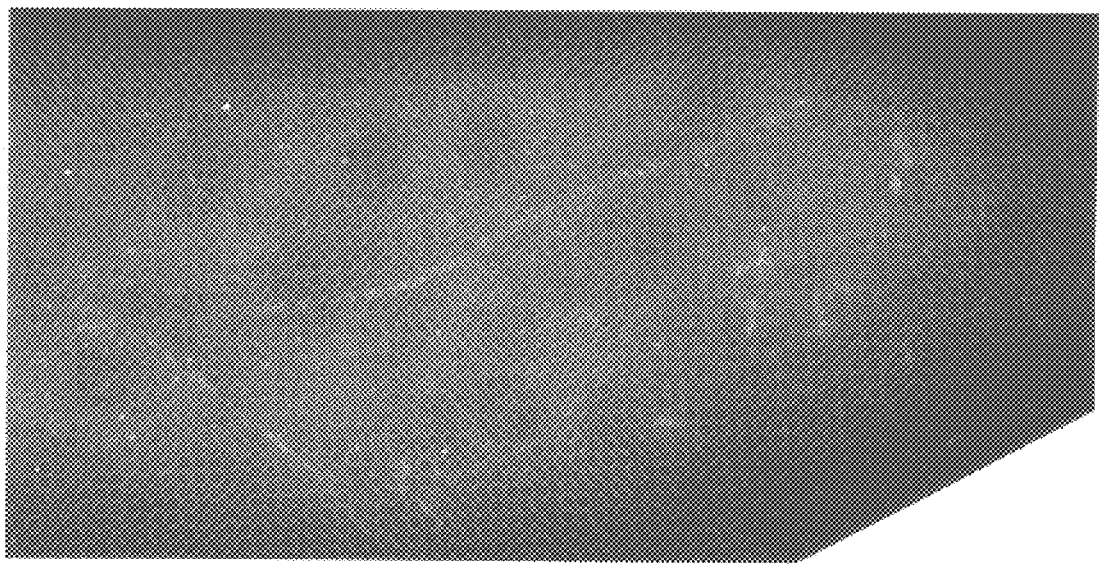
FIGS. 3A–3F: In mab-21, R6.p fuses with the tail seam (SET).
Figure 3B:
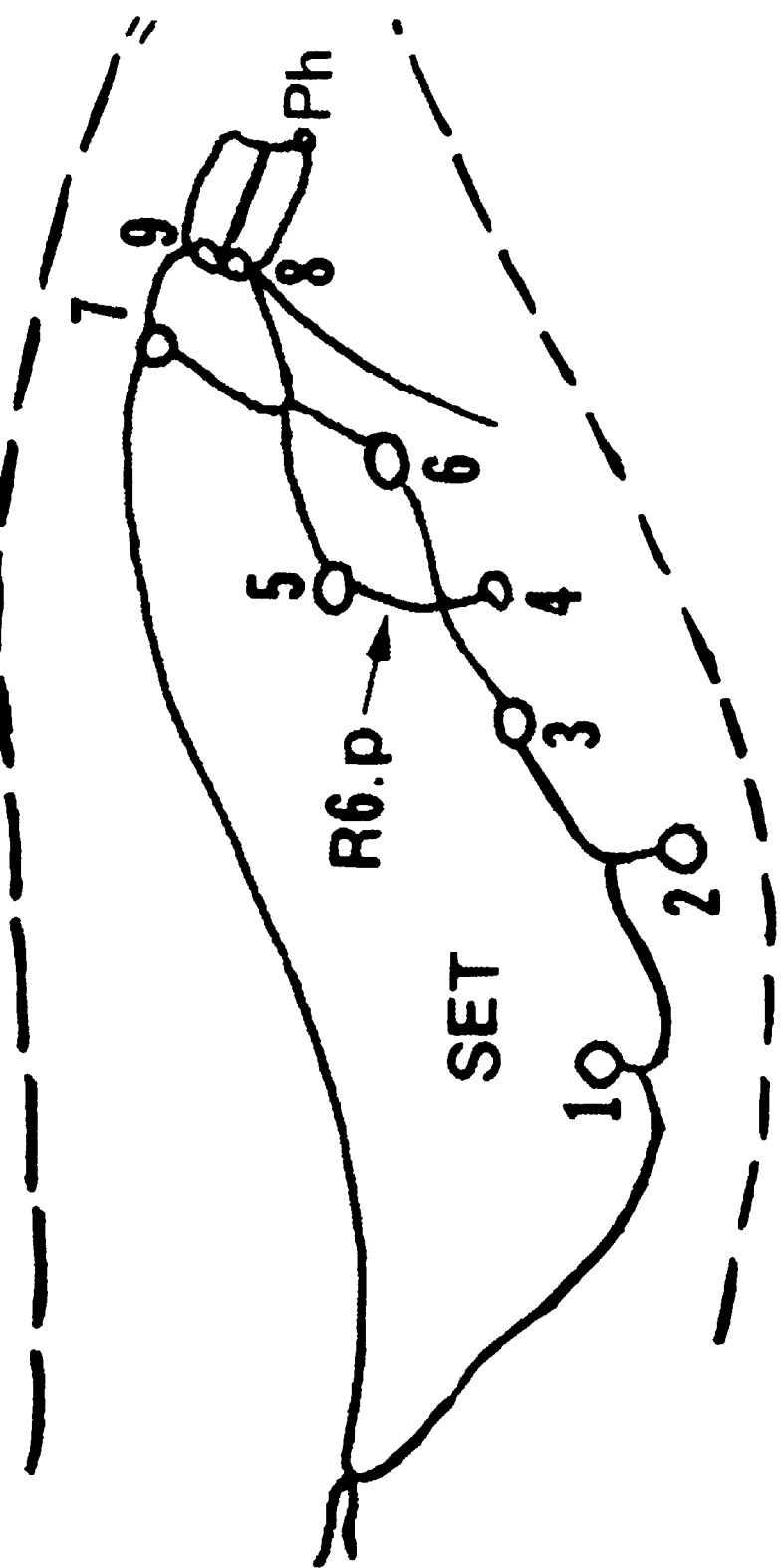
Figure 3C:
Figure 3D:
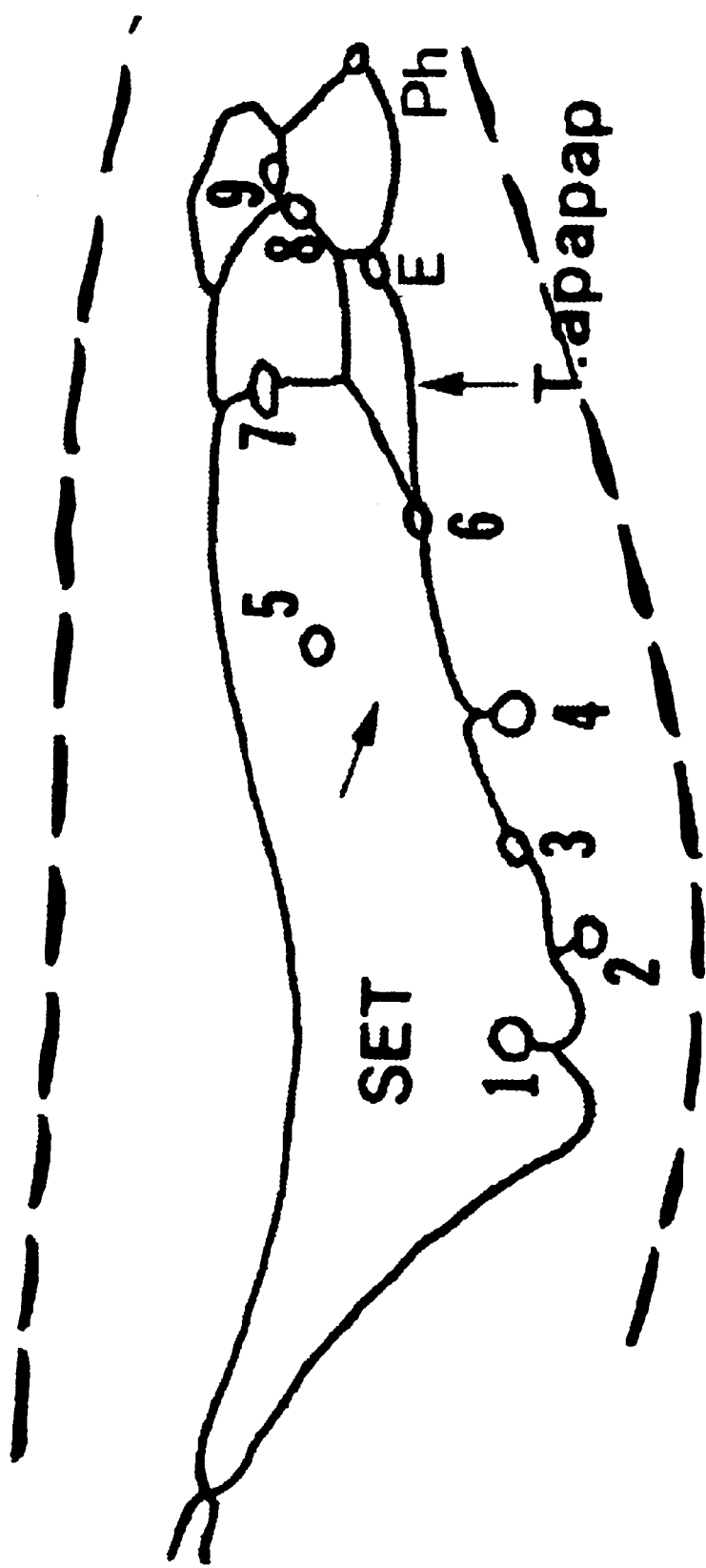
Figure 3E:
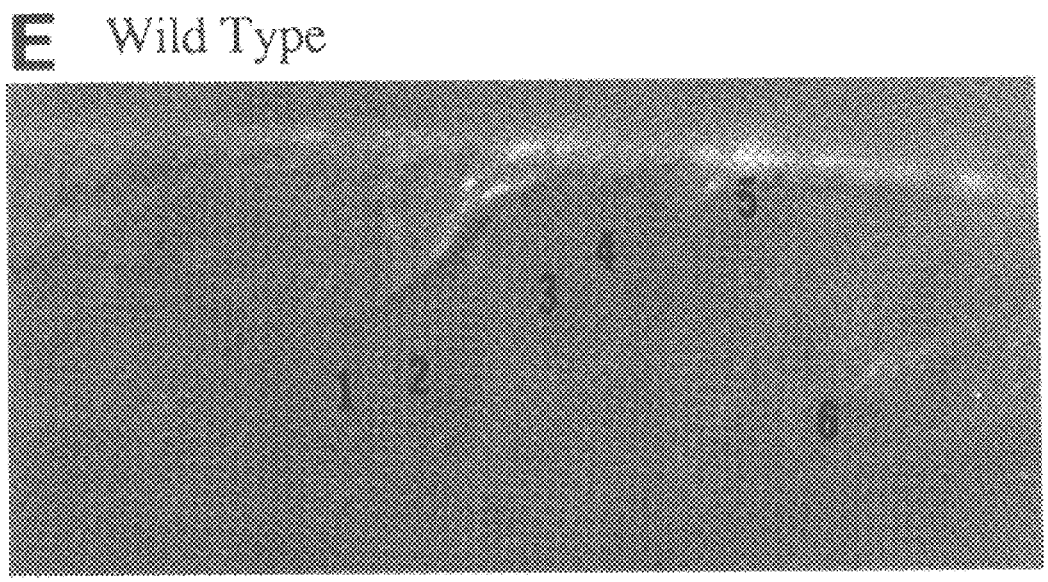
Figure 3F:
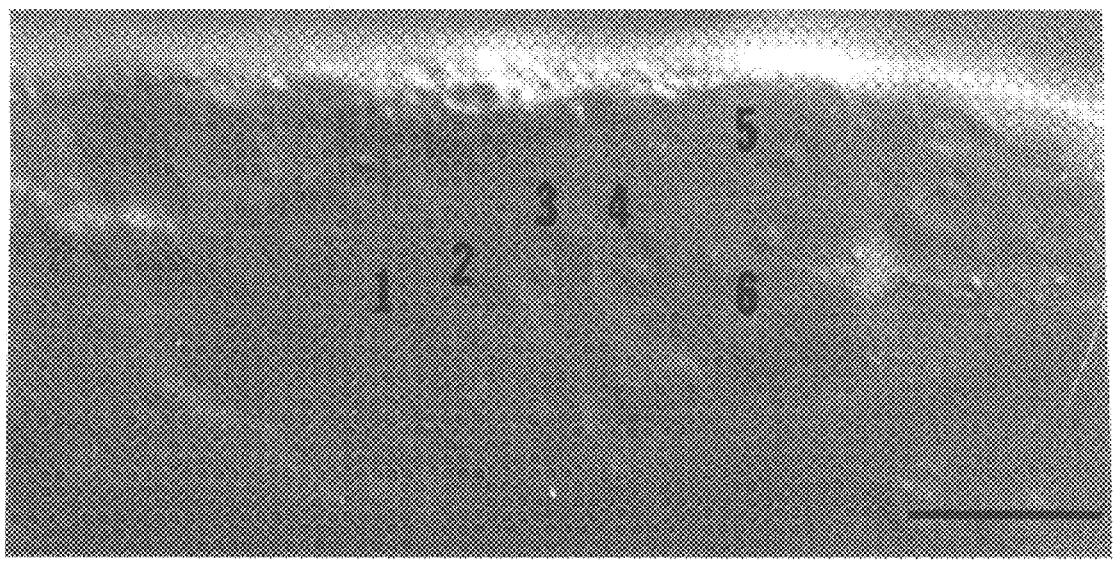

Experimental Results mab-21 is Required for the Choice of Alternate Fates by Several Cells in the Male Tail Mutations in the gene mab-21 were identified because of their effects on differentiation of a single pair of sensory rays in the *C. elegans* adult male tail (Baird et al., 1991). It is found that mab-21 mutations affected the differentiation of two cells in ray 6, as well as the fusion properties of the hypodermal cell generated by the ray 6 sublineage. mab-21 mutations also transform a nearby hypodermal cell into a neuroblast cell that expresses the ray sublineage and generates a ray. The *C. elegans* male has several specialized posterior structures and organs necessary for copulation with the hermaphrodite. Among these are a set of nine bilaterally symmetrical pairs of sensory rays, which project outward from the body within an acellular fan (FIG. 1A). The ultrastructure of the rays has been described by Sulston et al. (1980), and is illustrated in FIG. 2. Each ray consists of a cone or cylindar of hypodermis containing the dendritic processes of two ultrastructurally distinguishable neurons (RnA, RnB, n=1–9), together with the process of a support cell (called the structural cell, Rnst) (FIGS. 2J,N). The support cell is joined to the hypodermis at the tip of the ray and surrounds and holds the dendritic endings of the neurons, one of which, RnB, generally faces an opening to the exterior (FIGS. 2A,D). In wild type males, the rays are of identical morphology with one exception: the sixth ray counting from anterior to posterior, ray 6, is fatter and more conical in shape than the others rays (FIG. 1A). Ray 6 also fails to open to the exterior or is open only through a thin channel, and has a B neuron that differs slightly in ultrastructure from the B neurons of the other rays (Sulston et al., 1980) (FIG. 2C).

Figure 1B:
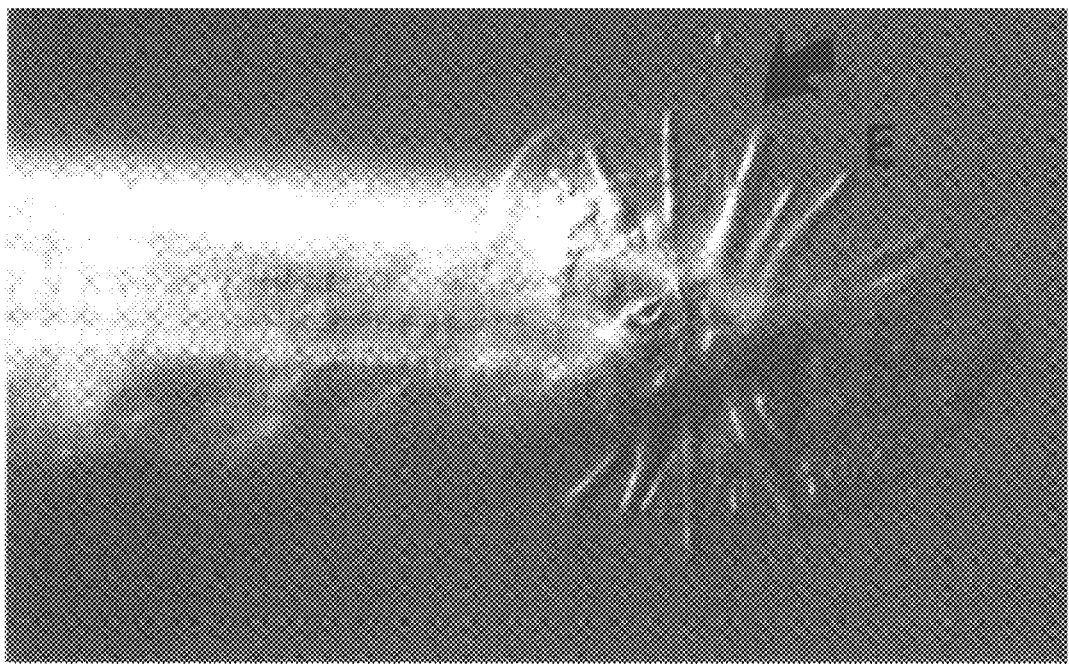
Figure 1C:
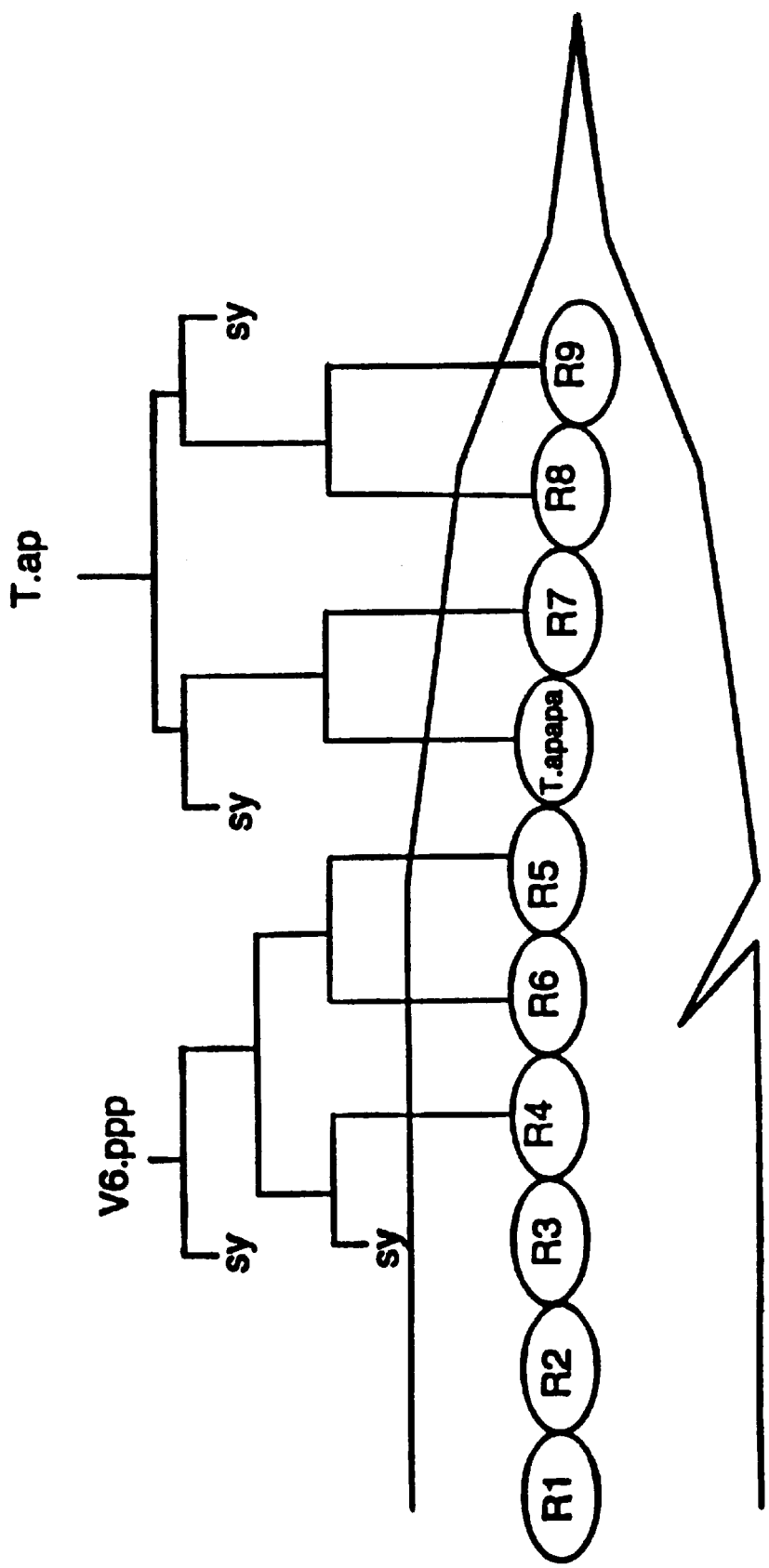
Figure 1D:
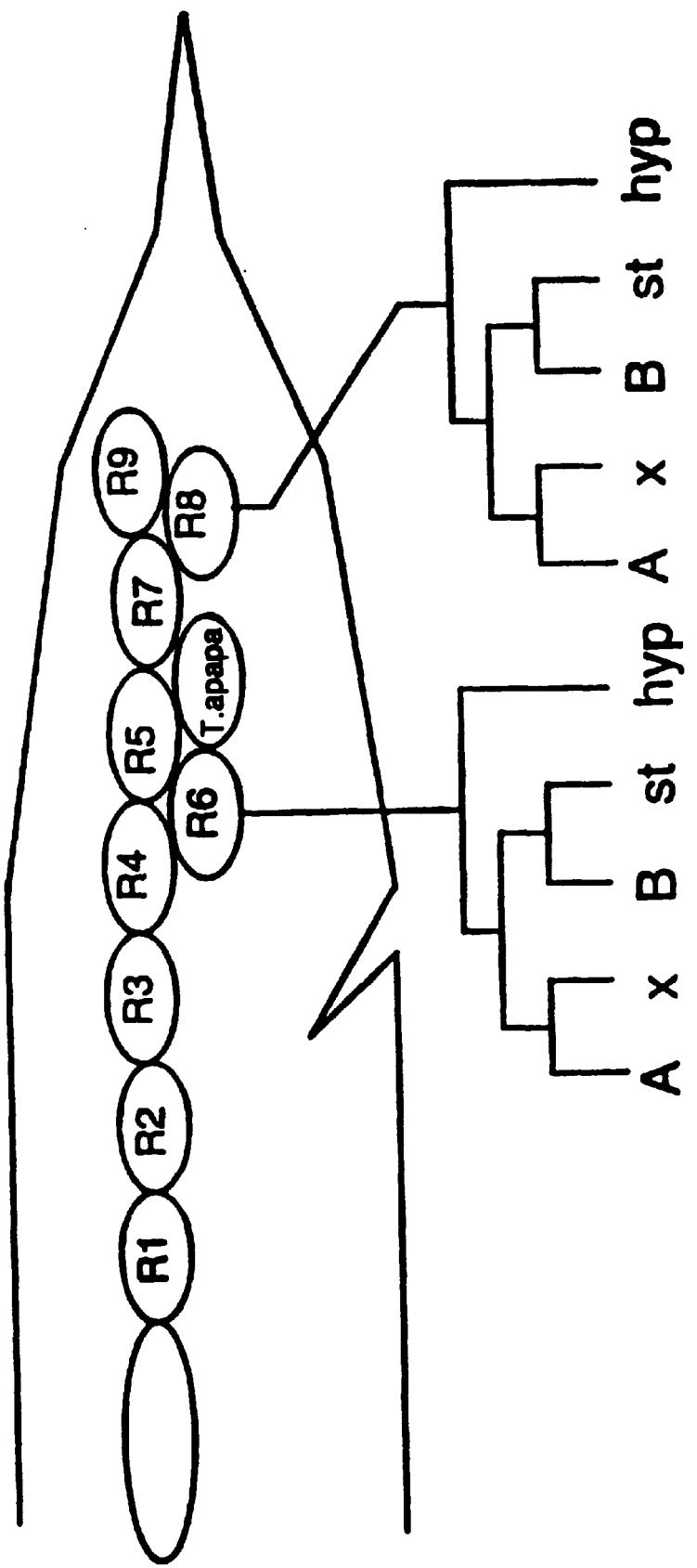

In mab-21 mutants, the most obvious phenotype is that the distinctive conical ray 6, is absent, and a large ray of uniform diameter replaces ray 4 (FIG. 1B). The large new ray consists of a fusion of rays 6 and 4, and contains the cells normally found in these two rays, as demonstrated by several lines of evidence. First, in mab-21 mutants the cell lineages leading to rays 4 and 6 are unaffected. In wild type, the three cells of each ray plus one hypodermal cell are generated as products of the ray sublineage. The ray sublineage is expressed by ray precursor cells (Rn cells) (FIGS. 1C,D) (Sulston and Horvitz, 1977, Sulston et al., 1980). In mab-21 mutants, both R4 and R6 express the ray sublineage at the normal time (8/8 sides lineaged). Secondly, the large ray at the position of ray 4 extends from two adjacent papillae (not shown) and has two ray tips (FIG. 2F). Ray papillae and tips are structures formed by the ray structural cell and have a distinctive "ring-and-dot" morphology visible by Nomarski microscopy (Sulston et al., 1980). The presence of two ray papillae during L4 and two tips in the large ray suggests that the large ray contains two structural cells. These cells are apparently fused, as no cell boundaries separating them are visible in electron micrographs of the fused ray (FIGS. 2F–I,K). Thirdly, electron microscopy reveals that the large ray contains the processes of three or four neurons (FIGS. 2F–I,K). Two of the processes terminate respectively at each of the two openings and have the ultrastructure of B-type neurons, while two terminate within the ray and have the ultastructure of A-type neurons.

Fusion of ray 6 to ray 4 in mab-21 mutants appears to be the result of altered properties of ray 6, and in particular, of the ray 6 structural cell, R6st. Mutational changes affecting ray 6 alone can occasionally be seen when fusion of ray 6 with ray 4 does not occur. In 5% (n>600) of mab-21 mutant animals rays 4 and 6 do not fuse. In these animals, ray 4 appears to be unaffected, while ray 6 lies between rays 4 and 5 anterior of its normal position. In such animals, ray 6 does not have a conical morphology, but instead has a uniformly thin morphology similar to the other rays. The unique conical morphology of ray 6 in wild type is determined by R6st (Y. Zhang and S. W. Emmons, in preparation). Altered ray 6 position is likely to result from altered interactions between R6st and surrounding hypodermal cells (Baird et al., 1991). Fusion of ray 4 and ray 6 in mab-21 mutants could be a consequence of misplacement of ray 6 to a position adjacent to ray 4, or could result because cell recognition functions expressed by cells of ray 6, ray 4, or both, are altered.

In addition to affecting properties of R6st, mab-21 mutations affect the ultrastructure of R6B. In wild type, the B neurons of most rays are characterized by having a thin lip that is exposed to the exterior, and by the presence of an extracellular dense matrix material where the tip narrows (FIGS. 2A, B). In ray 7 in wild type, in which there is either no opening or only a narrow channel opening to the exterior (data not shown), the B neuron lacks this dense material (FIG. 2C). In mab-21 mutants, fused rays have two openings, each containing the tip of a B-type neuron. Both of these neurons are surrounded by the dense material normally characteristic of all the rays except ray 6 (FIGS. 2G, H). This in mab-21 mutants, the ultrastructure of the ending of R6B has been transformed to that characteristic of the B neurons of the other rays. A second unique ultrastructural property of R6B in wild type, lack of dilated cisternae in the cell body (Sulston et al., 1980), was not examined.

A third cell affected in mab-21 mutants is the hypodermal cell generated by the ray 6 sublineage (R6.p). At the end of the L4 larval stage, R6.p normally fuses with the large hypodermal syncytium, hyp7, covering most of the body (Sulston et al., 1980). In mab-21 mutants, R6.p instead fuses with R1.p–R5.p (n=15/15), thus becoming part of the tail seam (SET) (FIG. 3).

Finally, in mab-21 mutants, a hypodermal cell lying adjacent to ray 6 is transformed into a ray neuroblast. In wild type, the rays are generated by nine pairs of ray precursor cells. These are descended from three embryonic hypodermal blast cells denoted V5 (ray 1), V6 (rays 2–6), and T (rays 7–9). In mab-21 mutants, an additional descendant cell of T, T.apapa, the anterior sister of R7, is often (45%, n>600) transformed from a hypodermal cell into a ray precursor cell and expresses the ray sublineage. Thus, mab-21 mutant animals can have 10 instead of 9 rays (FIG. 1B). The T.apapa-derived ray will sometimes be referred to as the "ectopic" ray.

Altogether, the mab-21 male tail phenotype can be accounted for by the affects on the fates of the four cells, R6st, R6B, R6.p and T.apapa. These affected cells are of diverse types, and therefore nab-21 does not appear to be required for expression of any particular cell fate. In each case, the affected cells choose alternate cell fates normally assumed by neighboring cells and appear to execute those alternate fates correctly. The cells affected by mab-21 mutations have in common that they lie adjacent to one another in a restricted region of the lateral epidermis of the male tail, and differentiate during the late L3 and L4 larval stages. Therefore it appears most likely that mab-21 is required for a localized pattern formation mechanism that causes these cells to choose their wild type fates.

All of the changes affecting cells of ray 6, together with the change in fusion partner of R6.p, can be parsimoniously interpreted as a change in the identity of the ray 6 precursor cell R6 to that of R4. T.apapa, like R6, is the anterior sister of a ray precursor cell (R7 in the case of T.apapa, R5 in the case of R6 [FIG. 1C]). R6 and T.apapa lie adjacent to each other ventral of the seam, and in mab-21 mutants each assumes the fate. mab-21 thus appears to act as one component of a pattern formation mechanism that assigns fates to at least two seam cells during the late L3 larval stage.

Additional mab-21 Mutant Phenotypes Suggest mab-21 Has Functions Outside the Tail Region of Males In addition to having ray defects in the male tail, srab-21 males and hermaphrodites are somewhat short and fat, are slightly uncoordinated, and have decreased fecundity. These pleiotropic defects imply that the action of mab-21 is not restricted to the tail hypodermis of males. The body length of mab-21 mutant adult hermaphrodites (856 mm±55 mm [n=30]), was intermediate between that of wild type (1024 mm±72 mm [n=30]) and dpy-17 (524 mm±56 mm [n=30]). The latter have short and fat bodies typical of a large number of dpy (dumpy) and sma (small) mutants. The shorter body length of mab-21 animals was not due to a growth rate defect, nor was the timing of developmental stages abnormal (data not shown). As the hypodermis and overlying cuticle play a key role in determining body shape in *C. elegans* (Priess and Hirsh, 1986; Levy et al., 1993) these results suggested that mab-21 might play a role in differentiation of the hypodermis.

mab-21 animals, particularly males, have an uncoordinated movement in backward locomotion. Upon being touched on the head, mab-21 males made a ventral bend at the tail during backward movement that was more severe than that of wild type males, resulting in a deep curving movement. A similar though less pronounced bend could be discerned in hermaphrodites. This backward Unc phenotype suggests a defect in the nervous system or possibly the posterior muscles in mab-21.

mab-21 hermaphrodites had a reduced brood size due to a reduced brood size due to a decreased number of laid eggs, suggesting the presence of a gonadal defect (average number of self progeny at 20° C. was 126 (18 for mab-21(bx53) ;him-5(e1490), n=10, average number for him-5(e1490) was 221 ( 18, n=10; results were similar with the other two mab-21 alleles). The eggs laid by mab-21 hermaphrodites failed to hatch in numbers (several percent) significantly higher than mab-21(+). Dead embryos were arrested from morphogenesis stage up to the end of embryogenesis, and had an apparently disrupted hypodermis. A few percent of hatched animals had a deformed Vab (variable abnormal) phenotype with deformities mostly in the region of the pharynx. mab-21 males sired fewer progeny in mating tests (data not shown), but it was difficult to determined whether this was due to a gonad defect or was because the uncoordinated movement described above disrupted mating.

mab-21 has an Essential Embryonic Function

In order to gain information about the possible null phenotype of mab-21, the phenotype that resulted when alleles of mab-21 were placed over a deficiency was determined. Mapping experiments (Materials and Methods) placed mab-21 on the left arm of linkage group III between unc-79 and pal-1 (FIG. 4A). It was attempted to construct the heterozygote carrying mab-21(bx53) over the deficiency yDf10, but found that progeny of the expected phenotype were absent from the cross (Table 1).

TABLE 1

Result of crossing mab-21 to a deficiency

| Male gametes Result | Hermaphrodite gametes | | |
|---|---|---|---|
| | unc-93 dpy-17 + | yDf10 + unc − 32 | |
| Cross 1 | | | |
| mab-21 + | nonUncnonDpy | MabnonUnc | 305 nonUnc |
| mab-21 unc-32 | nonUncnonDpy | MabUnc | 0 Unc |
| Cross 2 | | | |
| + + | nonUncnonDpy | nonUnc | 426 nonUnc |
| + unc-32 | nonUncnonDpy | Unc | 124 Unc |

For map positions of genetic markers, see FIG. 4A.
Male heterozygous for unc-32 were used because homozygous unc-32 males cannot mate.
The underlined gives the phenotypes of expected cross progeny if mab-21/yDf10 were viable.
Viable self progeny are Dpy or have a distinctive rubberband phenotype due to unc-93.

In corresponding crosses lacking the mab-21 mutation, yDf10 heterozygotes were present in the expected proportion. mab-21/yDf10 is concluded to be a lethal combination, and that the null phenotype of mab-21 is lethality prior to hatching. Since the phenotype of the existing mab-21(bx53) is more severe over a deficiency, and because the mutant phenotype of the two mab-21 alleles is similar to that of bx53, All these mutations are concluded to be most likely hypomorphs.

Alleles of known essential genes in the vicinity of mab-21 were tested for complementation with mab-21 (Schierenberg et al., 1980; Cassada et al., 1981) (Materials and Methods). Alleles of emb-1, emb-2, emb-5, emb-7, emb-8, emb-13, and emb-32 all complemented the ray 6 defect of mab-21 (bx53) males. Therefore none of these mutations is likely to be a strong allele of mab-21, and mab-21 appears to define a new essential gene.

In order to gain information about the stage of embryonic arrest in a mab-21 near-null background, the dead embryos arising from a cross between a mab-21 carrying strain and a yDf10 carrying strain were examined and compared these to dead embryos that segregated from a yDf10/+ strain during self propagation. 47% (36/76) of dead eggs resulting from the cross had completed the proliferation stage of embryogenesis and were arrested during the morphogenesis stage, whereas only 2% (1/56) of the dead eggs segregating from the yDf10/+ heterozygote progressed this far. Therefore, it was concluded that mab-21/yDf10 heterozygous embryos can complete cellular proliferation and that decreased level of mab-21 function causes arrest during morphogenesis.

mab-21 Encodes a Novel Protein

The mab-21 gene was cloned by identifying cosmids (kindly supplied by the C. elegans sequencing consortium) that rescued the mab-21 male tail phenotype. Candidate cosmids for testing were identified by mapping mab-21 between two restriction fragment length polymorphisms, MJ#NEC2 and MH#NEC1 (FIG. 4B, see Materials and Methods). A 5.6 kb rescuing genomic fragment (EM#219) was used to screen a cDNA library (Palazzolo et al., 1990), resulting in the recovery of 8 cDNA clones from 250,000 plaques screened. Seven of the cDNA clones were of 1.3 kb and differed only by having 5' ends located at different positions within a 26 bp genomic region. The eighth cDNA was of 0.7 kb and was colinear with the 3' portion of the other cDNA's. It was showed that these cDNA's represented transcripts of the mab-21 locus in two ways. First, expression of all these cDNA's (except the 0.7 kb cDNA) under the control of a heat shock promoter resulted in rescue of the mab-21 mutant phenotype, as described more fully below. Second, introduction of a mutation into the coding region of EM#219 abolished the ability of this fragment to rescue a mab-21 mutation (Materials and Methods). Third, a genomic fragment (EM#228) covering all of the genomic region covered by EM#227 with the exception of the region encoding the 3' end of the cDNAs failed to rescue a mab-21 mutation (FIG. 4B).

DNA sequence analysis revealed that the cDNA clones contained an open reading frame encoding a protein of 386 amino acids (FIG. 4C). Search of Genebank and EMBL databases with GCG FASTA and TFASTA identified no previously described proteins with significant similarity to this conceptual protein. Thus the mab-21 locus encodes a novel protein.

mab-21 Function is Required During Late L3 or L4 Larval Stages

As discussed above, the male tail mutant phenotype of mab-21 suggested that mab-21 was required for a pattern formation mechanism that directed cell fate choices of seam cells during the late L3 larval stage. To determine whether mab-21 gene function was required at a time consistent with this model, applicant expressed mab-21 from a heat shock promoter at various times in a mab-21 mutant background (FIG. 5). It was found that the interval during which heat shock resulted in the highest frequency of rescue of the mab-21 mutant phenotype (both the ray 6 defect and the ectopic ray defect) included the time when ray precursor cells were present. Therefore mab-21 function could be required by one or more ray precursor cells. Alternatively, heat shock starting at this time might be necessary in order to accumulate enough mab-21 protein for function at a later time.

mab-21 Functions Cell Autonomously for Choice of Ray Identity by R6, but Non-Autonomously for Choice of Hypodermal Versus Neuroblast Cell Fate by T.apapa Results of our previous cell ablation experiments suggested that genes required for specification of ray morphological identities acted autonomously within the terminal branches of the ray lineages (Chow and Emmons, 1994). (Terminal branches are defined as those branches leading to or contributing to single rays.) Therefore it was expected that mab-21(+) was required in R6 or a descendant of R6 for correct specification of ray 6 morphology, ultrastructure, and position. In order to test this prediction, as well as to determine whether the choice of hypodermal versus neuroblast cell fate by T.apapa was cell autonomous, carried out a mosaic analysis of mab-21 function, as well as a laser ablation study in a mab-21 mutant background. It was found that expression of mab-21(+) within the V6 lineage was both necessary and sufficient for wild type ray 6 position and morphology, whereas expression of mab-21(+) within T.apapa was not necessary for preventing expression of the neuroblast fate by this cell. Expression within either the T or the V6 lineage was sufficient for preventing expression of the neuroblast cell fate by T.apapa. The laser ablation study confirmed that the presence or absence of R6 can affect the fate of T.apapa.

For mosaic analysis, a strain carrying the three linked mutations mab-21 (bx53) ncl -1 (e1865) unc-36(e251) III as well as a free duplication, sDp3 (III;f), that carries wild type alleles of each of these genes were used (FIG. 4A). sDp3 is spontaneously lost during the cell lineage with a frequency variously estimated to be 1 per 400 cell divisions (Kenyon, 1986) or 1 per 300 cell divisions (Herman, 1989). Mosaic animals in which duplication loss had occurred were identified as Unc animals with wild type male tails, or nonUnc animals with mutant male tails, and the probable point of duplication loss was determined for such animals by analysis of the Ncl phenotype of cells representing several lineages (FIG. 6; Materials and Methods). By this means, 36 mosaic animals were identified and could be placed into one of four classes. The cells scored and the points of duplication loss for each mosaic class are shown in FIG. 6; the phenotypes of the mosaics are summarized in Table 2.

Class I represented probable loss of the duplication in AB.p (Ia) or in the AB.pa (Ib) or AB.pp (Ic) branches; these animals lacked a wild type copy of the gene in T-apapa. Animals of this class had wild type male tails. This indicated that mab-21(+) gene function was not necessary within descendants of AB.p, which included T and its descendants T.apapa and R7, for either wild type ray 6 or correct choice of the hypodermal cell fate by T.apapa. Class II animals had lost the duplication in AB.a (IIa), or in the AB.al(IIb) or AB.ar(IIc) branches; these animals most likely lacked a wild type gene copy in R6. Such animals were mutant for ray 6 on one (IIb and IIc) or both (IIa) sides, consistent with a requirement for mab-21(+) within R6 or one of its descendants. Expression of mab-21 function within the large hypodermal syncytium, hyp7, appeared unlikely, because Class II mosaics would be expected to have large numbers of syncytial nuclei carrying the mab-21(+) gene. Class II animals were wild type for choice of hypodermal cell fate by T.apapa, indicating expression of mab-21(+) in R6 was not necessary for correct specification of T.apapa cell fate.

In class III animals, the duplication was lost in AB, and as expected, such animals were bilaterally mutant for ray 6. Two of the three class III animals had ectopic rays unilaterally. Taken together with the previous results, this indicates that expression of mab-21(+) in either the AB.a or AB.p branches is sufficient for specification of wild type T.apapa cell fate, but that expression in at least one of these two lineages is necessary. Finally, the single animal of class IV, where the duplication was lost in P1, had a wild type male tail as expected.

One possible interpretation of mosaics is that the presence of mab-21(+) activity in the V6 lineage prevents expression of the neuroblast cell fate by a T.apapa cell lacking mab-21 gene function (class I mosaics). This suggested an existence of an interaction between R6 and T.apapa that could affect the fate of T.apapa. Direct evidence for such an interaction was obtained by cell ablation experiments carried out on mab-21 mutant animals (Table 2).

TABLE 2

V6 and T lineage phenotypes of mosaic animals

| Class | Dp loss | mab-21 genotype R6 | mab-21 genotype T | ray 6 | Phenotype ectopic ray |
|---|---|---|---|---|---|
| I | AB.p | + | − | wild type | absent |
| II | AB.a | − | + | fused | absent |
| III present | AB (2/6) | − | − | fused | |
| IV | P1 | + | + | wild type | absent |

Consistent with our earlier results in a wild type background (Chow and Emmons, 1994), most ablations in a mab-21 mutant background had no effect on unablated cells. However, ablation of R6 or its mother reduced the frequency of expression of the neuroblast fate by T.apapa from around 45% to 2.3% (1/43). Therefore in a mab-21 mutant background presence of R6 causes T.apapa to express the neuroblast cell fate with increased frequency.

Figure 7:
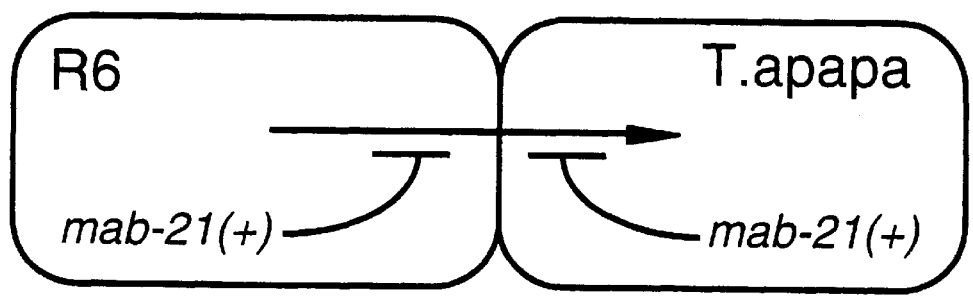
FIG. 7: Model for action of mab-21 to block a cell signal.

This interaction between R6 and T.apapa in a mab-21 mutant background might be direct or indirect. R6 itself might send an inductive signal or blocks an inhibitory signal received by T.apapa (direct interaction), or R6 might simply by its physical presence cause T.apapa to be exposed to an inducing signal or prevent exposure to a blocking signal from another source (indirect interaction). Only the first of these two alternatives is consistent with the results of the mosaic analysis. Expression of mab-21(+) within one or more cells of the AB.a lineage, presumably R6, prevents interactions between R6 and T.apapa, or makes it ineffective (as does expression of mab-21 (+) within T.apapa itself). Since gene expression within R6 alters the interaction between R6 and T.apapa, this interaction is likely to be occurring directly between these two cells (FIG. 7).

TABLE 3

Frequency of T. apapa-derived ray after ablation of seam cells

| Cell Ablated | n | Ray from T. apapa |
|---|---|---|
| None | >600 | (45%) |
| T. appp (R8/9) | 16 | 10 (63%) |
| R7 | 11 | 5 (46%) |
| T. apapa | 11 | 0 (0%) |
| R6 | 25 | 1 (4%) |
| R5 | 17 | 7 (41%) |
| R4 | 13 | 7 (54%) |
| R3 | 13 | 7 (54%) |
| R2 | 10 | 5 (50%) |
| R1 | 10 | 4 (40%) |
| V6. pppp (R5/R6) | 18 | 0 (0%) |
| T | 27 | 0 (0%) | n, the number of sides examined.
Ablation did not affect the identities of rays derived from the remaining cells.
A fused 4–6 ray was present except in the following cases: after ablation of R6 and V6. pppp a normal ray 4 was present: after ablation of R5 (35%) and R4 (100%) ray 6 was not fused and was present as a thin, cylindrical ray located near or at the normal position of ray 4.

Experimental Discussion mab-21 mutants affect the differentiation of four cells present bilaterally in the posterior epidermis of the male tail. Two of these cells, R6st and R6B are components of ray 6, one of nine sensory rays, while a third (R6.p) is a hypodermal product of the same cell sublineage that generates the cells of ray 6. In mab-21 mutants, each of the three cells R6st, R6B, and R6.p adopts a fate or differentiates in a manner similar to that of the corresponding cell of the adjacent more anterior ray sublineage (ray 4). It was shown that mab-21(+) activity is likely to be required within the ray 6 sublineage. However, it is not known whether its action is required cell autonomously within each ray 6 cell individually. It could be that the effects on some cells are secondary to effects on other cells. One possible explanation for the diverse effects of mab-21 mutations on these three cells is that mab-21(+) activity is required only by the ray precursor cell R6, which in a mab-21 mutant background appears to assume the identity of its anterior neighbor R4. This interpretation is consistent with the earliest possible time of action of mab-21, which was when R6 was present.

mab-21 mutations also affect a fourth cell, a hypodermal seam cell similar to R6. This cell, T.apapa, is born at the same time as R6 and, like R6, moves posteriorly out of the seam after it is born and becomes the immediate posterior neighbor of R6 (FIGS. 1C, D). In mab-21 mutants, T.apapa was frequently transformed into a ray precursor cell and expressed the ray sublineage. Thus in mab-21 mutants both T. appa and R6 assume characteristics of more anterior seam cells. It seems most likely that mab-21 acts as part of a pattern formation mechanism that dictates the fates of seam cells during the late L3 and early L4 larval stages.

It is demonstrated that in a mab-21 background, a signal form R6 causes T.apapa to express the ray neuroblast cell fate. Action of mab-21(+) in either R6 or T.apapa blocks the effect of this signal. This evidence for signaling between seam cells and its modulation by cell-autonomous functions is consistent with previous observations, both in C.elegans and in other organisms. A signal from the posterior seam cell T inhibits the expression of ray lineages by its anterior neighbor V6 (Waring and Kenyon, 1990). In wild type, V6 overcomes this inhibition by the cell-autonomous action of the homeobox transcription factor pal-1 (Waring and Kenyon, 1991). Signalling between seam cells is necessary for expression of the postdeirid neuroblast cell fate by V5.pa (Waring et al., 1992). In this case, effective signalling requires cell contact, and this must be maintained on both sides of V5.p in order for this cell to divide asymmetrically (Austin and Kenyon, 1994). Seam cells in C. elegans, like epithelial cells in other organisms, are joined by adherens junctions (Priess and Hirsh, 1986; Baird et al., 1991). Signals passing between epithelial cells that influence their fates are important in the development of many if not all animals (for reviews see Horvitz and Herskowitz, 1992; Greenwald and Rubin, 1992; Peifer et al., 1993).

One possible consequence of signalling between epidermal cells is modulation of levels of expression of HOM-C/Hox genes, which give cells their regional identities. In C. elegans, the effect of the above-mentioned T inhibition on V6 is proposed to be to prevent expression of the HOM-C/Hox gene mab-5, which is required for the male-specific divisions of the V6 lineage, including the ray sublineage (Waring and Kenyon, 1990; 1991). Likewise, a likely consequence of contact between V5.p and its neighbors is modulation of the expression of mab-5 within the V5 lineage (Austin and Kenyon, 1994).

It was shown previously that the HOM-C/Hox genes mab-5 and egl-5 function in specifying the identities of rays 1–6 (Chow and Emmons, 1994). mab-5 is most closely related to Drosophila Antennapedia, while egl-5 is most closely related to Drosophila Abdominal B (Wang et al., 1993). The relative levels of expression of these two genes within the terminal cells of the ray lineages help to specify the morphological identity assumed by each ray. In particular, egl-5 is weakly haplo insufficient for expression of the identity of ray 6: in egl-5(0)/+heterozygotes, ray 6 occasionally (7% assumes the identity of ray 4 and fuses with ray 4 (Chow and Emmons, 1994).

The function of mab-21 may be related to the role of egl-5 in specification of the development of ray 6. mab-21 mutants are fully penetrant for the same ray 6 to 4 transformation phenotype weakly expressed in egl-5 heterozygotes. Furthermore, mab-21 mutations, themselves recessive, are dominant enhancers of the haploinsufficient phenotype of egl-5. Heterozygosity for a mab-21 mutation increased the frequency of transformation of ray 6 to ray 4 in a heterozygous egl-5 background from 7% to over 30% (Chow and Emmons, 1994). Thus a decreased level of egl-5(+) gene function makes R6 sensitive to the level of mab-21 gene function. Because egl-5 modifies the cellular environment in which mab-21 acts, this argues that the two genes function in the same or related pathways in determination of the identity of ray 6. As mab-21 also acts in other body regions in addition to toe posterior seam of males, and indeed has an essential embryonic function, it is possible that mab-21 plays a much wider role in implementing the action of HOM-C/Hox genes.

In spite of the fact that HOM-C/Hox genes have been recognized for some time as encoding transcription factors that play a key role in regional specialization within the metazoan body, large gaps remain in our understanding of their mode of action. Because the mab-21 gene encodes a putative protein of hitherto unreported amino acid sequence, it is not possible to predict whether it might play a role in regulation of transcription of egl-5 or in target gene selectivity of egl-5, possibly as a cofactor. Another possibility for the function of a HOM-C/Hox gene modifier such as mab-21 is that it acts in the upstream pathways that restrict the expression of HOM-C/Hox genes to certain body regions. Thus a further possibility for mab-21 action is as a component of the pattern formation mechanisms that set the expression levels of HOM-C/Hox genes in the seam cells.

References

Andrew, D. J. and Scott, M. P. (1992). Downstream of the homeotic genes. new biol. 4, 5–15.

Austin, J., and C. Kenyon. (1994). Cell contact regulates neuroblast formation in the Caenorhabditis elegans lateral epidermis. Development 120:313–324.

Baird, S. E., D. H. A. Fitch, I. A. A. Kassem, and S. W. Emmons. (1991). Pattern formation in the nematode epidermis: determination of the arrangement of peripheral sense organs in the C. elegans male tail. Development 113:515–526.

Botas, J. (1993) Control of morphogenesis and differentiation by HOM/hox genes. Curr. Opin. Cell Biol. 5, 1015–1022.

Brenner, S. (1974) The genetics of Caenorhabditis elegans. Genetics. 77:71–94

Cassada, R., E. Isnenghi, M. Culotti, and G. Von Ehrenstein. (1981). Genetic analysis of temperature-sensitive embryogenesis mutants in Caenorhabditis elegans. Develop. Biol. 84:193–205.

Chow, K. L., and S. W. Emmons. (1994). HOM-C genes and four interacting loci determine the morphogenetic properties of single cells in the nematode male tail. Development.

Devereux, J., Haeberli, P., and Smithies, O. (1984). A comprehensive set of sequence analysis programs for the VAX. NAR 12, 387–395.

Finney, M., and G. Ruvkun. (1990). The unc-86 gene product couples cell lineage and cell identity in C. elegans. Cell 63:895–905.

Fire, A., S. White-Harrison, and D. Dixon. (1990). A modular set of lacZ fusion vectors for studying gene expression in Caenorhabditis elegans. Gene 93:189–198.

Greenwald, I. S., P. W. Sternberg, and H. R. Horvitz. (1983). The lin-12 locus specifies cell fates in Caenorhabditis elegans. Cell 34:435–444.

Hall, D. H. (1995) Electron microscopy and 3D image reconstruction. In C. elegans: Modern Biological Analysis of an Organism. Methods in Cell Biology, Vol.48. (H. F. Epstein and D. C. Shakes, eds.) Academic Press, New York, in press.

Herman, R. K., (1984) Analysis of genetic mosaics of the nematode Caenorhabditis elegans. Genetics 108, 165–180.

Herman, R. K. (1989) Mosaic analysis in the nematode Caenorhabditis elegans. J. Neurogenetics 5, 1–24.

Hodgkin, J., H. R. Horvitz, and S. Brenner. (1979). Non-disjunction mutants of the nematode Caenorhabditis elegans Genetics. 91:67–94.

Horvitz, H. R., and Herskowitz, I. (1992). Mechanisms of asymmetric cell division: two Bs or not two Bs, that is the question. *Cell* 68, 237–255.

Kenyon, C. (1986). A gene involved in the development of the posterior body region of *C. elegans*. *Cell* 46:477–487.

Kramer, J. M., R. P. French, E. C. Park, and J. J. Jonhson. (1990). The *Caenorhabditis elegans* rol-6 gene, which interacts with the sqt-1 collagen gene to determine organismal morphology, encodes a collagen. *Mol. Cell. Biol.* 10:2081–2089.

Levy, A. D., J. Yang, and J. M. Kramer. (1993). Molecular and genetics analyses of the *Caenorhabditis elegans* dpy-2 and dpy-10 collagen genes: a variety of molecular alterations affect organismal morphology. *Mol. Biol. Cell.* 4:803–817

Liu, K. S., and Sternberg, P. W. (1995). Sensory regulation of male mating behavior in *Caenorhabditis elegans*. *Neuron* 14, 1–20.

Loer, C. M., and Kenyon, C. J. (1993) Serotonin-deficient mutants and male mating behavior in the nematode *Caenorhabditis elegans*. *J.Neurosci.* 13, 5407–5417.

McGinnis, W., and Krumlauf, R. (1992) Homeobox genes and axial patterning. *Cell* 68,283–302.

Mello, C. C., J. M. Kramer, D. Stinchcomb, and V. Ambros. (1991). Efficient gene transfer in *C. elegans*:Extrachromosomal maintenance and integration of transforming sequences. *EMBO L*. 10:3959–3970.

Palazzolo, M. J., B. A. Hamilton, D. Ding, C. H. Martin, D. A. Mead, R. C. Mierendorf, K. V. Raghavan, E. M. Meyerowitz, and H. D. Lipshitz. (1990). Phage lambda cDNA cloning vectors for subtractive hybridization, fusion-protein synthesis and Cre-loxP automatic plasmid subcloning. *Gene* 88:25–36.

Peifer, M., Orsulic, S., Pai, L. M., and Loureiro, J. (1993). A model system for cell adhesion and signal transduction in Drosophila. *Development* 1993 *Suppl.*, 163–176.

Priess, J. R., and D. I. Hirsh. (1986). *Caenorhabditis elegans* morphogenesis: the role of the cytoskeleton in elongation of the embryo. *Dev. Biol.* 117:156–173.

Rosenbluth, R. E., Cuddeford, C., and Baillie, D. L. (1985). Mutagenesis in *Caenorhabditis elegans*. II. A spectrum of mutational events induced with 1500 R of gamma-radiation. *Genetics* 109, 493–511.

Schierenberg, E., J. Miwa, and G. von Ehrenstein. (1980). Cell lineages and developmental defects of temperature-sensitive embryonic arrest mutants in *Caenorhabditis elegans*. *Develop. Biol.* 76, 141–159.

Sulston, J. E. and Horvits, H. R. (1977). Post-embryonic cell lineages of the nematode *Caenorhabditis elegans*. *Dev. Biol.* 76, 141–159.

Sulston, J. E., D. G. Albertson, and J. N. Thompson. (1980). The *Caenorhabditis elegans* male: postembryonic development of nongonadal structures. *Dev. Biol.* 78:542–576.

Sulston, J., and Hodgkin, J. (1988) Methods. In Wood, W. B. (ed.) The Nematode *Caenorhabditis elegans*. Cold Spring Harbor Laboratory Press. pp587–606.

Wang, B. B., M. M. Muller-Immergluck, J. Austin, N. T. Robinson, A.Chisholm, and C. Kenyon. (1993). A homeotic gene cluster patterns the anteroposterior body axis of *C. elegans*. *Cell* 74:29–42.

Waring, D., and Kenyon, C. (1990). Selective silencing of cell communication influences anteroposterior pattern formation in *C. elegans*. *Cell* 60, 123–131.

Waring, D. A., and Kenyon, C. (1991). Regulation of cellular responsiveness to inductive signals in the developing *C. elegans* nervous system. *Nature* 350, 712–715.

Waring, D. A., Wrischnik, L., and Kenyon, C. (1992). Cell signals allow the expression of a pre-existent neural patter in *C. elegans*. *Development* 116, 457–466.

Zhang, Y. and Emmons, S. W. (1995). Specification of sense-organ identity by a *Caenorhabditis elegans* Pax-6 homologue. *Nature* 377, 55–59.

Second Series of Experiments 1. mab-21 AND DISEASES a. Comparison of mab-21 and mab-18 phenotypes It was noted that the mab-21 and mab-18 shared their mutant phenotypes. Both mutations affect the differentiation of sensory ray 6, conical shape structure in wild type animal. Ray 6 is transformed into a thin ray resembling ray 4, and both of them fuse to form a thick fused ray. Although these two genes are mapped on different chromosome (linkage group III and linkage group X respectively) (Baird et al., 1990), the phenotype alone has indicated that they may play similar or related functional role in sensory organ differentiation. This idea has prompted us to analyze the genetic interaction between them.

b. Genetic interaction

Subsequent genetic experiments show that heterozygous mutation of either one of the mutations results in no phenotype. On the other hand, double heterozygous populations have a fraction of the animals with a phenotype resembling homozygous mutation of mab-21 or mab-18 gene (Chow and Emmons, 1994). Such genetic interaction test is a common method in genetic analysis to infer genes participating in the same genetic pathway.

In parallel experiments, mab-21 has been shown to interact with another group of homeodomain containing transcription factor genes belonging to the HOM-C/Hox class (Chow and Emmons, 1994). While HOM-C/Hox class genes are highly conserved in hydra, worm, fly, fish, mouse and human, their interaction with mab-21 substantiates the fact that mab-21 is part of a conserved mechanism present in invertebrate and vertebrate systems. It has been implicated to interact with these conserved genes in local pattern formation of the sensory tissues.

c. mab-18 Sequence is Homologous to PAX-6 (Aniridia) in Human, pax-6 (small eye) in Mouse, Eyeless in Drosophila mab-18 gene has been molecularly analyzed and sequenced. It encodes a homeodomain containing transcription factor (Zhang and Emmons, 1995) with homologs in invertebrate and vertebrate systems (Quiring et al., 1994; Krauss et al., 1991; Puschel et al., 1992).

The human and mouse homologs are called PAX-6 (Jordan et al., 1992; Glaser et al., 1992) and pax-6 (Walther and Gruss, 1991). They were identified by sequence homology to a group of Drosophila developmentally important genes. These genes have a homeodomain and an adjacent paired domain, both of which are required for DNA binding. Subsequent mutation analyses have linked the human PAX-6 gene mutation with a human disease called Aniridia (Glaser et al., 1992) affecting iris differentiation, and pax-6 gene mutation with a mouse mutation called small eye (Schmahl et al., 1993). In both cases, the eye development has been affected.

Recently, a Drosophila homolog of mab-18 was isolated (Quiring et al., 1994). The gene was called eyeless, mutation of which results in no eye in the animal. Ectopic expression of the gene can induce formation of additional eyes in tissue normally not differentiating into eye (Halder et al., 1995a). In the same study, experiments have been conducted to prove that the human PAX-6 gene can functionally substitute the Drosophila gene and rescue the Drosophila mutation.

These results suggest that pax-6 like genes are involved in a developmental pathway of eye formation which is highly conserved from invertebrate to vertebrate (Halder et al. 1995b). Based on the conservation of the components in this pathway, applicant postulates that eye development in Drosophila, mouse and human is molecularly equivalent to the sensory ray differentiation in nematode.

d. mab-21 Acts Together With pax-6 in the Same Pathway

The genetic characterization of mab-21 indicates that mab-21 interacts with mab-18, and is acting in the same evolutionary conserved genetic pathway. While mutation of mab-18 and its homologs result in a variety of abnormality and disease associated with sensory organ formation as described in (c), applicant believes that mutations of mab-21 homologs in vertebrate are also associated with abnormality which may have a disease state related to that of Aniridia caused by mutation in the human PAX-6 gene, and may affect peripheral neural tissue differentiation.

e. Homologs of mab-21 Identified

The cellular and genetic components with that mab-21 interacts are highly conserved across phyla in the animal kingdom. Applicant believes early on that the homologs of mab-21 exist in other invertebrates as well as vertebrates. The homolog of a closely related species of Caenorhabditis elegans, C. briggsae was isolated. From a genomic library screen, applicant isolated four genomic clones using the C. elegans mab-21 cDNA as probe. From the sequence analyzed so far, the homology with C. elegans mab-21 is greater than 95%. [see section 2 for detail].

From the search of Genebank sequence database, two human EST clones were identified in the Merck-St.Louis EST project. When compared with the genomic sequence from the cosmid containing mab-21 locus, both EST sequences share greater than 70% homology to the worm gene. While these clones are isolated from a brain library, it implies that the human mab-21 gene is expressed in neural tissue.

Subsequently, Margolis et al. reported identification of a number of cDNAs they called CAGR1 which are also homologous to the nematode mab-21 gene with an overall greater than 60 percent homology on the amino acid sequence level (Margolis et al., pers. comm.) (FIG. 8). Recent experiments have shown that expression of the human cDNA can substitute the mab-21 function in mutant C. elegans worms. This result proves the functional homology of these genes. While these CAGR1 cDNAs were isolated from human retina and cerebral cortex cDNA libraries, this fact strengthens the association of mab-21 with neural function, and further hints its role in sensory organ development.

f. Human mab-21 is Mapped to Human Chromosome 13q13

Human mab-21 has been localized onto human chromosome 13 band q13 (Margolis et al., pers. comm.). Applicant believes that loci corresponding to the human mab-21 may have been described by mutations previously associated with that chromosomal region. Search in Genome Database at University of Pennsylvania revealed that there are a number of loci in the same region. However, as the above disclosure makes clear that mab-21 affects sensory organ and mab-18 homolog mutation phenotype affects eye development, a candidate locus stands out by its own. Moebius Syndrome mapped to 13q13 (Slee et al., 1991). The phenotype described for Moebius include cranial facial palsy, congenital oculofacial paralysis, oculofacialbulbar palsy, hypoplasia of tongue, mask (expressionless) face, oculomotor nerve defect (failure of lateral eye movement), trochlear nerve defect, malformation of orofacial structures (swallowing and speech difficulties), and branchial muscle defect (Kumar, 1990). Based on the phenotypes which can be associated with cranial facial nerve function and development, applicant is currently testing that Moebius Syndrome is the manifestation of mab-21 mutation.

2. IDENTIFICATION OF mab-21 HOMOLOG IN OTHER NEMATODE SPECIES

C. elegans mab-21 complete cDNA was used as the probe. The DNA fragment was labeled by random priming procedure to generate radioactively labeled DNA probe for screening C. briggsae genomic library kindly provided by Dr. David Baillie of Simon Fraser University, Canada. The phages were plated out at concentration of about 1000 pfu/plate. Out of about 30,000 pfu screened, i.e. greater than 5 genomic equivalents, four independent clones were isolated. Only Cb#17 was subcloned. Deletions were generated and sequenced. DNA sequence and the predicted protein amino acid sequence (FIG. 9) suggests that Cb#17 corresponds to the 3' end portion of the C. briggsae mab-21. While the other three clones corresponds to the 5' genomic region of the gene.

Recently, an EST sequence deposited to the gene bank database was found to have high similarity to the 5' region of C. elegans mab-21 gene. It is representing the mab-21 homolog in a parasitic nematode Brugia malayi (FIG. 10).

3. IDENTIFICATION OF HOMOLOGS OF mab-21 a. F35G12.6 in C. elegans

F35G12 and C56A8 are the cosmids that can rescue the mab-21 mutant phenotype by DNA transformation into mutant gonad (Chow and Emmons, 1995). Overlapping region of these two cosmids defines the mab-21 gene. In that region, a number of ORF has been predicted by the Genefinder program used in the A Caenorhabditis elegans Database (ACEDB), one of which is F35G12.6. The F35G12.6 ORF is at the corresponding position of a 5.6 Kb genomic fragment which has been shown by deletion/transformation rescue assay to contain mab-21 gene (Chow et al., 1995). However, due to errors in the submitted sequence of the cosmid F35G12, the ORF F35G12.6 encodes a protein slightly different from the protein product predicted from the mab-21 cDNA (FIG. 8 and FIG. 11).

b. Human Homolog for mab-21 Search

The human homolog reported by Margolis et al. can be obtained from NCBI's Genebank Database Query function using "mab-21" as the keyword. (FIG. 12)

c. Human Homolog in EST Project

In the University of Washington (St.Louis)-Merck EST project, two cDNA clones were deposited to the Genebank. They are ym36d10 (FIG. 13) and ym45dll (FIG. 14). Both have been identified as having sequence homology to F35G12.6. They were pulled out from search using F35G12 as the keyword (These two clones will not be identified using mab-21 as keyword.). Since F35G12.6 corresponds to the C.elegans mab-21 gene, the two EST clones should have homology to mab-21 cDNA sequence. Alignment test by SeqVu 1.0 program does confirm this notion. The two EST clones corresponding to two truncated cDNAs with most of the 3' portion of the human mab-21 transcript.

4. EXPRESSION OF NEMATODE MAB-21 PROTEIN IN BACTERIAL CELLS AND YEAST a. mab-21 cDNA had been inserted into bacterial expression vector with a maltose binding protein tag (MBP). Fusion protein (MBP-MAB-21) was generated as cytosolic protein in bacterial cell. Cell lysate had been passed into affinity chromatographic column with maltose coupled with Sephadex resin. The impurities were eluted with the MBP-MAB-21 retained in the column. The fusion was eluted later with maltose solution, dialyzed and cleaved with factor Xa, a protease that could digest and separate the MBP tag from the MAB-21 protein (FIGS. 16, 17).

b. mab-21 cDNA had also been inserted into yeast vector under the regulation of the GAL-1 promoter, and in front of a galactosidase gene. Induction by galactose in yeast culture medium generated fusion protein of MAB-21-Galactosidase. The fusion protein had enzymatic activity of galacosidase, by enzyme assay. The fusion protein could also be detected by antibody against galactosidase. In both enzymatic assay and immunostaining study, it was revealed that the fusion protein was expressed in the nuclei of yeast cells. Similar subcellular localization of fusion protein was observed in worm.

5. PRODUCTION OF ANTIBODIES AGAINST MAB-21 PROTEIN

The bacterial expressed MAB-21 protein had been used for immunization of mouse and rat, antisera from six mice and six rats are now available. Preliminary tests of the sera by both Western blot assay (FIG. 18) and ELISA assay (FIG. 19) show positive identification of the MAB-21 protein in bacteria and in nematode. This suggests that the rationale of generating immunoreagents in one the claims is sound, and valid, and experimental work is feasible.

6. IDENTIFICATION AND ISOLATION OF MORE MAB-21 HOMOLOGS AND OTHER STUDIES

Homologs of mab-21 in a variety of animals species, including hydra, Artemia, Drosophila, Xenopus (frog), zebrafish, mouse and human are being isolated. Preliminary data shown in FIG. 8 suggest that the gene products are highly conserved, and vertebrate homologs are present in human beings.

The human homolog of mab-21 gene will be used to perform Northern analysis to examine the normal expression pattern of the gene, and to correlate its function in neural tissues during development.

Isolation of the mouse mab-21 homolog by polymerase chain reaction and hybridization screening is also in progress. Preliminary data are shown in FIG. 15. The homologous sequences are currently used to localize the gene onto a specific chromosome by fluorescent in situ hybridization, and to correlate the gene with existing genetic mutation identified in mouse. In fact, by syntenic analysis of the human and mouse genome, there are candidate mutant loci which may correspond to the mouse mab-21 gene.

Subsequently, knock out transgenic mouse will be used to establish a vertebrate animal model to examine the function of mab-21 gene, and the potential manifestation of the disease state with the absence of the gene function.

Mutation(s) associated with the three existing allele of mab-21 mutation are being characterized to determine the functional significance of various domain of the protein.

Genetic experiments are in the set up process for identification of suppressors, enhancers and modifiers of mab-21 mutation, in hope of identifying various components in the genetic pathway involving mab-21 gene function.

Experiments are in progress to overexpress the protein in various animal model systems to examine the role of mab-21 gene in normal development.

Experiments using MAB-21 protein as starting material to looking for additional interacting proteins are in the preparation stage. It includes experiments using the antibodies specific for MAB-21 protein for co-immunoprecipitation of the interacting protein together with MAB-21 protein. Genetic approach using yeast two hybrid system or interaction trap system to identify interacting proteins is also in progress. Specifically, demonstration of a direct interaction of MAB-21 protein with MAB-18 protein will strengthen the genetic support for the involvement of mab-21 gene or its homologs in developmental functions involving mab-18 gene and its homologs, e.g. sensory organ differentiation and neural patterning.

7. REFERENCES:

Baird, S. E. Fitch, D. H. A., Kassem, I. A. A. and Emmons, S. W. (1991) Pattern formation in the nematode epidermis: determination of the arrangement of peripheral sense organs in the *C. elegans* male tail. Development 113, 515–526.

Chow, K. L. and Emmons, S. W. (1994) HOM-C/Hox genes and four interacting loci determine the morphogenetic properties of single cells in nematode mail tail. Development 120, 2579–2593.

Chow, K. L., Hall, D. and Emmons, S. W. (1995) The mab-21 gene of *Caenorhabditis elegans* encodes a novel protein required for choice of alternate cell fates. Development 121, 3615–3626.

Glaser, T., Walton, D. S. and Maas, R. L. (1992) Genomic structure, evolutionary conservation and *aniridia* mutations in the human PAX 6 gene. Nature Genetics 2, 232–238.

Grindley, J. C., Davidson, D. R. and Hill R. E. (1995) The role of Pax-6 in eye and nasal development. Development 121, 1433–1442.

Halder, G., Gallaerts, P. and Gehring, W. J. (1995a) Induction of ectopic eyes by targeted expression of the eyeless gene in Drosoplila. Science 267,1788–1792.

Halder, G., Gallaerts, P. and Gehring, W. J. (1995b) New perspectives on eye evolution. Curr. Opin. Genet. Develop. 5,602–609.

Hanson, I and Van Heyningen, V. (1995) Trends Genet. 11, 268–272.

Jordan, T. Hanson, I., Zaletayev, D., Hodgson, S., Prosser, J., Seawright, A., Hastie, N. and Van Heyningen, V. (1992) Nature Genet. 1, 328–332.

Krauss, S., Johansen, T., Korzh, V., Moens, U., Ericson, J. U. and Fjose, A., (1991) Zebrafish pax[zf-a]: a paired box containing gene expressed in the neural tube. EMBO J. 10,3609–3619.

Kumar, D. (1990) Moebius syndrome. J. Med. Genet. 27, 122–126.

Puschel, A. W., Gruss, P. and Westerfield, M. (1992) Sequence and expression pattern of pax-6 are highly conserved between zebrafish and mice. Development 114, 643–651.

Quiring, R., Walldorf, U., Kloter, U. and Gehring, W. J. (1994) Homology of the eyeless gene of Drosophila to the small eye gene in mice and *aniridia* in humans. Science 265, 785–789.

Schmahl, W., Knoedlseder, M., Favor, J. and Davidson, D. (1993) Defect of neuronal migration and the pathogenesis of cortical malformations are associated with Small eye (Sey) in the mouse, a point mutation at the Pax-6 locus. Acta Neuropathol. 86, 126–135.

Slee, J. J., Smart, R. D. and Viljoen, D. L. (1991) Deletion of chromosome 13 in Moebius syndrome. J. Med. Genet. 28, 413–414.

Walther, C., Guenet, J. L., Simon, D., Deutsch, U., Jostes, B., Goulding, M. D., Plachov, D., Balling, R. and Gruss, P. (1991) Genomics 11, 424–434.

Zhang, Y. and Emmons, S. W. (1995) Specification of sense organ identity by a *Caenorhabditis elegans* Pax-6 homologue. Nature 377, 55–59.

What is claimed is:

1. A method of detecting expression of mab-21 or its homologs in a sample which comprises steps of:

a) obtaining total mRNA from the sample;

b) contacting the mRSA so obtained with a labelled nucleic acid molecule of at least 15 nucleotides which specifically hybridizes with a polynucleotide encoding MAB-21 protein under hybridizing conditions allowing specific hybridization; and c) determining the presence of mRNA hybridized to the molecule, and thereby detecting the expression of the mab-21 or its homologs in the sample.

2. A method of claim 1, wherein the sample contains animal tissues or animal cells.

* * * * *